US008673579B2

(12) United States Patent
Orser et al.

(10) Patent No.: US 8,673,579 B2
(45) Date of Patent: Mar. 18, 2014

(54) PEPTIDE PROBES FOR DIAGNOSTICS AND THERAPEUTICS

(75) Inventors: Cindy S. Orser, Lafayette, CO (US);
Alan Rudolph, Potomac, MD (US);
Shankarrama Shivaprasad, Gaithersburg, MD (US); Renee Wegrzyn, Washington, DC (US)

(73) Assignee: Adlyfe, Inc., Rockville, MD (US)

( * ) Notice: Subject to any disclaimer, the term of this patent is extended or adjusted under 35 U.S.C. 154(b) by 1400 days.

(21) Appl. No.: 11/828,953

(22) Filed: Jul. 26, 2007

(65) Prior Publication Data

US 2008/0095706 A1    Apr. 24, 2008

Related U.S. Application Data

(60) Provisional application No. 60/833,854, filed on Jul. 28, 2006, provisional application No. 60/848,358, filed on Oct. 2, 2006.

(51) Int. Cl.
*G01N 1/00* (2006.01)
*G01N 33/53* (2006.01)

(52) U.S. Cl.
USPC ............ 435/7.21; 435/7.1; 436/501; 436/518

(58) Field of Classification Search
None
See application file for complete search history.

(56) References Cited

U.S. PATENT DOCUMENTS

| | | | |
|---|---|---|---|
| 5,721,106 A | 2/1998 | Maggio et al. | |
| 5,750,361 A * | 5/1998 | Prusiner et al. | 435/23 |
| 5,773,572 A | 6/1998 | Fishleigh et al. | |
| 5,854,204 A | 12/1998 | Findeis et al. | |
| 5,854,215 A * | 12/1998 | Findeis et al. | 514/17.8 |
| 5,891,641 A | 4/1999 | Prusiner et al. | |
| 5,977,324 A | 11/1999 | Prusiner et al. | |
| 6,166,187 A | 12/2000 | Prusiner et al. | |
| 6,214,565 B1 | 4/2001 | Prusiner et al. | |
| 6,355,610 B2 * | 3/2002 | Chesebro et al. | 514/21.7 |
| 6,399,314 B1 | 6/2002 | Krishnamurthy | |
| 6,451,541 B1 | 9/2002 | Winnacker et al. | |
| 6,498,017 B2 | 12/2002 | Riesner et al. | |
| 6,600,017 B1 | 7/2003 | Glabe et al. | |
| 6,677,125 B2 | 1/2004 | Prusiner et al. | |
| 6,750,025 B1 | 6/2004 | Hammond et al. | |
| 6,821,504 B2 | 11/2004 | Wisniewski et al. | |
| 7,125,838 B1 | 10/2006 | Stott | |
| 7,166,471 B2 | 1/2007 | Orser et al. | |
| 7,303,907 B2 | 12/2007 | Raven et al. | |
| 7,351,526 B2 | 4/2008 | Soto et al. | |
| 7,439,041 B2 | 10/2008 | Michelitsch et al. | |
| 7,691,639 B2 | 4/2010 | Orser et al. | |
| 8,062,895 B2 | 11/2011 | Orser et al. | |
| 2002/0137112 A1 | 9/2002 | Chojkier et al. | |
| 2003/0215880 A1 | 11/2003 | Burton et al. | |
| 2004/0052928 A1 | 3/2004 | Gazit | |
| 2004/0072236 A1 * | 4/2004 | Cashman et al. | 435/7.1 |
| 2004/0224365 A1 | 11/2004 | Glabe et al. | |
| 2004/0229280 A1 | 11/2004 | Hammond et al. | |
| 2005/0026165 A1 | 2/2005 | Orser et al. | |
| 2005/0112607 A1 | 5/2005 | Bamdad et al. | |
| 2005/0118645 A1 | 6/2005 | Michelitsch et al. | |
| 2005/0181998 A1 | 8/2005 | Adessi et al. | |
| 2006/0035242 A1 | 2/2006 | Michelitsch et al. | |
| 2006/0057636 A1 | 3/2006 | Heegaard et al. | |
| 2006/0057671 A1 | 3/2006 | Orser et al. | |
| 2006/0078892 A1 | 4/2006 | Hammond et al. | |
| 2006/0178302 A1 | 8/2006 | Krafft et al. | |
| 2006/0235199 A1 | 10/2006 | Mihara et al. | |
| 2006/0275910 A1 | 12/2006 | Orser et al. | |
| 2006/0286672 A1 | 12/2006 | Orser et al. | |
| 2007/0054322 A1 | 3/2007 | Gabizon | |
| 2007/0077552 A1 | 4/2007 | Hecht et al. | |
| 2008/0171341 A1 | 7/2008 | Orser et al. | |
| 2009/0061462 A1 * | 3/2009 | Michelitsch et al. | 435/7.21 |
| 2009/0238754 A1 | 9/2009 | Wegrzyn et al. | |
| 2009/0274621 A1 | 11/2009 | Wegrzyn et al. | |
| 2010/0233095 A1 | 9/2010 | Duan et al. | |
| 2010/0267151 A1 | 10/2010 | Orser et al. | |

FOREIGN PATENT DOCUMENTS

| | | |
|---|---|---|
| AU | 2007234617 A1 | 12/2007 |
| CA | 2 443 929 A1 | 10/2002 |
| JP | 2004-155688 A | 6/2004 |
| WO | WO 99/41279 A2 | 8/1999 |
| WO | WO 00/43791 A2 | 7/2000 |
| WO | WO 01/07479 A2 | 2/2001 |
| WO | WO 01/14412 A1 | 3/2001 |
| WO | WO 01/77687 A2 | 10/2001 |
| WO | WO 02/04954 A2 | 1/2002 |
| WO | WO 03/001881 A2 | 1/2003 |
| WO | WO 2006/088823 A2 | 8/2006 |

OTHER PUBLICATIONS

Lowe et al. (Book of Abstracts, 219th ACS National Meeting, San Francisco, CA Mar. 26-30, 2000 BIOT-135 Publisher: American Chemical Society, Washington, DC-Abstract Only).*
Nichols et al. (Abstracts of Papers, 226th ACS National Meeting, New York, NY United States, Sep. 7-11, 2003 BIOT-223 Publisher: American Chemical Society, Washington, DC-Abstract Only).*
Notice of Allowance issued on Oct. 26, 2009, by the Examiner in U.S. Appl. No. 10/494,906 (US 2006/0286672).
Office Action issued on Sep. 16, 2009, by the Examiner in U.S. Appl. No. 11/504,692 (US 2006-0275910).
Office Action issued on Nov. 16, 2009 by the Examiner in U.S. Appl. No. 11/030,300 (US 2006/0057671).
Office Action issued Dec. 16, 2009 by the Examiner in U.S. Appl. No. 11/979,226 (US 20008/0171341).
Tjernberg et al., "Assembling amyloid fibrils from designed structures containing a significant amyloid β-peptide fragment," *Biochem. J.*, vol. 366, pp. 343-351, 2002.

(Continued)

*Primary Examiner* — Agnieszka Boesen
(74) *Attorney, Agent, or Firm* — Foley & Lardner LLP

(57) ABSTRACT

Disclosed are agents and methods that may be used to diagnose and treat a variety of diseases associated with conformationally-altered proteins. The agents and methods may be used to identify and deliver drugs useful for treating diseases associated with conformationally-altered proteins.

9 Claims, 8 Drawing Sheets

(56) References Cited

OTHER PUBLICATIONS

Usui et al., "Peptide Arrays with Designed Secondary Structures for Protein Characterization Using Fluorescent Fingerprint Patterns," *Biopolymers (Peptide Science)*, vol. 76, pp. 129-139, 2004.
Caughey et al., "Interactions and Conversions of Prion Protein Isoforms," *Advances in Protein Chemistry*, vol. 57, pp. 139-169, Jan. 1, 2001.
Safar et al., "Thermal Stability and conformational transitions of scrapie amyloid (prion) protein correlate with infectivity," *Protein Science*, vol. 2, pp. 2206-2216, 1993.
International Search Report from PCT/US2007/016738.
U.S. Appl. No. 11/884,316, filed Feb. 14, 2006, Orser et al.
Buschmann et al., "Detection of cattle-derived BSE prions using transgenic mice overexpressing bovine PrPC", *Archives of Virology*, Supplement 16, pp. 75-86 (2000).
Chiti, F., et al., "Designing conditions for in vitro formation of amyloid protofilaments and fibrils", *Proc. Natl. Acad. Sci. USA*, vol. 96, pp. 3590-3594 (1999).
Chitnumsub et al., "The Nucleation of Monomeric Parallel Beta-Sheet-Like Structures and Their Self-Assembly in Aqueous Solution", *Biorganic & Medicinal Chemistry*, vol. 7 (1), pp. 39-59 (1999).
Fraser et al., "Conformation and Fibrillogenesis of Alzheimer A-beta Peptides with Selected Substitution of Charged Residues", *Journal of Molecular Biology*, vol. 244(1), pp. 64-73 (1994).
Grosset, A., et al., "Rapid presymptomatic detection of PrPsc via conformationally responsive palindromic PrP peptides", *Peptides, Elsevier, Amsterdam*, vol. 26, No. 1, pp. 2193-2200 (2005).
Hachiya et al., Biochemical and Biophysical Research Communications, 323:339-344 (2004).
Koclsko et al., "Cell-Free Formation of Protease-Resistant Prion Protein", *Nature*, 370:471-474 (2004).
Lu et al., "Structural Determinants for Ligand-Receptor Conformational Selection in a Peptide G Protein-coupled Receptor", *The Journal of Biological Chemistry*, 282:17921-17929 (2007).
Maxson et al., "A solid-phase assay for identification of modulators of prion protein interactions", *Analytical Biochemistry*, 323(1): 54-64 (2003).
Nguyen, J., et al., "Prion Protein Peptides Induce—Helix to—Sheet Conformational Transitions", *Biochemistry*, vol. 34, pp. 4186-4192 (1995).
Nicotera, P. "A Route for Prion Neuroinvasion," 31:345-348 (2001).
Pan, et al., "Conversion of alpha-helices into beta-sheets features in the formation of the scrapie prion proteins", *Proc. of National Academy of Science*, vol. 90, pp. 10962-10966 (1993).
Perutz, M.F., "Glutamine repeats and neurodegenerative disease: molecular aspects", *TIBS*, vol. 24, pp. 58-63 (1999).
Pillot et al., "The 118-135 Peptide of Human Prion Protein Forms Amyloid Fibrils and Induces Liposome Function", *J. Mol. Biol.*, vol. 274, pp. 381-393 (1997).
Prior, R., et al., "Selective binding of Soluble A 1-40 and A 1-42 to a Subset of Senile Plaque", *Am. J. Pathology*, vol. 148(6), pp. 1749-1756 (1996).
Prusiner, S.B., et al., "Prion Protein Biology", *Cell* 93:337-348 (1998).
Salmona, M., et al., "Molecular determinants of the physicochemical properties of a critical prion protein region comprising residues 106-126", *Biochemical Journal* 342:207-214 (1999).
Speed, M.A et al., "Specific aggregation of partially folded polypeptide chains: The molecular basis of inclusion body composition", *Nature Biotechnology* 14:1283-1287 (1996).
Speed, M.A., et al., "Polymerization Mechanism of Polypeptide Chain Aggregation", *Biotechnology and Bioengineering* 54(4):333-343 (1997).
Tcherkasskaya et al. "The Role of Hydrophobic Interactions in Amyloidogenesis: Example of Prion-Related Polypeptides", *J. of Biomolecular Structure & Dynamics*, 21(3):353-365 (2003).
Office Action dated Jul. 3, 2008, issued by the Examiner in U.S. Appl. No. 10/494,906 (12 pgs.).
Office Action dated Jan. 9, 2009, issued by the Examiner in U.S. Appl. No. 10/494,906 (8 pgs.).
Office Action dated Apr. 13, 2007, issued by the Examiner in U.S. Appl. No. 11/030,300 (14 pgs.).
Office Action dated Dec. 21, 2007, issued by the Examiner in U.S. Appl. No. 11/030,300 (9 pgs.).
Final Office Action dated Oct. 14, 2008, issued by the Examiner in U.S. Appl. No. 11/030,300 (11 pgs.).
Office Action dated Mar. 18, 2009, issued by the Examiner in U.S. Appl. No. 11/030,300 (9 pgs.).
Office Action dated Jan. 13, 2009, issued by the Examiner in U.S. Appl. No. 11/504,692 (8 pgs.).
Office Action dated Jan. 10, 2007, issued by the Examiner in U.S. Appl. No. 10/728,246 (6 pgs.).
Office Action dated Apr. 5, 2007, issued by the Examiner in U.S. Appl. No. 10/728,246 (8 pgs.).
Office Action dated Aug. 31, 2007, issued by the Examiner in U.S. Appl. No. 10/728,246 (8 pgs.).
Office Action dated Dec. 14, 2007, issued by the Examiner in U.S. Appl. No. 10/728,246 (7 pgs.).
Wurth et al., "Mutations that Reduce Aggregation of Alzheimer's Aβ42 Peptide: an Unbiased Search for the Sequence Determinants of Aβ Amyloidogenesis," *J. Mol. Biol.*, vol. 319, pp. 1279-1290, 2002.
Kim et al., "A High-Throughput Screen for Compounds That Inhibit Aggregation of the Alzheimer's Peptide," *ACS Chemical Biology*, vol. 1, No. 7, pp. 461-469, Aug. 2006.
Office Action issued on Aug. 16, 2010 by the Examiner in U.S. Appl. No. 11/030,300 (US 2006/005671).
Office Action issued on Aug. 5, 2010 by the Examiner in U.S. Appl. No. 11/979,226 (US 2008/0171341).
Office Action issued on Jul. 29, 2010 by the Examiner in U.S. Appl. No. 12/726,941 (US 2010/0267151).
Notice of Allowance issued on Jul. 21, 2011 in U.S. Appl. No. 12/726,941 (US 2010/0267151).
Office Action issued on Apr. 4, 2011 in U.S. Appl. No. 12/726,941 (US 2010/0267151).
Office Action issued on Sep. 19, 2011 in U.S. Appl. No. 11/979,226 (US 2008/0171341).
Office Action issued on Apr. 12, 2011 in U.S. Appl. No. 11/979,226 (US 2008/0171341).
European Search Report issued on Mar. 17, 2011 in application No. EP 10188900 (corresponding to US 2008/0171341).
Extended European Search Report issued on Jul. 4, 2011 in application No. EP 10188900 (corresponding to US 2008/0171341).

\* cited by examiner

Fig. 1

Transmissible spongiform encephalopathies: TSE Conformers

α - helix
Non-toxic form

β - sheet
Toxic form

Labeled peptide fragment

Fig. 2

Target: TSE protein
Unknown conformation

Receptor: Labeled Peptide fragment

β - sheet
Toxic conformation disaggregated

Catalytic propagation

Signal: Aggregates
Light scattering
Fluorescence
CD

α - helix
Non-toxic conformation

NO signal (SEQ ID NO:1)

PEPTIDE PROBES FOR DIAGNOSTICS AND THERAPEUTICS

RELATED APPLICATIONS

This application claims the benefit of priority under 35 U.S.C. §119(e) to U.S. provisional application 60/833,854, filed Jul. 28, 2006, and U.S. provisional application 60/848,358, filed Oct. 2, 2006, the entire contents of which are incorporated by reference herein in their entireties.

NIH GRANT FUNDING

Some of the inventions disclosed herein were supported by U.S. Government grants, as to which inventions the following statement applies: This invention was made with government support under grant number 5 R44 HL070399-04 awarded by the National Institutes of Health. The government has certain rights in the invention.

BACKGROUND

1. Field of the Invention

The present invention relates to the field of the detection of proteins in a specific structural form, including misfolded proteins, such as those associated with disease states, and to the treatment of those disease states. More particularly, the present invention relates to methods, probes, and kits for detecting proteins in a specific structural form in samples, such as biological and clinical samples or in vivo. In some embodiments, the proteins are associated with amyloidogenic diseases. The invention also relates to methods, agents, and kits for treating diseases associated with such proteins, and for identifying other agents useful for treating such diseases.

2. Background

A variety of diseases are associated with a specific structural form of a protein (e.g., a "misfolded protein" or a self-aggregated protein), while the protein in a different structural form (e.g., a "normal protein") is not harmful. In many cases, the normal protein is soluble, while the misfolded protein forms insoluble aggregates. Examples of such insoluble proteins include prions in transmissible spongiform encephalopathy (TSE); Aβ-peptide in amyloid plaques of Alzheimer's disease (AD), cerebral amyloid angiopathy (CAA), and cerebral vascular disease (CVD); α-synuclein deposits in Lewy bodies of Parkinson's disease, tau in neurofibrillary tangles in frontal temporal dementia and Pick's disease; superoxide dismutase in amylotrophic lateral sclerosis; and Huntingtin in Huntington's disease. See, e.g., Glenner et al., *J. Neurol. Sci.* 94:1-28, 1989; Haan et al., *Clin. Neurol. Neurosurg.* 92(4):305-310, 1990.

Often, these insoluble proteins form aggregates composed of non-branching fibrils with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions. See, e.g., Mandybur, *Acta Neuropathol.* 78:329-331, 1989; Kawai et al., *Brain Res.* 623:142-146, 1993; Martin et al., *Am. J. Pathol.* 145:1348-1381, 1994; Kalaria et al., *Neuroreport* 6:477-80, 1995; Masliah et al., *J. Neurosci.* 16:5795-5811, 1996. Other studies additionally indicate that amyloid fibrils may actually initiate neurodegeneration. See, e.g., Lendon et al., *J. Am. Med. Assoc.* 277:825-831, 1997; Yankner, *Nat. Med.* 2:850-852, 1996; Selkoe, *J. Biol. Chem.* 271:18295-18298, 1996; Hardy, *Trends Neurosci.* 20:154-159, 1997.

A. Prions & Prion-Associated Diseases

Prions are infections pathogens that cause central nervous system spongiform encephalopathies in humans and animals. Prions are distinct from bacteria, viruses, and viroids. A potential prion precursor is a protein referred to as PrP 27-30, a 28 kilodalton hydrophobic glycoprotein that polymerizes (aggregates) into rod-like filaments found as plaques in infected brains. The normal protein homologue differs from prions in that it is readily degradable, whereas prions are highly resistant to proteases. It has been suggested that prions might contain extremely small amounts of highly infectious nucleic acid, undetectable by conventional assay methods. See, e.g., Benjamin Lewin, "Genes IV", Oxford Univ. Press, New York, 1990, at page 1080. However, the predominant hypothesis at present is that no nucleic acid component is necessary for the infectivity of prion protein.

Complete prion protein-encoding genes have been cloned, sequenced, and expressed in transgenic animals. The normal cellular prion protein, $PrP^C$, is encoded by a single-copy host gene and is normally found at the outer surface of neurons. During a post-translational process, a protein referred to as $PrP^{Sc}$ is formed from the normal, cellular PrP isoform ($PrP^C$), and prion disease results. $PrP^{Sc}$ is necessary for both the transmission and pathogenesis of the transmissible neurodegenerative diseases of animals and humans.

The normal prion protein ($PrP^C$) is a cell-surface metalloglycoprotein that has mostly an α-helix and coiled-loop structure. It is believed to serve as an antioxidant and is thought to be associated with cellular homeostasis. The abnormal form ($PrP^{Sc}$) is a conformer that is resistant to proteases and has a secondary structure that contains predominantly β-sheets. It is believed that this conformational change in secondary structure leads to aggregation and eventual neurotoxic plaque deposition in the prion disease process.

Prion-associated diseases include scrapie of sheep and goats, chronic wasting disease of deer and elk, and bovine spongiform encephalopathy (BSE) of cattle. See, e.g., Wilesmith and Wells, *Microbiol. Immunol.* 172:21-38, 1991. Four prion diseases of humans have been identified: (1) kuru, (2) Creutzfeldt-Jakob disease (CJD), (3) Gerstmann-Strassler-Scheinker Disease (GSS), and (4) fatal familial insomnia (FFI). See, e.g., Gajdusek, D. C., *Science* 197:943-969, 1977; Medori et al. *N. Engl. J. Med.* 326:444-449, 1992.

Prion diseases are transmissible and insidious. For example, the long incubation times associated with prion diseases will not reveal the full extent of iatrogenic CJD for decades in thousands of people treated with cadaver-sourced human growth hormone (HGH) worldwide. The importance of detecting prions in biological products has been heightened by the possibility that bovine prions have been transmitted to humans who developed new variant Creutzfeldt-Jakob disease (nvCJD). See, e.g., Chazot et al., *Lancet* 347:1181, 1996; Will et al., *Lancet* 347:921-925, 1996.

Diseases caused by prions are hard to diagnose. The disease can be latent or subclinical (abnormal prions are detectable, but symptoms are not). Moreover, normal homologues of a prion-associated protein exist in the brains of uninfected organisms, further complicating detection. See, e.g., Ivan Roitt et al., "Immunology", Mosby-Year Book Europe Limited, 1993, at page 15.1.

Current techniques used to detect the presence of prion-related infections rely on gross morphological changes in the brain, and on immunochemical techniques that are generally applied only after symptoms are manifest. Many of the current detection methods are antibody-based assays, or rely on affinity chromatography. They use brain tissue from dead animals, or, in some cases, capillary immunoelectrophoresis of blood samples.

Brain tissue based assays can lead to late detection and required slaughtering the animal to be tested. Prionic-Check (Prionics AG), a diagnostic test for bovine spongiform encephalopathy, also entails slaughtering an animal to obtain a liquefied brain tissue sample, which is subjected to an antibody using Western Blot. Although results are obtained in six to seven hours, the test does not account for the six-month lag time between $PrP^{Sc}$ accumulation in the brain and the onset of clinical symptoms. Tonsillar biopsy sampling, and blood and cerebrospinal sampling, while accurate, can require surgical intervention and take weeks to obtain results. Electrospray ionization mass spectroscopy (ESI-MS), nuclear magnetic resonance (NMR), circular dichroism (CD), and other non-amplified structural techniques require large amounts of sample and expensive equipment that is typically located a substantial distance form the sample source. Other diseases associated with conformationally-altered proteins present similar difficulties.

B. Transmissible Spongiform Encephalopathies (TSEs)

Transmissible Spongiform Encephalopathies or "TSEs" are fatal neurodegenerative diseases that include such human disorders as CJD and kuru. Animal forms of TSE include scrapie in sheep, CWD in deer and elk, and BSE in cattle. These diseases are characterized by the formation and accumulation in the brain of an abnormal proteinase K resistant isoform (PrP-res) of a normal protease-sensitive, host-encoded prion protein (PrP-sen). PrP-res is formed from PrP-sen by a post-translational process involving conformational changes that convert the PrP-sen into a PrP-res molecular aggregate having a higher β-sheet content. The formation of these macromolecular aggregates of PrP-res is closely associated with TSE-mediated brain pathology, in which amyloid deposits of PrP-res are formed in the brain, which eventually becomes "spongiform" (filled with holes).

The cellular protein PrP-sen is a sialoglycoprotein encoded by a gene that, in humans, is located on chromosome 20. The PrP gene is expressed in both neural and non-neural tissues, with the highest concentration of its mRNA being found in neurons. The translation product of the PrP gene consists of 253 amino acids in humans, 254 amino acids in hamsters and mice, 264 amino acids in cows, and 256 amino acids in sheep (all of these sequences are disclosed in U.S. Pat. No. 5,565, 186, which describes methods of making transgenic mice that express species-specific PrP and is incorporated herein by reference). In prion protein related encephalopathies, the cellular PrP-sen is converted into the altered PrP-res. PrP-res is distinguishable from PrP-sen in that PrP-res aggregates (see, e.g., Caughey and Chesebro, *Trends Cell Biol.* 7:56-62, 1997); is at least partially resistant to proteinase K digestion (only approximately the N-terminal 67 amino acids are removed by proteinase K digestion under conditions in which PrP-sen is completely degraded) (see, e.g., Prusiner et al., *Sem. Virol.* 7:159-173, 1996); and has, as compared to PrP-sen, less α-helical structure and more β-sheet structure (see, e.g., Pan et al., *Proc. Natl. Acad. Sci. USA* 90:10962-10966, 1993).

If PrP-sen is not expressed in the brain tissue of animal recipients of scrapie-infected neurografts, no pathology occurs outside the graft, demonstrating that PrP-res and PrP-sen are both required for the pathology. See, e.g., Brander et al., *Nature* 379:339-343, 1996. The long latency period between infection and the appearance of disease (months to decades, depending on species) has prompted the development of a cell-free in vitro test, in which PrP-res induces the conversion of PrP-sen to PrP-res. See, e.g., Kockisko et al., *Nature* 370:471-474, 1994; Prusiner et al., WO 97/16728). These in vivo and in vitro observations indicated that PrP-res and PrP-sen interact to form PrP-res and promote TSE pathogenesis. The term "interact" as used herein is meant to include detectable interactions (e.g., biochemical interactions) between molecules, such as protein-protein, protein-nucleic acid, nucleic acid-nucleic acid, protein-small molecule, or nucleic acid-small molecule interactions.

Small synthetic peptides containing certain PrP sequences have previously been shown to spontaneously aggregate to form fibrils with a high degree of β-sheet secondary structure of the type seen in the insoluble deposits in TSE afflicted brains. See, e.g., Gasset et al., *Proc. Natl. Acad. Sci. USA* 89:10940-10944, 1992; Come et al., *Proc. Natl. Acad. Sci. USA* 90:5959-5963, 1993; Forloni et al., *Nature* 362:543-546, 1993; Hope et al., *Neurodegeneration* 5:1-11, 1996. Moreover, other synthetic PrP peptides have been shown to interact with PrP-sen molecules to form an aggregated complex with increased protease-resistance. See, e.g., Kaneko et al., *Proc. Natl. Acad. Sci. USA* 92:11160-11164, 1995; Kaneko et al., *J. Mol. Biol.* 270:574-586, 1997.

C. Amyloid Proteins & Associated Diseases

In AD, CAA, and CVD, the main amyloid component is the amyloid beta protein (Aβ). The Aβ protein, which is generated from the amyloid beta precursor protein (APP) by the action of two putative secretases, is present at low levels in the normal CNS and blood. Because APP can be cleaved at several site, the naturally-occurring Aβ protein is not a homogenous product. Two abundant forms found in amyloid plaques are $A\beta_{1-40}$ (also referred to as Aβ40) and $A\beta_{1-42}$ (also referred to as Aβ42), which are produced by alternative carboxy-terminal truncation of APP. See, e.g., Selkoe et al., PNAS USA 85:7341-7345, 1988; Selkoe, *Trends Neurosci.* 16:403-409, 1993. Aβ40 and Aβ42 have identical amino acid sequences, with Aβ42 having two additional residues (Ile and Ala) and its C terminus. Although Aβ40 is more abundant, Aβ42 is the more fibrillogenic and is the major component of the two in amyloid deposits of both AD and CAA. See, e.g., Wurth et al., J. Mol. Biol. 319: 1279-90 (2002).

Elevated plasma levels of Aβ42 have been associated with AD, and with increased risk for AD. Also, the magnitude of the ratio of Aβ42/Aβ40 levels has been shown to have clinical significance for AD, CAA, and other conditions, such as late-life depression (LLMD). See, e.g., Pomara et al. Neurochem. Res. (2006). Plasma levels of Aβ42 and Aβ40 are typically determined using monoclonal antibodies.

In addition to the amyloid deposits in AD cases described above, most AD cases are also associated with amyloid deposition in the vascular walls. See, e.g., Hardy, 1997, supra; Haan et al., 1990, supra; Terry et al., supra; Vinters H. V., *Cerebral amyloid angiopathy,* Stroke March-April; 18(2):311-324, 1987; Itoh Y., et al. *Subpial beta/A4 peptide deposits are closely associated with amyloid angiopathy in the elderly,* Neurosci. Lett. 155(2):144-147, Jun. 11, 1993; Yamada M., et al., *Subarachnoid haemorrhage in the elderly: a necropsy study of the association with cerebral amyloid angiopathy,* J Neurol. Neurosurg. Psychiatry 56(5):543-547, May, 1993; Greenberg S. M., et al., *The clinical spectrum of*

*cerebral amyloid angiopathy: presentations without lobar hemorrhage*, Neurology 43(10):2073-2079, October 1993. These vascular lesions are the hallmark of CAA, which can exist in the absence of AD.

Although the molecular basis of AD has not been established, the disease is associated with neurotoxic assemblies of Aβ42. Normal people have soluble Aβ protein circulating in their plasma and cerebrospinal fluid (CSF). Some in vitro studies indicate that neurotoxicity is correlated with the presence of fibrillar assemblies of Aβ42 and with the β-sheet conformation of Aβ42. Some molecules present in CSF have been reported to inhibit Aβ42 fibril formation, such as apolipoprotein E (ApoE), apolipoprotein J (ApoJ), serum amyloid P component (SAP), transthyretin (TTR), antichymostrypsin (ACT), and α2-macroglobulin (α2M), although apoE and ACT also have been reported to promote the assembly of Aβ42 into filaments in vitro. Human anti-Aβ antibodies also have been shown to block Aβ42 fibril formation and prevent Aβ42 induced neurotoxicity in vitro. See, e.g., Ono et al., Neurobiol. Disease 20: 233-40 (2005).

The mechanism of Aβ fibril formation in vitro has been explained by a nucleation-dependent model, with two phases. The first phase, nucleus formation, involves the association of monomers and is believed to be a thermodynamically unfavorable, rate-limiting step in fibril formation. The next phase, extension, involves the addition of monomers to the ends of existing fibrils, and is more thermodynamically favored. See, e.g., Ono et al., supra.

Another pathogenic form of the Aβ protein is soluble Aβ oligomers (also know as Aβ oligomeric ligands, or ADDLs). The neurotoxic activity of ADDLs has been established in several in vitro models, and human brain levels of ADDL has been found to be greatly elevated in AD patients. See, e.g., Gong et al., PNAS 100: 10417-22 (2003).

Human transthyretin (TTR) is a normal plasma protein composed of four identical, predominantly β-sheet structured units, and it serves as a transporter of the hormone thyroxin. Abnormal self assembly of TTR into amyloid fibrils causes two forms of human disease, namely senile systemic amyloidosis (SSA) and familial amyloid polyneuropathy (FAP). See, e.g., Kelly, *Curr. Opin. Struct. Biol.* 6(1): 11-17, 1996. The cause of amyloid formation in FAP is point mutations in the TTR gene; the cause of SSA is unknown. The clinical diagnosis is established histologically by detecting deposits of amyloid in situ in biopsy material.

To date, little is known about the mechanism of TTR conversion into amyloid in vivo. However, several laboratories have demonstrated that amyloid conversion can be simulated in vitro by partial denaturation of normal human TTR. See, e.g., McCutchen et al., *Biochemistry* 32(45):12119-12127, 1993; McCutchen and Kelly, *Biochem. Biophys. Res. Comm.* 197(2):415-421, 1993. The mechanism of conformational transition involves a monomeric conformational intermediate that polymerizes into linear β-sheet structured amyloid fibrils. Lai et al., *Biochemistry* 35(20):6470-6482, 1996. The process can be mitigated by binding with stabilizing molecules, such as thyroxin or triiodophenol. Miroy et al., *Proc. Natl. Acad. Sci. USA* 93(26):15051-15056, 1996.

The precise mechanism by which neuritic plaques are formed and the relationship of plaque formation to the disease-associated neurodegenerative processes are not well-defined. The amyloid fibrils in the brains of Alzheimer's and prion disease patients are known to result in the inflammatory activation of certain cells. For example, primary microglial cultures and the THP-1 monocytic cell line are stimulated by fibrillar β-amyloid and prion peptides to activate identical tyrosine kinase-dependent inflammatory signal transduction cascades. The signaling response elicited by β-amyloid and prion fibrils leads to the production of neurotoxic products, which are in part responsible for the neurodegeneration. See, e.g., Combs et al., *J. Neurosci.* 19:928-939, 1999.

Detection methods for conformationally altered proteins associated with the aforementioned disorders, such as AD, CAA, and CVD, are also inadequate in that, like the previously mentioned prion detection techniques, they often require post-mortem tissue sampling. Also, antibody-based assays may not be effective because antibodies may not distinguish the disease-causing forms of the protein from normal protein.

SUMMARY

The present invention provides methods, probes, agents and kits that may be used to diagnose and treat a variety of diseases associated with proteins in a specific structural state. The agents and methods also may be used to identify other agents useful for treating or preventing such diseases.

In accordance with one embodiment, there is provided a method for identifying a target protein present in a specific state of self-aggregation in a sample, comprising (a) contacting the sample with a peptide probe for the target protein, wherein the peptide probe preferentially binds to the target protein in a specific state of self-aggregation; and (b) detecting any binding between the peptide probe and any target protein present in the specific state of self-aggregation, thereby identifying any target protein present in the specific state of self-aggregation. In some embodiments, the peptide probe preferentially binds to the target protein in a specific state of self-aggregation selected from the group consisting of monomers, soluble oligomers, and insoluble self-aggregates. In some embodiments, the peptide probe preferentially binds to the target protein in a specific state of self-aggregation selected from the group consisting of insoluble amorphous self-aggregates, protofibrils, and fibrils.

In some embodiments, the target protein is selected from the group consisting of amyloid islet polypeptide precursor protein, amyloid beta protein or Aβ peptide, serum amyloid A, insulin, amylin, non-amyloid beta component, prions, hemoglobin, immunoglobulins or fragments thereof β$_2$-Microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.

In some embodiments, the peptide probe further comprises a detectable label. In some embodiments, the peptide probe is immobilized on a solid support.

In specific embodiments, the peptide probe comprises an amino acid sequence selected from SEQ ID NO:36 and SEQ ID NO:45.

In accordance with another embodiment, there is provided an in vivo method for identifying a target protein present in a patient in a specific state of self-aggregation, comprising (a) administering to the patient a peptide probe for the target protein, wherein the peptide probe preferentially binds to the target protein in the specific state of self-aggregation and wherein the peptide probe is labeled with a detectable label; and (b) scanning the subject for labeled peptide probe localized at target protein present in the patient, thereby identifying target protein present in the patient in the specific state of self-aggregation. In some embodiments, the peptide probe preferentially binds to the target protein in a specific state of self-aggregation selected from the group consisting of monomers, soluble oligomers, and insoluble self-aggregates.

In some embodiments, the target protein is selected from the group consisting of amyloid islet polypeptide precursor protein, amyloid beta protein or Aβ peptide, serum amyloid A, insulin, amylin, non-amyloid beta component, prions, hemoglobin, immunoglobulins or fragments thereof $\beta_2$-microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.

In accordance with another embodiment, there is provided a method for preventing the formation of protein aggregates of a target protein, comprising contacting the target protein with a peptide probe for the target protein, wherein the peptide probe preferentially binds to the target protein in a specific state of self-aggregation, thereby preventing the formation of higher order protein aggregates of the target protein. In some embodiments, the peptide probe preferentially binds to the target protein in a specific state of self-aggregation selected from the group consisting of monomers, soluble oligomers, and insoluble self-aggregates.

In some embodiments, the target protein is selected from the group consisting of amyloid islet polypeptide precursor protein, amyloid beta protein or Aβ peptide, serum amyloid A, insulin, amylin, non-amyloid beta component, prions, hemoglobin, immunoglobulins or fragments thereof $\beta_2$-Microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.

In accordance with another embodiment, there is provided a method of delivering a therapeutic agent to a target protein, comprising combining the therapeutic agent with a peptide probe for the target protein and administering the peptide probe-therapeutic agent combination to a patient in need thereof. In some embodiments, the peptide probe comprises an amino acid sequence corresponding to a region of the target protein that undergoes a conformational shift from an alpha-helical conformation to a beta-sheet conformation, and the peptide probe undergoes a conformational shift from an alpha-helical conformation to a beta-sheet conformation and the peptide probe does not comprise the full-length sequence of the target protein. In some embodiments, the peptide probe preferentially binds to the target protein in a specific state of self-aggregation, such as monomers, soluble oligomers and insoluble aggregates. In some embodiments, the therapeutic agent has anti-amyloid activity.

In accordance with another embodiment, there is provided a method of assessing an agent's ability to inhibit aggregation of a target protein, comprising (A) contacting a fusion protein and a test agent, the fusion protein comprising: (i) a peptide probe for the target protein, wherein (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and (ii) a label which generates a signal dependent on the aggregative state of the fusion protein; (B) detecting a signal generated by the label; and (C) correlating the signal with the ability of the agent to inhibit aggregation of the target protein.

In accordance with another embodiment, there is provided a method of assessing an agent's ability to inhibit aggregation of a target protein, comprising (A) contacting the target protein, a fusion protein, and a test agent, the fusion protein comprising (i) a peptide probe for the target protein, wherein (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and (ii) a label which generates a signal dependent on the aggregative state of the fusion protein; (B) detecting a signal generated by the label; and (C) correlating the signal with the ability of the agent to inhibit aggregation of the target protein.

In accordance with another embodiment, there is provided a method of assessing an agent's ability to inhibit aggregation of a target protein, comprising (A) subjecting a fusion protein to conditions that promote aggregation, the fusion protein comprising: (i) a peptide probe for the target protein, wherein (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and (ii) a label which generates a signal dependent on the aggregative state of the fusion protein; (B) detecting a first signal generated by the label; (C) subjecting the fusion protein to conditions that promote aggregation in the presence of a test agent, and detecting a second signal generated by the label; and (D) assessing the relative intensities of the first and second signals, thereby identifying an agent that inhibits aggregation of the target protein.

In accordance with another embodiment, there is provided a method of assessing an agent's ability to inhibit aggregation of a target protein, comprising (A) contacting a fusion protein and the target protein, wherein the fusion protein comprises (i) a peptide probe for the target protein, wherein (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and (ii) a label which generates a signal dependent on the aggregative state of the fusion protein; (B) detecting a first signal generated by the label; (C) contacting the fusion protein, the target protein, and a test agent, and detecting a second signal generated by the label; and (D) assessing the relative intensities of the first and second signals, thereby identifying an agent that inhibits aggregation of the target protein.

In accordance with another embodiment, there is provided a method of identifying a peptide probe for a target protein that exhibits an increased or decreased tendency to form aggregates relative to a reference peptide probe, comprising (A) detecting a first signal generated by a reference fusion protein that comprises (i) a reference peptide probe comprising (a) an amino acid sequence corresponding to a region of the target protein that undergoes a conformational shift from an alpha-helical conformation to a beta-sheet conformation, (b) wherein the peptide probe undergoes a conformational shift from an alpha-helical conformation to a beta-sheet conformation, and (c) the reference peptide probe does not comprise the full-length sequence of the target protein; and (ii) green fluorescent protein; (B) detecting a second signal generated by a test fusion protein comprising a test peptide probe and green fluorescent protein, wherein the test peptide probe is a mutant of the reference peptide probe that comprises an amino acid insertion, deletion or substitution relative to the amino acid sequence of the reference peptide probe; and (C) correlating the intensity of the second signal relative to the first signal, thereby identifying a peptide probe for a target protein that exhibits an increased or decreased tendency to form aggregates relative to the reference peptide probe.

In accordance with another embodiment, there is provided a method of identifying a peptide probe specific for a target protein in a specific structural state that falls on a spectrum of structural states ranging from a low end of soluble monomers to a high end of insoluble self-aggregates, comprising (A) subjecting a fusion protein to conditions that promote self-aggregation, the fusion protein comprising (i) a peptide probe for the target protein, wherein (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and (ii) green fluorescent protein; (B) detecting a signal generated by the fusion protein; and (C) correlating the intensity of the signal with the specificity of the peptide probe for a target protein in a specific structural state, thereby identifying a peptide probe specific for a target protein in a specific structural state.

In accordance with another embodiment, there is provided a method for treating a disease associated with a target protein, comprising contacting the target protein with a fusion protein comprising (i) a peptide probe for the target protein, wherein the peptide probe preferentially binds to the target protein, and (ii) a therapeutic agent.

BRIEF DESCRIPTION OF THE DRAWINGS

FIG. 1 illustrates the α-helical monomer and β-sheet dimer of a TSE conformer, along with various embodiments of the disclosed probes. The normal wild-type (wt) form of prion protein (PrP$^C$) prefers a monomeric state, while the abnormal, disease-causing form (PrP$^{Sc}$) prefers the multimeric (dimeric or greater) state.

FIG. 2 illustrates a diagnostic analysis of a sample containing TSE protein comprised of β-sheets. The top reaction indicates the process in the presence of a misfolded protein in a sample, while the bottom reaction indicates the process in the absence of a misfolded protein in a sample.

FIG. 11 illustrates the reactivity of a peptide probe specific for Aβ (SEQ ID NO:36) with different structural forms of Aβ40 and Aβ42.

FIG. 12 illustrates the ability of a peptide probe specific for Aβ (SEQ ID NO:36) to detect Aβ40 and Aβ42 in samples of human cerebrospinal fluid (CSF) obtained from Alzheimer's patients. The peptide probe is able to stratify Alzheimer's patients (black) from age-matched healthy patients (white) with a p value=0.0005.

FIG. 12A presents the data for each patient, while

DETAILED DESCRIPTION

Figure 3:
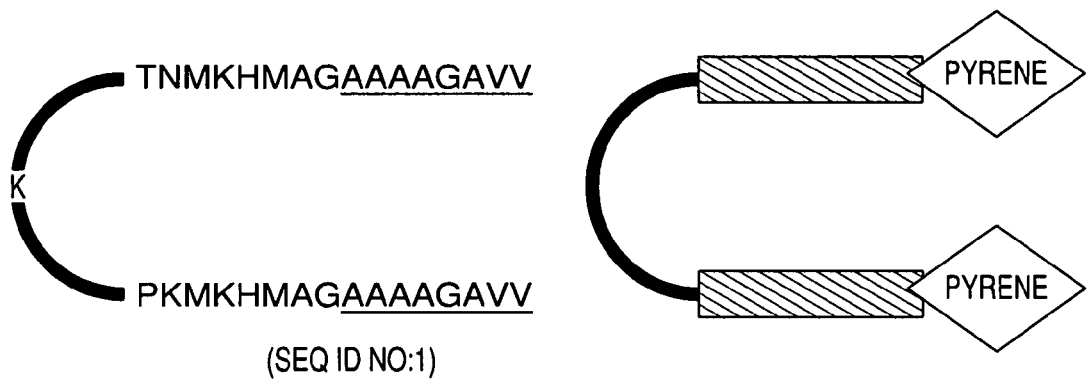
FIG. 3 illustrates a palindromic probe for prion protein.

The present invention provides probes and methods for the detection of proteins in a specific structural state, including misfolded proteins and self-aggregated proteins, such as those associated with disease states, and probes and methods for the treatment of those disease states. More particularly, the present invention provides methods, probes, and kits for detecting proteins in a specific structural state in a sample or in vivo. In some embodiments, the proteins are associated with amyloidogenic diseases. The invention also provides methods, agents, and kits for treating diseases associated with such proteins, and for identifying other agents useful for treating such diseases.

Some aspects of the invention relate to the diagnosis and treatment of diseases and conditions associated with a specific structural state of a protein, such as a specific conformation or self-aggregative state of a protein. Proteins that are associated with human disease when they adopt a specific conformational or self-aggregated state are known in the art. Examples of such diseases includes amyloidogenic diseases.

The references cited herein, including patents and patent applications, are incorporated by reference, in their entirety.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Standard reference works setting forth the general principles of recombinant DNA technology include Sambrook, J., et al. (1989) Molecular Cloning: A Laboratory Manual, 2d Ed., Cold Spring Harbor Laboratory Press, Planview, N.Y.; McPherson, M. J. Ed. (1991) Directed Mutagenesis: A Practical Approach, IRL Press, Oxford; Jones, J. (1992) Amino Acid and Peptide Synthesis, Oxford Science Publications, Oxford; Austen, B. M. and Westwood, O. M. R. (1991) Protein Targeting and Secretion, IRL Press, Oxford. Any suitable materials and/or methods known to those of ordinary skill in the art can be utilized in carrying out the present invention. However, preferred materials and methods are described. Materials, reagents and the like to which reference is made in the following description and examples are obtainable from commercial sources, unless otherwise noted.

A. DEFINITIONS

As used herein, the singular forms "a," "an," and "the" designate both the singular and the plural, unless expressly stated to designate the singular only.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the phrase "therapeutically effective amount" shall mean that drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

As described herein, "amyloidogenic diseases" are diseases in which amyloid plaques or amyloid deposits are formed in the body. Amyloid formation is found in a number of disorders, such as diabetes, AD, scrapie, BSE, CJD, chronic wasting disease (CWD), related transmissible spongiform encephalopathies (TSEs), and other diseases disclosed herein. The invention is not limited to amyloidogenic diseases, however, and is useful in the diagnosis and treatment of any disease or condition associated with a specific conformation or aggregative state of a protein.

As used herein, "protein" refers to any polymer of two or more individual amino acids (whether or not naturally occurring) linked via a peptide bond, which occurs when the carboxyl carbon atom of the carboxylic acid group bonded to the α-carbon of one amino acid (or amino acid residue) becomes covalently bound to the amino nitrogen atom of amino group bonded to the α-carbon of an adjacent amino acid. These peptide bonds, and the atoms comprising them (i.e., α-carbon atoms, carboxyl carbon atoms and their substituent oxygen atoms, and amino nitrogen atoms and their substituent hydrogen atoms) form the "polypeptide backbone" of the protein. In simplest terms, the polypeptide backbone shall be understood to refer to the amino nitrogen atoms, α-carbon atoms, and carboxyl carbon atoms of the protein, and two or more of these atoms (with or without their substituent atoms) may also be represented as a pseudoatom. Any representation of a polypeptide backbone that may be used in a functional site descriptor as described herein will be understood to be included within the meaning of the term "polypeptide backbone".

The term "protein" is understood to include the terms "polypeptide" and "peptide" (which, at times, may be used interchangeably herein) within its meaning. Proteins may include infectious proteins or "prions" as disclosed herein. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also contemplated and may be referred to herein as "proteins." Fragments may include at least 5 contiguous amino acids, at least 10 contiguous amino acids, at least 15 contiguous amino acids, at least 20 contiguous amino acids, or at least 25 contiguous amino acids of the full-length protein.

As used herein, "conformation" or "conformational constraint" refers to the presence of a particular protein conformation, for example, an α-helix, parallel and antiparallel β-strands, a leucine zipper, a zinc finger, etc. In addition, conformational constraints may include amino acid sequence information without additional structural information. As an example, "—C—X—X—C—" is a conformational constraint indicating that two cysteine residues must be separated by two other amino acid residues, the identities of each of which are irrelevant in the context of this particular constraint. A "conformational change" is a change from one conformation to another.

"Prion" is a contraction of the words "protein" and "infection". "PrP protein", "PrP", and the like are used interchangeably herein to mean both the infections particle form ("PrP$^{Sc}$") known to cause diseases (such as spongiform encephalopathies) in humans and animals, and the non-infectious form ("PrP$^{C}$") which, under appropriate conditions, is converted to the infectious PrP$^{Sc}$ form. The terms "prion", "prion protein", "PrP$^{Sc}$ protein", and the like are used interchangeably herein to refer to the infectious PrP$^{Sc}$ form of a PrP protein. Prion particles are comprised largely, if not exclusively, of PrP$^{Sc}$ molecules encoded by a PrP gene. Prions are distinct from bacteria, viruses, and viroids. Known prions infect animals and cause scrapie, a transmissible, degenerative disease of the nervous system of sheep and goats, as well BSE (or mad cow disease) and feline spongiform encephalopathy of cats. Four prion diseases known to affect humans are (1) kuru, (2) CJD, (3) GSS, and (4) FFI. As used herein, "prion" includes all forms of prions causing all or any of these diseases or others in any animals used, and in particular in humans and domesticated farm animals.

The term "PrP gene" is used herein to describe genetic material that expresses proteins that include known polymorphisms and pathogenic mutations. The term "PrP gene" refers generally to any gene of any species that encodes any form of a prion protein. The PrP gene may be from any animal, and includes all polymorphisms and mutations thereof, it being recognized that the terms include other such PrP genes that are yet to be discovered. The protein expressed by such a gene may assume either a $PrP^C$ (non-disease) or $PrP^{Sc}$ (disease) form.

The term "Aβ protein" is used herein to refer to all forms of the Aβ protein, including AB40 and AB42.

"Recombinant proteins or polypeptides" refer to proteins or polypeptides produced by recombinant DNA techniques, i.e., produced from cells, microbial or mammalian, transformed by an exogenous recombinant DNA expression construct encoding the desired protein or polypeptide. Proteins or polypeptides expressed in most bacterial cultures will typically be free of glycan. Proteins or polypeptides expressed in yeast may have a glycosylation pattern different from that expressed in mammalian cells.

"Native" or "naturally occurring" proteins or polypeptides refer to proteins or polypeptides recovered from a source occurring in nature. A native protein or polypeptide would include post-translational modifications, including, but not limited to, acetylation, carboxylation, glycosylation, phosphorylation, lipidation, acylation, and cleavage.

A DNA or polynucleotide "coding sequence" is a DNA or polynucleotide sequence that is transcribed into mRNA and translated into a polypeptide in a host cell when placed under the control of appropriate regulatory sequences. The boundaries of the coding sequence are the start codon at the 5' N-terminus and the translation stop codon at the 3'C-terminus. A coding sequence can include prokaryotic sequences, cDNA from eukaryotic mRNA, genomic DNA sequences from eukaryotic DNA, and synthetic DNA sequences. A transcription termination sequence will usually be located 3' to the coding sequence.

"DNA or polynucleotide sequence" is a heteropolymer of deoxyribonucleotides (bases adenine, guanine, thymine, cytosine). DNA or polynucleotide sequences encoding the proteins or polypeptides of this invention can be assembled from synthetic cDNA-derived DNA fragments and short oligonucleotide linkers to provide a synthetic gene that is capable of being expressed in a recombinant DNA expression vector. In discussing the structure of particular double-stranded DNA molecules, sequences may be described herein according to the normal convention of providing only the sequence in the 5' to 3' direction along the non-transcribed strand of cDNA.

"Recombinant expression vector or plasmid" is a replicable DNA vector or plasmid construct used either to amplify or to express DNA encoding the proteins or polypeptides of the present invention. An expression vector or plasmid contains DNA control sequences and a coding sequence. DNA control sequences include promoter sequences, ribosome binding sites, polyadenylation signals, transcription termination sequences, upstream regulatory domains, and enhancers. Recombinant expression systems as defined herein will express the proteins or polypeptides of the invention upon induction of the regulatory elements.

"Transformed host cells" refer to cells that have been transformed and transfected with exogenous DNA. Exogenous DNA may or may not be integrated (i.e., covalently linked) to chromosomal DNA making up the genome of the host cell. In prokaryotes and yeast, for example, the exogenous DNA may be maintained on an episomal element, such as a plasmid, or stably integrated into chromosomal DNA. With respect to eukaryotic cells, a stably transformed cell is one which is the exogenous DNA has become integrated into the chromosome. This stability is demonstrated by the ability of the eukaryotic cell lines or clones to produce via replication a population of daughter cells containing the exogenous DNA.

The terms "analog", "fragment", "derivative", and "variant", when referring to polypeptides of this invention mean analogs, fragments, derivatives, and variants of such polypeptides that retain substantially similar functional activity or substantially the same biological function or activity as the reference polypeptides, as described herein.

An "analog" includes a pro-polypeptide that includes within it, the amino acid sequence of a polypeptide of this invention.

A "fragment" is a portion of a polypeptide of the present invention that retains substantially similar functional activity or substantially the same biological function or activity as the polypeptide, as shown in in vitro assays disclosed herein.

A "derivative" includes all modifications to a polypeptide of this invention that substantially preserve the functions disclosed herein and include additional structure and attendant function, e.g., PEGylated polypeptides or albumin fused polypeptides, which have greater half-life.

A "variant" includes polypeptides having an amino acid sequence sufficiently similar to the amino acid sequence of the polypeptides of this invention. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred polypeptides of this invention. Variants include variants of polypeptides encoded by a polynucleotide that hybridizes to a polynucleotide of this invention, or a complement thereof, under stringent conditions. Such variants generally retain the functional activity of the polypeptides of this invention. Variants include polypeptides that differ in amino acid sequence due to mutagenesis.

"Substantially similar functional activity" and "substantially the same biological function or activity" each means that the degree of biological activity is within about 50% to 100% or more, within 80% to 100% or more, or within about 90% to 100% or more, of that biological activity demonstrated by the polypeptide to which it is being compared when the biological activity of each polypeptide is determined by the same procedure or assay.

"Similarity" between two polypeptides is determined by comparing the amino acid sequence of one polypeptide to the sequence of a second polypeptide. An amino acid of one polypeptide is similar to the corresponding amino acid of a second polypeptide if it is identical or a conservative amino acid substitution. Conservative substitutions include those described in Dayhoff, M. O., ed., *The Atlas of Protein Sequence and Structure* 5, National Biomedical Research Foundation, Washington, D.C. (1978), and in Argos, P. (1989) *EMBO J.* 8:779-785. For example, amino acids belonging to one of the following groups represent conservative changes or substitutions:

-Ala, Pro, Gly, Gln, Asn, Ser, Thr:
-Cys, Ser, Tyr, Thr;
-Val, Ile, Leu, Met, Ala, Phe;
-Lys, Arg, His;
-Phe, Tyr, Trp, His; and
-Asp, Glu.

"Patient," as used herein means any mammal, including humans and domesticated animals, such as cats, dogs, swine, cattle, sheep, goats, horses, rabbits, and the like. A typical patient may be at risk of a disease associated with a misfolded protein, may be suspected of suffering from such a disease, or may be desirous of determining risk or status with respect to a disease associated with a misfolded protein.

B. TARGET STRUCTURAL STATES

The exact mechanism by which the sequence of a protein directs the formation of a specific three dimensional conformation is unknown. To achieve the native conformational state, the protein molecule must adopt a unique conformation out of many alternatives. Functional proteins are typically soluble and may adopt a variety of structures including coils and ordered elements. Ordered elements include the α-helix predominant in proteins such a myoglobin and hemoglobin.

During the human aging process, some proteins exhibit a structural change from their soluble structure (comprising, for example, predominantly α-helix or random coil conformations) to more insoluble structures (comprising, for example, β-sheet conformations) that form self-aggregates associated with loss of function. Moreover, some diseases are associated with insoluble forms of proteins that are not harmful in their soluble forms.

Thus, one aspect of the present invention provides methods and probes for the detection of proteins in a specific structural state (a "target structural state"), such as a specific conformation or state of self-aggregation. A target structural state includes any three dimensional structure of a protein, including a protein's conformation and/or a protein's state of self-aggregation. Often, the target structural state is associated with a disease while a different structural state is not associated with a disease. The target structural state may cause the disease, may be a factor in a symptom of the disease, may appear in a sample or in vivo as a result of other factors, or may otherwise be associated with the disease. In one embodiment, the protein has the same amino acid sequence regardless of its structural state, and can adopt at least two different structural states, such as a disease-associated state and a non-disease-associated state.

A number of diseases are associated with proteins in a β-sheet conformation. For many of these diseases, the same proteins in an α-helix and/or random coil conformation are not associated with the disease. Thus, for these conditions, a β-sheet conformation could be a target structural state for detection of the disease, while an α-helix and/or random coil conformation could be a target structural state to confirm absence of the disease, or to identify absence of an advanced state of the disease. For example, FIG. 1 illustrates both the α-helical monomer and the β-sheet dimer forms of a TSE conformer. The normal wild-type (wt) form of prion protein (PrP$^C$) prefers a monomeric state, while the abnormal, disease-causing form (PrP$^{Sc}$) more readily takes on a multimeric state.

The following is a non-limiting list of diseases associated with specific structural protein states, followed parenthetically by the involved protein: Alzheimer's Disease (APP, Aβ peptide, α1-antichymotrypsin, tau, non-Aβ component, presenilin 1, presenilin 2, apoe); prion diseases, CJD, scrapie, and BSE (PrP$^{Sc}$); ALS (SOD and neurofilament); Pick's disease (Pick body); Parkinson's disease (α-synuclein in Lewy bodies); frontotemporal dementia (tau in fibrils); diabetes type II (amylin); multiple myeloma-plasma cell dyscrasias (IgGL-chain); familial amyloidotic polyneuropathy (transthyretin); medullary carcinoma of thyroid (procalcitonin); chronic renal failure (β$_2$-microglobulin); congestive heart failure (atrial natriuretic factor); senile cardiac and systemic amyloidosis (transthyretin); chronic inflammation (serum amyloid A); atherosclerosis (ApoA1); familial amyloidosis (gelsolin); and Huntington's disease (Huntingtin).

As discussed above, a number of diseases are associated with self-aggregated proteins, such as insoluble protein aggregates or protein fibrils. For these conditions, self-aggregated protein and/or protein fibrils could be a target structural state for detection of the disease, while soluble and/or non-aggregated protein could be a target structural state to confirm absence of the disease, or absence of an advanced stage of the disease. Many of the proteins identified in the preceding paragraph form self-aggregates and/or protein fibrils that are associated with disease states. Other such proteins include amyloid islet polypeptide precursor protein, amyloid beta protein or Aβ peptide (e.g., Aβ42 and Aβ 40), serum amyloid A, insulin (e.g., which forms insulin-related amyloid), amylin, non-amyloid beta component, prions, hemoglobin (e.g. sickle cell anemia variant), immunoglobulins or fragments thereof (e.g., IgG L-chain), β$_2$-microglobulin, α-synuclein, rhodopsin, α1-antichymotrypsin, cystallins, tau, p53, presenilins (e.g., presenilin 1 and presenilin 2), low-density lipoprotein receptor, apolipoproteins (e.g., apoA and apo E), superoxide dismutase, neurofilament proteins, transthyretin, procalcitonin or calcitonin, atrial natriuretic factor, gelsolin, cystic fibrosis transmembrane regulator, Huntington's disease protein (i.e., Huntingtin), fibrinogen alpha-chain, phenylalanine hydroxylase, collagen, beta-hexosaminidase, and cystatin C protein. Insoluble proteins generally exhibit β-sheet formation in the aggregate.

For AD, the Aβ 40 or Aβ42 protein could be a target protein, and any of their states could be a target structural state, such as a state of self-aggregation such as soluble monomers, soluble oligomers, aggregates/ADDLs, insoluble amorphous aggregates, protofibrils, and fibrils. Current thinking on the significance of these different structural states with risk of disease, diagnosis of disease, and disease progression and etiology is reviewed in the background section above.

For prion proteins, the PrP$^{Sc}$ form of the PrP protein could be a target structural state for detection of the disease, while the PrP$^C$ form of the PrP protein could be a target structural state to confirm absence of the disease, or absence of an advanced stage of the disease. Additionally, self-aggregates of the PrP$^{Sc}$ form could be a target structural state for detection of the disease. For example, the most infective form of PrP$^{Sc}$ may be a small soluble aggregate, rather than the mature fibrils formed in the brain in late stages of the disease. See, e.g., Silveira et al., Nature 437: 257-61 (1005) (identifying PrP$^{Sc}$ particles with an approximate molecular weight of 300-600 kDa and a roughly spherical to elliptical shape with a diameter of 17-27 nm as having the highest infectivity and converting activity). Thus, this soluble aggregate form of PrP$^{Sc}$ could be a target structural state.

C. PEPTIDE PROBES

One aspect of the invention relates to peptide probes useful for detecting a specific structural state of a target protein in a sample or in vivo, i.e., useful for detecting protein in a target structural state. Typically, the peptide probe includes an amino acid sequence corresponding to a region of the target protein which undergoes a conformational shift from an alpha-helical conformation to a beta-sheet conformation, and the peptide probe itself undergoes a conformational shift from an alpha-helical conformation to a beta-sheet conformation. For example, the peptide probe may undergo a conformational shift when contacted with a target protein that is in the beta-sheet conformation. As discussed in more detail below, in some embodiments the peptide probes also are useful for identifying therapeutic agents and as therapeutic agents themselves.

1. Homology

In one embodiment, the probe comprises an amino acid sequence that is homologous or identical to a target protein, or to a region of the target protein. "Homology", "homologs of", "homologous", "identity", or "similarity" refers to sequence similarity between two polypeptides, with identity being a more strict comparison. Homology and identity may each be determined by comparing a position in each sequence that may be aligned for purposes of comparison. When a position in the compared sequence is occupied by the same amino acid, then the molecules are identical at that position. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares 10% or less identity, with one of the sequences described herein. Related sequences share more than 10% sequence identity, such as at least about 15% sequence identity, at least about 20% sequence identity, at least about 30% sequence identity, at least about 40% sequence identity, at least about 50% sequence identity, at least about 60% sequence identity, at least about 70% sequence identity, at least about 80% sequence identity, at least about 90% sequence identity, at least about 95% sequence identity, or at least about 99% sequence identity.

The term "percent identity" refers to sequence identity between two amino acid sequences. Identity may be determined by comparing a position in each sequence that is aligned for purposes of comparison. When an equivalent position in one compared sequences is occupied by the same amino acid in the other at the same position, then the molecules are identical at that position; when the equivalent site occupied by the same or a similar amino acid residue (e.g., similar in stearic and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as part of the GCG sequence analysis package (University of Wisconsin, Madison, Wis.), and may be used with, e.g., default settings. ENTREZ is available through the National Center for Biotechnology Information, National Library of Medicine, NIH, Bethesda, Md.). In one embodiment, the percent identity of two sequences may be determined by the GCG program with a gap weight of 1, e.g., each amino acid gap is weighted as if it were a single amino acid mismatch between the two sequences. Other techniques for determining sequence identity are well known and described in the art.

The term "homolog of an insoluble protein" includes all amino acid sequences that are encoded by a homolog of an insoluble protein gene, and all amino acid sequences that are equivalent or homologous to such sequence. Therefore, "homolog of an insoluble protein" includes proteins that are scored as hits in the Pfam family. To the identify the presence of an "insoluble protein" domain in a protein sequence, and make the determination that a polypeptide or protein of interest has a particular profile, the amino acid sequence of the protein may be searched against one of several databases (SwissProt, PIR, for example) using various default parameters. For example, the hmmsf program, which is available as part of the HM_MER package of search programs, is a family-specific default program for MILPAT0063 and a score of 15 is the default threshold score for determining a hit. Alternatively, the threshold score for determining a hit may be lowered (e.g., to 8 bits). A description of the Pfam database may be found in Sonham et al., *Proteins* 28(3):405-420, 1997, and a detailed description of HMMs may be found, for example, in Gribskov et al., *Meth. Enzymol.* 183:146-159, 1990; Gribskov et al., *Proc. Natl. Acad. Sci. USA* 84:4355-4358, 1987; Krogh et al., *J. Mol. Biol.* 234:1501-1531, 1994; and Stultz et al., *Protein Sci.* 2:305-314, 1993, the contents of which are incorporated herein by reference.

2. Probe Design

The probes disclosed herein may be used to detect protein present in a specific structural state in a sample or in vivo, e.g., a target structural state. In one embodiment, the probes comprise amino acid sequences that are based on (e.g., homologous or identical to) at least a region of the amino acid sequence of the target protein. Such probes also are referred to as "corresponding" to a region of the amino acid sequence of the target protein. Thus, the amino acid sequence of the probe may be designed from the target protein based on existing information in sequence databases or, alternatively, may be readily determined experimentally. While the probe may comprise a sequence based on any region of the target protein, in one embodiment, the sequence is based on a region of the target protein that is involved in the target structural state. For example, in one embodiment, the probes comprise amino acid sequences that are similar to (e.g., homologous to), or identical to, a region of the amino acid sequence of the target protein that undergoes a structural shift, such as a shift from an α-helix/random coil conformation to a β-sheet conformation.

A probe may comprise a minimum number of contiguous amino acids from the target protein, such as at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 contiguous amino acids from the target protein sequence, or any range between these numbers, such as about 10 to about 25 contiguous amino acids from the target protein sequence.

The probes themselves may be at least about 5 amino acids units in length and may be up to about 300-about 400 amino acid units in length (-mer) or more, or any size in between the range of about 5 up to about 400 amino acids, such as about 10 amino acids to about 50 amino acids in length. In some embodiments, probes are about 15 amino acids in length to about 100 amino acids in length. In other embodiments, probes range from about 20 amino acids in length to about 40 amino acids in length. In further embodiments, probes range from about 17 amino acids in length to about 34 amino acids in length. The length of a given probe may influence the probe's ability to complex and produce β-sheet formation with the target protein, and can be selected by the skilled artisan guided by the teachings herein.

The invention also includes probes comprising amino acid sequences based on about 5 or more contiguous residues of the amino acid sequence of the target protein, with one or more residues added, deleted, or substituted by methods known in the art.

In one embodiment, the probes undergo a structural change similar to that of the target protein and, for example, may exist in either an α-helix/random coil conformation or a β-sheet conformation. In one specific embodiment, the probes exist in an α-helix/random coil conformation in solution, and undergo a conformational change to a β-sheet conformation when contacted with target protein in a β-sheet conformation. For example, in one embodiment, the probe comprises a peptide or peptidomimetic of at least five, or ten, or more, amino acid residues that exhibit a random coil or α-helical conformation in solution. A peptide or peptidomimetic probe solvent may be aqueous and have a pH of between about 4 and about 10, such as between about 5 and about 8, and may have an ionic strength of between about 0.05 and about 0.5 (when typically prepared with a chloride salt, such as sodium chloride or potassium chloride). The solvent may also comprise a percentage of a water-miscible organic material, such as trifluoroethanol in amounts between about 30% to about 70% by volume, such as between about 45% to about 60%. The solvent may be prepared with a suitable buffering system such as acetate/acetic acid, Tris, or phosphate.

Probes may be designed under the following constraints. Only a few kcal difference separate a population of a probe in an initial conformation state (e.g., alpha-helix) from a population the probe predominantly in the transformed conformational state (e.g., beta-sheet). The transformation from one conformational state to the other is provided by the driving force due either to the Kd of association between the probe molecule and its natural associate to form β-sheet complex, or to changes in the electrostatic interactions between the molecules (for example, changes caused by lowering the ionic strength of the solution). If metal ions, such as Al, or the binding of another ligand are involved, other electrostatic or stearic effects could contribute. The size of the probe peptide may vary, but should be of sufficient length to have "reasonably" well defined secondary structure under detection conditions and to have sufficient recognitional specificity for the target selected, such as a prion protein. The probe peptide should also accommodate single-site mutations to be generally applicable to mutated proteins or strains, recognizing that these changes and/or heterogeneities affect the thermodynamic stability of the molecule. Moreover, the probe must be non-contagious to the patient population, whether that population is a human patient population, a domesticated animal population, or other mammalian population.

In one embodiment, a probe has a palindromic structure with two amino acid sequences corresponding to the amino sequence of the target protein. The term "palindromic" refers to the organization of a given probe sequence such that it comprises first and second peptide sequences corresponding to a portion of the target protein involved in the structural shift, which peptide sequences are presented in a palindromic manner, i.e., from the carboxy end to the amino end (or amino end to carboxy end) in the first peptide sequence, and from the amino end to the carboxy end (or carboxy end to amino end) in the second peptide sequence. The first and second peptide sequences in the palindromic probe do not have to be identical in length. In some embodiments, the first and second peptide sequences are at least roughly equivalent in length. In some embodiments, the first and second peptide sequences comprise the same amino acid sequence. In some embodiments, the two peptide sequences (the "arms" of the palindromic probe) are not more than 15, not more than 10, or not more than 5 amino acids in length. In other embodiments, each arm comprises from about 10 to about 25 amino acids, such as from about 14 to about 20 amino acids. In some embodiments, the first and second peptide sequences within a palindromic probe are separated by a linker, such as a peptide linker comprising between about 1 and about 5 amino acids, or between about 1 and about 3 amino acids, and which may comprise at least one proline amino acid, or may comprise primarily proline amino acids. Suitable peptide probes are described in U.S. 2006-057671, which is incorporated herein by reference in its entirety. FIG. 3 presents an exemplary palindromic 33-mer probe. Palindromic probes may be particularly useful for detecting prion proteins.

In some embodiments, probes may comprise a hydrophobic amino acid sequence that is based on portion of the amino acid sequence of the target protein (such as the portion of the target amino acid sequence that undergoes a structural shift), that may vary in length from about 1 amino acid to about 20 or more amino acids, such as about 2-about 10 amino acids in length, and that appears at or near one of the two ends of the probe. In the case of palindromic probes, hydrophobic amino acid sequences may appear at the ends of each the two peptide arms of the probe. Optionally, the probe also may include a synthetic hydrophobic amino acid sequence (i.e., not natural to the peptide sequence of the target protein) at least one end of the probe and, in the case of palindromic probes, at or near one or both ends of the probe, which may vary in length from as few as about 1 amino acid to about 20 or more amino acids, such as about 2-about 10 amino acids in length. Probes may include N-terminal amino acids residues, C-terminal amino acids residues, or both, which are suitable for use in linking a label to the probe (e.g., Lys, which includes a free amino group).

By way of example and without limitation, if a desired peptide sequence in a target protein comprises the sequence, reading from amino end to carboxy end, QRSTVVARLKAAAV (SEQ ID NO:15) (where AAAV (SEQ ID NO:30) is a hydrophobic amino acid sequence) then the palindrome may comprise a first peptide sequence which is VAAAKLRAVVTSRQ (SEQ ID NO:31) and a second peptide sequence which is QRSTVVARLKAAAV (SEQ ID NO:15) (or a close variation to that sequence), with the two sequences separated by a linker comprising from about 1 to about 5 amino acids, with at least one of those amino acids, and preferably most, if not all, of those amino acids, being proline amino acids. A suitable probe for this target protein therefore could be: VAAAKLRAVVTSRQPPPPQRSTVVARLKAAAV (SEQ ID NO:28) (hypothetical palindromic probe).

A probe may be specific for any target protein. For example, the target protein may be a prion protein, such as PrP$^C$, PrP$^{Sc}$, or a mixture thereof. Accordingly, the target protein may include a protein of SEQ ID NO:13 (Human Prion Protein, Accession PO4156) or a fragment thereof. In some embodiments, a "fragment thereof" may include at least about 5 contiguous amino acids up to the full length of the polypeptide sequence, or any number of contiguous amino acids in between the range of about 5 up to the full length protein. In some embodiments, the probe comprises the full length protein; in other embodiments the probe does not comprise the full length protein. In some embodiments, the probe can be at least about 10 contiguous amino acids, or at least about 15 amino acids of the full-length sequence, or may include a sequence with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to those contiguous residues.

A target protein also may be an amyloid beta protein, such as Aβ42 (SEQ ID NO:32) or Aβ 40 (SEQ ID NO:4). A peptide probe of the fusion protein may include a sequence having at least about 15% sequence identity to SEQ ID NO:32 or SEQ ID NO:4, or fragments thereof. For example, the peptide probe may include at least about 5 contiguous amino acids up to the full length of the protein (SEQ ID NO:32 or SEQ ID NO:4), or any number of contiguous amino acids from SEQ ID NO:32 or SEQ ID NO:4 in between these size ranges. In other embodiments of the invention, the probe can be at least about 10 or at least about 15 contiguous amino acid residues of SEQ ID NO:32 or SEQ ID NO:4, or may include a sequence with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to those contiguous residues.

In some embodiments, the peptide probe may include mutations in Aβ42 (SEQ ID NO:32) or Aβ 40 (SEQ ID NO:4) as disclosed in the art (Wurth et al., J. Molec. Biol. 319:1279-1290 (2002); Kim et al., J. Biol. Chem. 41:35069-35076 (2005), which are incorporated herein by reference in their entireties). In some embodiments, the peptide probe is specific for one of Aβ42 or Aβ40. That is, the probe preferentially binds to one of Aβ42 or Aβ 40 and thus is useful for distinguishing samples comprising Aβ42 from those comprising Aβ40, or for qualitatively assessing the relative amounts of Aβ42 and Aβ 40 in a sample, or for quantitating the amount(s) of Aβ42 and/or Aβ 40 in a sample. Such peptide probes can be used in similar in vivo methods, to detect and/or distinguish Aβ42 and Aβ 40 in vivo.

A target protein also may be amyloid islet polypeptide precursor protein. The peptide probe for such a target protein may include SEQ ID NO:11, a sequence having at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:11, or fragments thereof. For example, the peptide probe of the fusion protein may comprise at least about 5 contiguous amino acid residues up to the full length of SEQ ID NO:11, or any number of contiguous amino acids between these two ranges. In other embodiments of the invention, the peptide probe of the fusion protein may comprise at least about 10 or at least about 15 contiguous amino acid residues of SEQ ID NO:11, or may comprise a sequence with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to those contiguous residues.

A target protein also may be transthyretin protein. A peptide probe for such a target protein may include SEQ ID NO:26, a sequence having at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:26, or fragments thereof. For example, the peptide probe of the fusion protein may comprise at least about 5 contiguous amino acid residues up to the full length of SEQ ID NO:26, or any number of contiguous amino acids in between these two ranges. In other embodiments of the invention, the peptide probe may comprise at least about 10 or at least about 15 contiguous amino acid residues of SEQ ID NO:26 or at least about 5 or at least about 10 amino acids of amino acid residues 11-19 of SEQ ID NO:26, or may include a sequence with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to those contiguous residues.

A target protein also may be cystatin C protein. A peptide probe for such a target protein may include SEQ ID NO:17, a sequence having at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:17, or fragments thereof. For example, the peptide probe of the fusion protein may comprise at least about 5 contiguous amino acid residues up to the full length of SEQ ID NO:17, or any number of contiguous amino acids in between these two ranges. In other embodiments of the invention, the peptide probe comprises at least about 10 or at least about 15 contiguous amino acid residues of SEQ ID NO:17, or the peptide probe may comprise a sequence with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to those contiguous residues.

A target protein may be Huntington's disease protein or "Huntingtin." A peptide probe for such a target protein may include SEQ ID NO:19, a sequence having at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:19, or fragments thereof. For example, the peptide probe of the fusion protein may comprise at least about 5 contiguous amino acid residues up to the full length of SEQ ID NO:19, or any number of contiguous amino acids in between these two ranges. In other embodiments of the invention, the peptide probe comprises at least about 10 or at least about 15 contiguous amino acid residues of SEQ ID NO:19, or may include a sequence with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to those contiguous residues.

A peptide probe may have an amino acid sequence that is equivalent to the amino acid sequence of a target protein, or fragment thereof. "Equivalent" refers to a protein having an amino acid sequence that is similar to the amino acid sequence of the protein to be analyzed. In some embodiments, an "equivalent" has at least one, but fewer than about 5 (e.g., 3 or fewer) differences in the amino acid sequence, such as by way of substitutions, additions, or deletions. In other embodiments, an "equivalent" has at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the target protein sequence or fragment thereof. The substitution of one or more amino acids in a given sequence that does not substantially change the basic function of the probe. In some embodiments, an "equivalent" may include one or more "conservative amino acid substitutions" which are substitution in which the amino acid residue is replaced with an amino acid residue having a similar side chain. Families of amino acid residues having similar side chains include those with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

3. Synthesis

Peptide probes may be synthesized chemically or by using recombinant DNA methodology.

For example, a peptide probe may be synthesized chemically by performing various solid-phase techniques (Roberge et al., Science 269:202 204 (1995)) and automated synthesis may be achieved, for example, using peptide synthesizers known in the art (e.g., ABI 431A Peptide Synthesizer, Perkin Elmer, Palo Alto, Calif.). A newly synthesized peptide may be substantially purified by preparative high performance liquid chromatography (e.g., Creighton, Proteins, Structures and Molecular Principles (1983)) or other comparable techniques available in the art. The composition of the synthetic peptides may be confirmed by amino acid analysis or sequencing (e.g., the Edman degradation procedure). A label or reporter may be chemically coupled to the synthesized peptide probe, as discussed in more detail below.

To express a desired polypeptide in a host cell, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

To express a peptide probe in a host cell, a procedure such as the following can be used. A restriction fragment containing a DNA sequence that encodes the peptide probe may be cloned into an appropriate recombinant plasmid containing an origin of replication that functions in the host cell and an appropriate selectable marker. The plasmid may include a promoter for inducible expression of the peptide probe (e.g., pTrc (Amann et al., (1988) Gene 69:301 315) and pET11d (Studier et al., Gene Expression Technology: Methods in Enzymology 185, Academic Press, San Diego, Calif. (1990) 60 89)).) The recombinant plasmid may be introduced into the host cell by, for example, electroporation and cells containing the recombinant plasmid may be identified by selection for the marker on the plasmid. Expression of the peptide probe may be induced and detected in the host cell using an assay specific for the peptide probe.

A suitable host cell for expression of a peptide probe may be any prokaryotic or eukaryotic cell (e.g., bacterial cells such as *E. coli* or *B. subtilis*, insect cells (baculovirus), yeast, or mammalian cells such as Chinese hamster ovary cell (CHO)). In some embodiments, the DNA that encodes the peptide may be optimized for expression in the host cell. For example, the DNA may include codons for one or more amino acids that are predominant in the host cell relative to other codons for the same amino acid.

4. Exemplary Probes

Alpha-helix or random coil probes (i.e., probes that exhibit α-helix or random coil conformation in solution) useful in the disclosed methods may include the following:

a. PrP Probes

A palindromic 33-mer comprising amino acid sequences that are identical to amino acids 122-104 and 109-122 of the PrP$^{Sc}$ protein (SEQ ID NO:13 and 14) (SwissProt P04156; Pfam ID Prion Pf00377 & 03991): VVAGAAAAGAVH-KLNTKPKLKHVAGAAAAGAVV (SEQ ID NO:29) (murine); VVAGAAAAGAMHKMNTKPKMKHMA-GAAAAGAVV (SEQ ID NO:1) (human). In some embodiments, a C-terminal lysine may be added to the palindromic 33-mer to form a 34-mer (e.g., VVAGAAAAGAM- HKMNTKPKMKHMAGAAAAGAVVK (SEQ ID NO:33) and VVAGAAAAGAVHKLNTKPKLKHVA-GAAAAGAVVK (SEQ ID NO:34)). The C-terminal lysine may be suitable for use in linking the probe to a suitable label (e.g., pyrene).

A palindromic 33-mer comprising amino acid sequences that are equivalent to amino acids 122-104 and 109-122 of the PrP$^{Sc}$ protein (SEQ ID NO:13 and 14) (SwissProt P04156; Pfam ID Prion Pf00377 & 03991).

A palindromic 33-mer comprising amino acid sequences that are between about 70% to about 90% identical to amino acids 122-104 and 109-122 of the $PrP^{Sc}$ protein (SEQ ID NO:13 and 14) (SwissProt P04156; Pfam ID Prion Pf00377 & 03991).

A probe comprising amino acid sequences that include at least 10 contiguous amino acid residues of amino acids 104-122 of the human $PrP^{Sc}$ or amino acids 103-121 of the murine $PrP^{Sc}$ protein (SEQ ID NO:13 and 14) (SwissProt P04156; Pfam ID prion PF00377 & 03991) Human Prion Protein (Accession PO4156).

A probe comprising the amino acid sequence KPKT-NMKHMAGAAAAGAVV (SEQ ID NO:39).

A palindromic 33-mer comprising the amino acid sequence VVAGAAAAGAMHKM NTKPKMKHMAGAAAAGAVV (SEQ ID NO:40) (linker sequence for the two arms of the palindrome underlined).

A palindromic 33-mer comprising the amino acid sequence VVAGAAAAGAMHKM KPKTNMKHMAGAAAAGAVV (SEQ ID NO:41) (linker sequence for the two arms of the palindrome underlined).

A palindromic 33-mer comprising the amino acid sequence VVAGAAAAGAVHKM KPKTNMKHVAGAAAAGAVV (SEQ ID NO:42) (linker sequence for the two arms of the palindrome underlined).

b. Aβ Probes

A probe comprising amino acid sequences that are identical to amino acids 1-40 of the Aβpeptide (Nref00111747; human): DAEFRHDSGYEVHHQKLVFFAEDVGSNK-GAIIGLMVGGVV (SEQ ID NO:4).

A probe comprising amino acid sequences that are equivalent to amino acids 1-40 of the Aβ peptide (Nref00111747; human) (SEQ ID NO:4).

A probe comprising amino acid sequences that are between about 70% to about 90% identical to amino acids 1-40 of the Aβ peptide (Nref00111747; human) (SEQ ID NO:4).

A probe comprising amino acid sequences that are identical to amino acids 11-34 of the Aβ peptide (Nref00111747; human): EVHHQKLVFFAEDVGSNKGAIIGL (SEQ ID NO:5).

A probe comprising amino acid sequences that are identical to amino acids 11-34 of the Aβ peptide (Nref00111747; human), but with residue H113 substituted with R to reduce metal ion interactions and to increase the solubility of the peptide: EVRHQKLVFFAEDVGSNKGAIIGL (SEQ ID NO:6).

A probe comprising amino acid sequences that are identical to amino acids 25-35 of the Aβ peptide (Nref0011747; human): GSNKGAIIGLM (SEQ ID NO:7).

A probe comprising amino acid sequences that are identical to amino acids 17-35 of the Aβ peptide (Nref0011747; human): LVFFAEDVGSNKGAIIGLM (SEQ ID NO:35). Optionally, the probe may include an additional N-terminal lysine (K) KLVFFAEDVGSNKGAIIGLM (SEQ ID NO:36), a C-terminal lysine (K) LVFFAEDVGSNKGAIIGLMK (SEQ ID NO:37), or both KLVFFAEDVGSNKGAIIGLMK (SEQ ID NO:38).

c. TSE Probes

A probe comprising amino acid sequences that are homologous to amino acids 104-122 or wild-type (wt) TSE (human Nref00130350): KPKTNLKHVAGAAAAGAVV (SEQ ID NO:10).

A probe comprising amino acid sequences that are equivalent to amino acids 104-122 of wild-type (wt) TSE (human Nref00130350) (SEQ ID NO:10).

A probe comprising amino acid sequences that are between about 70% to about 90% identical to amino acid sequences 104-122 of wild-type (wt) TSE (human Nref00130350) (SEQ ID NO:10).

A probe that comprises an amino acid sequence that: (a) is a selectively mutated TSE sequence; (b) is destabilized and non-infectious; and (c) has an amino acid sequence that is homologous to amino acid sequences 104-122 or wild-type (wt) TSE (human Nref00130350) (SEQ ID NO:10).

A probe that comprises an amino acid sequence that: (a) is a selectively mutated TSE sequence; (b) is destabilized and non-infectious; and (c) has an amino acid sequence that is equivalent to amino acid sequences 104-122 or wild-type (wt) TSE (human Nref00130350) (SEQ ID NO:10).

A probe that comprises an amino acid sequence that: (a) is a selectively mutated TSE sequence; (b) is destabilized and non-infectious; and (c) has an amino acid sequence that is between about 70% and about 90% identical to amino acid sequences 104-122 or wild-type (wt) TSE (human Nref00130350) (SEQ ID NO:10).

d. Amylin Probes

A probe comprising amino acid sequences that are identical to amino acids 1-38 of the human islet amyloid polypeptide precursor (amylin) protein (Accession # NP.sub.—000406; human) implicated in human diabetes: MGILKLQVFLIVLSVALNHLKAT-PIESHQVEKRKCNTA (SEQ ID NO:11).

A probe comprising amino acid sequences that are identical to at least 10 contiguous amino acid residues within the sequence corresponding to amino acids 1-38 of the human islet amyloid polypeptide precursor (amylin) protein (Accession # NP__00406; human) (SEQ ID NO:11).

e. Other Probes

A probe that has a helix-loop-helix conformation found in polylysine and an amino acid sequence that is at least 10 amino acid residues in length and is equivalent or homologous to KKKKKKKKKKKKKKKKKKKKKKKKKKK (27-mer) (SEQ ID NO:8).

A probe that has a conformation found in polyglutamine and an amino acid sequence that is equivalent or homologous to QQQQQQQQQQQQQQQQQQQQQQQ (23-mer) (SEQ ID NO:9).

A probe comprising amino acid sequences that are identical to amino acids 1-25 of the human lung surfactant protein (NCBI Accession # AAH32785; human) implicated in human infant SIDS: MAESHLLQWLLLLLPTLCGPGTAAW (SEQ ID NO:12)

A probe comprising amino acid sequences which include at least 10 contiguous amino acid residues of amino acids 235-269 (emphasized below by double underlining) of the human plasma gelsolin (P06396; Muary et al., *FEBS Lett.* 260(1):85-87, 1990):

```
                                          (SEQ ID NO: 16)
MAPHRPAPALLCALSLALCALSLPVRAATASRGASQAGAPQGRVPEARPN

SMVVEHPEFLKAGKEPGLQIWRVEKFDLVPVPTNLYGDFFTGDAYVILKT
```

-continued
VQLRNGNLQYDLHYWLGNECSQDESGAAAIFTVQLDDYLNGRAVQHREVQ

GFESATFLGYFKSGLKYKKGGVASGFKHVVPNEVVVQRLFQVKGRRVVRA

TEVPVSWESFNNGDCFILDLGNNIHQWCGSNSNRYERLKATQVSKGIRDN

ERSGRARVHVSEEGTEPEAMLQVLGPKPALPAGTEDTAKEDAANRKLAKL

YKVSNGAGTMSVSLVADENPFAQGALKSEDCFILDHGKDGKIFVWKGKQA

NTEERKAALKTASDFITKMDYPKQTQVSVLPEGGETPLFKQFFKNWRDPD

QTDGLGLSYLSSHIANVERVPFDAATLHTSTAMAAQHGMDDDGTGQKQIW

RIEGSNKVPVDPATYGQFYGGDSYIILYNYRHGGRQGQIIYNWQGAQSTQ

DEVAASAILTAQLDEELGGTPVQSRVVQGKEPAHLMSLFGGKPMIIYKGG

TSREGGQTAPASTRLFQVRANSAGATRAVEVLPKAGALNSNDAFVLKTPS

AAYLWVGTGASEAEKTGAQELLRVLRAQPVQVAEGSEPDGFWEALGGKAA

YRTSPRLKDKKMDAHPPRLFACSNKIGRFVIEEVPGELMQEDLATDDVML

LDTWDQVFVWVGKDSQEEEKTEALTSAKRYIETDPANRDRRTPITVVKQG

FEPPSFVGWFLGWDDDYWSVDPLDRAMAELAAYERLKATQVSKGIRDNER

SGRARVHVSEEGTEPEAM.

A probe comprising amino acid sequences that include at least 10 contiguous amino acid residues of the amyloid forming region (amino acids 26-147; emphasized by double underlining below) of the cystatin C protein sequence, as depicted below and reported by Levy et al., *J. Exp. Med.* 169(5):1771-1778, 1989 (P01034). An appropriate probe is any portion thereof of at least 10 amino acids. Numerous probes may be positioned accordingly.

(SEQ ID NO: 17)
MAGPLRAPLLLLAILAVALAVSPAAGSSPGKPPRLVGGPMDASVEEEGVR

RALDFAVGEYNKASNDMYHSRALQVVRARQIVAGVNYFLDVELGRTTCTK

TQPNLDNCPFHDQPHLKRKAFCSFQIYAVPWQGTMTLSKSTCQDA.

A palindromic probe of the cystatin C protein taken from amino acids 39-47 of the above sequence, with a four unit proline linker; such as EEEVSADMPPPPMDASVEEE (SEQ ID NO:18)

A probe comprising amino acid sequences that include between 10 and 23, inclusive, contiguous glutamine resides of oligo or polyglutamine from residues 18-40 (emphasized by double underlining below) of the Huntingtin protein (Huntington's disease protein) protein sequence depicted below:

(SEQ ID NO: 19)
MATLEKLMKAFESLKSFQQQQQQQQQQQQQQQQQQQQQQPPPPPPPPPP

PQLPQPPPQAQPLLPQPQPPPPPPPPPGPAVAEEPLHRPKKQELSATKK

DRVNHCLTICENIVAQSVRNSPEFQKLLGIMELFLLCSDDAESDVRMVAD

ECLNKVIKALMDSNLPRLQLELYKEIKKNGAPRSLRAALWRFAELAHLVR

PQKCRPYLVNLLPCLTRTSKRPEESVQETLAAAVPKIMASFGNFANDNEI

KVLLKAFIANLKSSSPTIRRTAAGSAVSICQHSRRTQYFYSWLLNVLLGL

LVPVEDEHSTLLILG (P42858; gi:1170192).

An exemplary probe: QQQQQQQQQQQQQQQQQQQQ (SEQ ID NO:20).

A probe comprising amino acid sequences that include at least 6 contiguous amino acid residues of amino acid residues 45-50 and 48-53 (emphasized below) of the human islet amyloid polypeptide involved in fibrillogenesis, sequence depicted below, NP.sub.—000406 [gi:4557655] Scrocchi et al., *J Struct. Biol.* 141(3):218-227, 2003:

(SEQ ID NO: 21)
MGILKLQVFLIVLSVALNHLKATPIESHQVEKRKCNTATCATQRLANFLV

HSSNNFGAILSSTNVGSNTYGKRNAVEVLKREPLNYLLPL.

Exemplary probes may contain the following sequences, which are sequences within the sequence 45-53 of the above peptide sequence of SEQ ID NO:21, which may be used without modification or may be used to form palindromic probes described herein:

```
LANFV                    (SEQ ID NO: 22)

VFNALPPPPLAKFV           (SEQ ID NO: 23)
(palindromic probe)

FLVHSS                   (SEQ ID NO: 24)

SSHVLFPPPPFLVHSS         (SEQ ID NO: 25)
(palindromic probe).
```

A probe comprising amino acid sequences that include at least 5 contiguous amino acid resides of amino acid residues 11-19 (emphasized below by double underlining) of the peptide fragment of transthyretin (AAH20791 [gi: 18089145]; MacPhee and Dobson, *J. Mol. Biol.*, 279(5):1203-1215, 2000)

(SEQ ID NO: 26)
MASHRLLLLCLAGLVFVSEAGPTGTGESKCPLMVKVLDAVRGSPAINVAV

HVFRKAADDTWEPFASGKTSESGELHGLTTEEEGVEGIYKVEIDTKSYWK

ALGISPFHEHAEVVFTANDSGPRRYTIAALLSPYSYSTTAVVTNPKE

A palindromic probe based on the above-referenced emphasized sequence of SEQ ID NO:26 (amino acid residues 11-19); such as ESVFVLGALPPPPLAGLVFVSE. (SEQ ID NO:27).

Probes having at least 15%, at least 20%, at least 30%, at least 40%, at least 50%, at least 60%, at least 70%, at least 80%, at least 90%, at least 99% to those exemplified above, and probes have equivalent sequences, also are included in the invention. Also included are probes that include the amino acid sequence of the above-referenced probes and have an additional N-terminal amino acid residue, C-terminal amino acid residue, or both, which is suitable for use in linking a label to the probe (e.g., Lys, which provides a free amino group for linking a label to the probe).

Numerous other probes may be readily produced without undue experimentation using standard laboratory techniques and peptide a related chemical syntheses. Other probes and methods of designing probes which may be used in the presently disclosed methods or modified for use in the presently disclosed methods may be readily obtained and are described in U.S. 2006-0057671; Wurth et al., J. Mol. Biol. 319:1279-1290 (2002); and Kim et al., J. Biol. Chem. 280:35059-35076 (2005), which are incorporated by reference herein in their entireties.

5. Labels

The probes disclosed herein may comprise a label. For example, the probe may comprise a peptide probe that is coupled or fused, either covalently or non-covalently, to a label. In one embodiment, the peptide probe is endcapped (at one or both ends of the peptide) with a moiety or chemical entity that may facilitate analysis of the peptide probe, including detection of the probe per se and detection of the structural state of the probe.

The specific label chosen may vary widely, depending upon the analytical technique to be used for analysis. The label may be complexed or covalently bonded at or near the amino or carboxy end of the peptide, which may be endcapped with a short, hydrophobic peptide sequence. In some aspects of the invention, both the amino and carboxy ends of the probe peptides are endcapped with small hydrophobic peptides ranging in size from about 1 to about 5 amino acids. These peptides may be natural or synthetic, but are preferably natural (i.e., derived from the target protein). A label may be attached at or near the amino and/or carboxy end of the probe.

As used herein, a "label" is a chemical or biochemical moiety useful for labeling the probe, and which, optionally, may be utilized to assess the specific structural state of the probe. For example, a label may emit a first signal based on a first structural state and a second signal based on a second structural state. The first signal and second signal may differ in intensity. In some embodiments where the signal includes emission of light, the first signal and second signal may differ in excitation wavelength and/or emission wavelength.

"Labels" may include fluorescent agents (e.g., fluorophores, fluorescent proteins, fluorescent semiconductor nanocrystals), phosphorescent agents, chemiluminescent agents, chromogenic agents, quenching agents, dyes, radionuclides, metal ions, metal sols, ligands (e.g., biotin, streptavidin haptens, and the like), enzymes (e.g., beta-galactosidase, horseradish peroxidase, glucose oxidase, alkaline phosphatase, and the like), enzyme substrates, enzyme cofactors (e.g., NADPH), enzyme inhibitors, scintillation agents, inhibitors, magnetic particles, oligonucleotides, and other moieties known in the art. Where the label is a fluorophore, one or more characteristics of the fluorophore may be used to assess the structural state of the labeled probe. For example, the excitation wavelength of the fluorophore may differ based on the structural state of the labeled probe. In some embodiments, the emission wavelength, intensity, or polarization of fluorescence may vary based on the structural state of the labeled probe.

As used herein, a "fluorophore" is a chemical group that may be excited by light to emit fluorescence or phosphorescence. A "quencher" is an agent that is capable of quenching a fluorescent signal from a fluorescent donor. A first fluorophore may emit a fluorescent signal that excites a second fluorophore. A first fluorophore may emit a signal that is quenched by a second fluorophore. The probes disclosed herein may undergo fluorescence resonance energy transfer (FRET).

Fluorophores and quenchers may include the following agent (or fluorophores and quenchers sold under the following tradenames): 1,5 IAEDANS; 1,8-ANS; umbelliferone (e.g., 4-Methylumbelliferone); acradimum esters, 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350%; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP(Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f, Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiC 18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow IOGF; Genacryl Pink 3G; Genacryl Yellow 5GF; GeneBlazer (CCF2); a fluorescent protein (e.g., GFP (S65T); GFP red shifted (rsGFP); GFP wild type, non-UV excitation (wtGFP); GFP wild type, UV excitation (wtGFP); and GFPuv); Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; luminol, Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-Xm conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl-RodaminelsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof. Fluorophores may include fluorescent proteins.

Labels may include derivatives of fluorophores that have been modified to facilitate conjugation to another reactive molecule. As such, labels may include amine-reactive derivatives such as isothiocyanate derivatives and/or succinimidyl ester derivatives of the label.

Labels may include a fluorescent protein which is incorporated into a probe as part of a fusion protein. Fluorescent proteins may include green fluorescent proteins (e.g., GFP, eGFP, AcGFP, TurboGFP, Emerald, Azami Green, and ZsGreen), blue fluorescent proteins (e.g., EBFP, Sapphire, and T-Sapphire), cyan fluorescent proteins (e.g., ECFP, mCFP, Cerulean, CyPet, AmCyan1, and Midoriishi Cyan), yellow fluorescent proteins (e.g., EYFP, Topaz, Venus, mCitrine, YPet, PhiYFP, ZsYellow1, and mBanana), and orange and red fluorescent proteins (e.g., Kusabira Orange, mOrange, dTomato, dTomato-Tandem, DsRed, DsRed2, DsRed-Express (T1), DsREd-Monomer, mTangerine, mStrawberry, AsRed2, mRFP1, JRed, mcherry, HcRed1, mRaspberry, HcRed-Tandem, mplum and AQ143). Other fluorescent proteins are described in the art (Tsien, R. Y., Annual. Rev. Biochem. 67:509-544 (1998); and Lippincott-Schwartz et al., Science 300:87-91 (2003)).

As noted above, the probes may be comprised in fusion proteins that also include a fluorescent protein coupled at the N-terminus or C-terminus of the probe. The fluorescent protein may be coupled via a peptide linker as described in the art (U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

In embodiments comprising in vivo imaging, labels useful for in vivo imaging can be used. For example, labels useful for magnetic resonance imaging, such as fluorine-18 can be used, as can chemiluminescent labels. In another embodiment, the probe is labeled with a radioactive label. For example, the label may provide positron emission of a sufficient energy to be detected by machines currently employed for this purpose. One example of such an entity comprises oxygen-15 (an isotope of oxygen that decays by positron emission) or other radionuclide. Another example is carbon-11. Probes labeled with such labels can be administered to a patient, permitted to localize at target protein, and the patient can be imaged (scanned) to detect localized probe, and thus identify sites of localized target protein. Labeled probes can be administered by any suitable means that will permit localization at sites of target protein, such as by direct injection, intranasally or orally. In some embodiments, radiolabeled probes can be injected into a patient and the binding of the probe to the protein target monitored externally.

Labels may include oligonucleotides. For example, the peptide probes may be coupled to an oligonucleotide tag which may be detected by known methods in the art (e.g., amplification assays such as PCR, TMA, b-DNA, NASBA, and the like).

6. Immobilized Probes and Uses Thereof

In some embodiments the peptide probes are immobilized on a solid support. This can be achieved by methods known in the art, such as methods comprising exposing a probe to a solid support for a sufficient amount of time to permit immobilization of the probe to the solid support. The methods may further comprise removing unbound probe, cross-linking the probe to the solid support (e.g., chemically and/or by exposure to UV-irradiation), and drying the solid support and probe. Methods of immobilizing peptides on solid supports are known in the art. In one embodiment, the probes are immobilized in a specific structural state, such as a specific conformation (e.g., predominantly α-helix/radon coil or predominantly β-sheet), as described in U.S. 2006-0057671, which is incorporated herein by reference in its entirety.

Probes immobilized to a solid support may be used to rapidly and efficiently detect the presence of target protein in a sample. Immobilized probes also are useful for binding some, essentially all, or all of a target protein present in a sample, after which the target protein can be separated from the rest of the sample, for example, to provide a purified sample that has a reduced target protein content, that is essentially free of target protein, or that is completely free of target protein. Thus for example, biological, medical or consumable compositions can be prepared that have a reduced content of target protein.

The solid support can be any known solid substance that is suitable for binding peptides and suitable for use with biological materials. Many such solid supports are known to those of skill in the art. Examples of materials that are useful as solid supports, include, but are not limited to, plastics, including polystyrene, glass, polysaccharides, metal, and various polymers, including latex, acrylics, and nylons. Examples of forms of solid supports include, but are not limited to, plates, beads, and membranes.

In general, a method of detecting a target protein using an immobilized probe comprises providing an immobilized probe, providing a sample containing or suspected of containing a target protein, exposing the sample to the immobilized probe under conditions and for an amount of time sufficient for the immobilized probe to bind to a target protein in the sample (if present), and detecting the presence of target protein bound to the immobilized probe. Detection may be by way of any known technique, as discussed and detailed above. In some embodiments, detection comprises assaying emission of light from a label, such as by fluorescence or luminescence. In other embodiments, detection is by PAGE and staining of proteins present in the gel. In yet other embodiments, detection is by reaction with an antibody specific for a target protein of interest. Other non-limiting examples of detection techniques are given above with reference to labels.

Reaction conditions can be selected by those skilled in the art according to routine considerations. Suitable conditions include an aqueous environment, neutral pH (e.g., pH from about 6.0 to about 8.0), moderate salt (e.g., from about 100 mM to about 400 mM salt), and little or no detergents, emulsifiers, or other ancillary substances that might inhibit protein-protein interactions. The amounts of immobilized probe and sample to be used will vary depending on the amount of sample available, the amount of target protein suspected of being present in the sample, the amount of time the user wishes to expose the sample to the immobilized probe, and other considerations.

In general, a method of reducing the target protein content of a sample comprises providing an immobilized probe, providing a sample containing or suspected of containing a target protein, exposing the sample to the immobilized probe under conditions and for an amount of time sufficient for the immobilized probe to bind to at least some of the target proteins in the sample (if present), and separating the immobilized probe and immobilized probe-target protein complexes from the sample. In some embodiments, the method reduces the amount of target protein in the sample by an amount that is detectable. In other embodiments, the method reduces the amount of target protein in the sample to an amount below detection limits. In other embodiments, the method completely eliminates target proteins from a sample.

Methods of reducing target protein content of a sample can be effected under conditions similar to those described above for detecting target protein. Separating the immobilized probe and immobilized probe-target protein complexes from the sample may be by any suitable technique, such as by pouring off of the sample, by physical removal of the immobilized probe and complexes from the sample, etc. Those of skill in the art are aware of numerous ways of removing beads, membranes, and other solid supports from aqueous solutions, and any of those ways may be used to separate the immobilized probe and immobilized complexes from the sample. In some embodiments, the immobilized probe is a probe bound to a membrane that is permeable to the sample, such as blood or blood products, such as plasma. In these embodiments, the sample is filtered through the probe-bound membrane to remove some or all of the target proteins from the sample, e.g., from the blood or blood product. Passing of the last of the sample across the membrane causes separation of the probe-bound membrane and the sample. After the sample has been filtered, the probe-bound membrane may be assayed for the presence of target proteins.

As is evident from the above disclosure, the invention also includes detecting the presence of target protein bound to the immobilized probe. Detection may be by way of any known technique, as discussed and detailed above. Likewise, various additional steps may be included in the methods, as long as those steps do not render the methods incapable of removing some or all of the prion proteins present in a sample.

D. DETECTION OF PROTEINS AND PROTEIN STRUCTURES

As noted above, one aspect of the invention provides probes for detecting proteins in a sample or in vivo, and for detecting proteins in a specific structural state (e.g., a target structural state). For example, a peptide probe may be labeled such that it fluoresces when the peptide probe is an alpha-helix or random coil conformation (or soluble state), and does not fluoresce when the peptide probe is in a beta-sheet conformation (or insoluble aggregated state). Likewise, a peptide probe may be labeled such that it does not form excimers when the peptide probe is an alpha-helix or random coil conformation (or soluble state), but does form excimers when the peptide probe is in a beta-sheet conformation (or insoluble aggregated state). Exemplary labels include fluorophores or fluorescent proteins, such as pyrene, tryptophan, fluorescein, rhodamine, GFP, and numerous others as described herein.

Traditionally, protein structures have been determined by a variety of experimental or computational methods described in the art. See, e.g., U.S. 2006-0057671; U.S. Pat. No. 6,448,087; Waldo et al., Nat. Biotech. 17:691-695 (1999); Wurth et al., J. Mol. Biol. 319:1279-1290 (2002); Kim et al., J. Biol. Chem. 280:35069-35076 (2005), which are incorporated by reference herein in their entireties. For example, protein structure may be assessed experimentally by any method capable of producing at least low resolution structures. Such methods currently include X-ray crystallography and nuclear magnetic resonance (NMR) spectroscopy. X-ray crystallography is one method for protein structural evaluation, and is based on the diffraction of X-ray radiation of a characteristic wavelength by electron clouds surrounding the atomic nuclei in the crystal. X-ray crystallography uses crystals of purified biomolecules (but these frequently include solvent components, co-factors, substrates, or other ligands) to determine near atomic resolution of the atoms making up the particular biomolecule. Techniques for crystal growth are known in the art, and typically vary from biomolecule to biomolecule. Automated crystal growth techniques are also known.

Nuclear magnetic resonance (NMR) currently enables determination of the solution conformation (rather than crystal structure) of biomolecules. Typically, only small molecules, for example proteins of less than about 100-150 amino acids, are amenable to this technique. However, recent advances have lead to the experimental elucidation of the solution structures of large proteins, using such techniques as isotopic labeling. The advantage of NMR spectroscopy over X-ray crystallography is that the structure is determined in solution, rather than in a crystal lattice, where lattice neighbor interactions may alter the protein structure. The disadvantage of NMR spectroscopy is that the NMR structure is not as detailed or as accurate as a crystal structure. Generally, biomolecule structures determined by NMR spectroscopy are of moderate resolution compared to those determined by crystallography.

In the context of the present invention, the native or altered (e.g., after contact with a target protein) conformation of a peptide probe may be determined by one or more methods such as CD, Fourier transform infra-red, ultra-violet, NMR, or fluorescence, light scattering, hydrophobicity detection using extrinsic fluors, such as 1-anilino-8-naphthalene sulfonate (ANS) or Congo Red stain, fluorescence resonance energy transfer (FRET), quenching of intrinsic tryptophan fluorescence through either conformational change or monomer or binding at an interface in an α-β heterodimer, equilibrium ultracentrifugation, and size-exclusion chromatography. See, e.g., PHYSICAL BIOCHEMISTRY: APPLICATIONS TO BIOCHEMISTRY AND MOLECULAR BIOLOGY, $2^{nd}$ ed., W.H. Freeman & Co., New York, N.Y., 1982, for descriptions of these techniques.

As noted above, in some embodiments, the probe is modified to comprise labels that are detectable by optical means. Such labels may include tryptophan (an amino acid), pyrene or similar fluorophores, or a fluorescent protein, attached at or near the terminal positions of the peptide probe. Attachment of labels such as fluorophores is achieved according to conventional methods which are well known in the art.

1. Excimers

In one embodiment, the labels have the capability to interact in such a manner as to produce a species known as an excimer. An excimer is an adduct that is not necessarily covalent and that is formed between a molecular entity that has been excited by a photon and an identical unexcited molecular entity. The adduct is transient in nature and exists until it fluoresces by emission of a photon. An excimer represents the interaction of two fluorophores that, upon excitation with light of a specific wavelength, emits light at a different wavelength, which is also different in magnitude from that emitted by either fluorophor acting alone. It is possible to recognize an excimer (or the formation of an excimer) by the production of a new fluorescent band at a wavelength that is longer than that of the usual emission spectrum. An excimer may be distinguished from fluorescence resonance energy transfer since the excitation spectrum is identical to that of the monomer.

The formation of the excimer is dependent on the geometric alignment of the fluorophores and is heavily influenced by the distance between them. In one embodiment, fluorophores are present at each probe terminus and excimer formation between fluorophores is negligible as long as the overall probe conformation is α-helix or random coil. This is readily determined by measurement of the fluorescent behavior of the probe in the solvent to be used for analysis in the absence of the target protein. In some embodiments, interaction of the probe with the target protein causes a structural change (such as a conformational change) in the probe such that excimer formation occurs. This is readily measured by the procedures described herein. For example, conversion of the probe structure from that exhibited in the absence of analyte (α-helix or random coil) to a β-sheet structure may enable fluorophores attached to the probes to form excimers that may be readily identified. Further, the magnitude of excimer formation is directly related to the amount of protein analyte present.

Thus, in accordance with one aspect of the invention, labeled probes form excimers when they adopt a specific structural state, such as a target structural state, such as may occur when the probes interact with target protein in the target structural state. The formation of excimers may be detected by a change in optical properties. Such changes may be measured by known fluorimetric techniques, including UV, IR, CD, NMR, or fluorescence, among numerous others, depending upon the fluorophore attached to the probe. The magnitude of these changes in optical properties is directly related to the amount of probe that has adopted the structural state associated with the change, and this is directly related to the amount of target protein present.

2. Circular Dichroism

"Circular dichroism" ("CD") is observed when optically active matter absorbs L and R hand circular polarized light slightly differently, as measured by a CD spectropolarimeter. Differences are very small and represent fractions of degrees in ellipticity. CD spectra for distinct types of secondary structure present in peptides and proteins are distinct. Measuring and comparing CD curves of complexed vs. uncomplexed protein represents an accurate measuring means for the methods disclosed herein.

3. The GFP System

In one embodiment, a GFP fusion protein system is used to determine the specific structural state of probe or a test protein. Fusion proteins that include a test protein and green fluorescent protein (GFP) have been described to determine solubility of the test protein. See, e.g., Waldo et al., Nat. Biotech. 17:691-695 (1999); U.S. Pat. No. 6,448,087, Wurth et al., J. Mol. Biol. 319:1279-1290 (2002); Kim et al., J. Biol. Chem. 280:35059-35076 (2005), each of which are incorporated herein by reference in their entireties. Because folding of GFP into its native fluorescent structure is thought to occur slowly (Cubitt et al., Trends Biochem. Sci. 20:448-455 (1995), the fluorescence of a GFP fusion protein may depend on the solubility of the test protein. If the test protein is insoluble, the GFP portion of the fusion protein may be pulled out of solution with the test protein, and thereby prevented from folding into its fluorescent structure.

In the context of the present invention, GFP fusion proteins are useful for identifying a probe or test protein in a specific structural state, for identifying a probe specific for a test protein in a specific structural state, and for identifying agents that affect the structural state of the target protein. For example, the fluorescence of a GFP-probe fusion or GFP-test protein fusion is indicative of a soluble probe or test protein with a low tendency to form self-aggregates. In contrast, a lack of fluorescence is indicative of the presence of an insoluble or self-aggregating probe or test protein.

Thus, one aspect of the invention provides a fusion protein comprising (a) a peptide probe for a target protein, such as a peptide probe comprising an amino acid sequence corresponding to a region of the target protein that undergoes a conformational shift from an alpha-helical conformation to a beta-sheet conformation, where the peptide probe undergoes a conformational shift from an alpha-helical conformation to a beta-sheet conformation and the peptide probe does not comprise the full-length sequence of the target protein; and (b) a fluorescent protein (e.g., green fluorescent protein (GFP)). Optionally, the fusion protein further includes a polypeptide linker that links the peptide probe and the fluorescent polypeptide. In the context of this aspect of the invention, "GFP" includes proteins exhibiting equivalent folding and fluorescent properties of the full-length GFP protein, such as derivatives or fragments of the full-length GFP protein having at least about 60% sequence identity to the full-length GFP protein.

Suitable target proteins include amyloid islet polypeptide precursor protein, amyloid beta protein or Aβ peptide, serum amyloid A, insulin, amylin, non-amyloid beta component, prions, hemoglobin, immunoglobulins or fragments thereof β$_2$-microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.

In some embodiments, the target protein is the prion protein (e.g., PrP$^C$, PrP$^{Sc}$, or a mixture thereof), and the peptide probe may include SEQ ID NO:13 or a related sequence. In another embodiment, the target protein is amyloid beta protein (e.g., Aβ42, Aβ 40, or a mixture thereof), and the peptide probe may include SEQ ID NO:32, SEQ ID NO:4, or a related sequence. In further embodiments, the target protein is amyloid islet polypeptide precursor protein, and the peptide probe may include SEQ ID NO:11 or a related sequence. In still further embodiments, the target protein is transthyretin protein, and the peptide probe may include SEQ ID NO:26, or a related sequence. In even further embodiments, the target protein is cystatin C protein, and the peptide probe may include SEQ ID NO:17 or a related sequence. In even further embodiments, the target protein is Huntington's disease protein (i.e., Huntingin), and the peptide probe includes SEQ ID NO:19, or a related sequence.

As noted above, the fusion protein may emit a fluorescent signal correlated with its solubility. Thus, for example, a soluble fusion protein may exhibit a strong fluorescent signal while an insoluble protein will not fluoresce. While not wanting to be bound by any theory, it is believed that, at least in the context of amyloid proteins, the fluorescence of a fusion protein also is correlated with the conformational state of the peptide probe. Thus, for example, the fusion protein may emit a fluorescent signal when the peptide probe is in an alpha-helical conformation, while the fusion protein may not emit a fluorescent signal when the peptide probe is in a beta-sheet conformation.

In some embodiments, the peptide probe is in an alpha-helical conformation when present in a solution of 1.0% SDS having a pH of about 7. In further embodiments, the peptide probe is in a beta-sheet conformation when present in a solution having a pH of about 4.5. Optionally, the fusion protein is immobilized on a solid support (e.g., where the fusion protein further comprises an avidin moiety, and is coupled to the solid support via a biotin moiety).

The fusion proteins may be prepared by cloning a DNA sequence that encodes the peptide probe into a GFP expression vector (see, e.g., Waldo et al., Nature Biotechnol. 17, 691-695 (1999)). For example, the DNA sequence that encodes the peptide probe may be obtained by PCR amplification of a target sequence that encodes the peptide probe, or alternatively, by preparing overlapping oligonucleotides that encode the peptide probe when annealed (see, e.g., Kim et al., J. Mol. Biol. 319:1279-1290 (2002)). Subsequently, the DNA sequence that encodes the peptide probe may be treated with restriction enzymes and cloned into the GFP expression vector.

4. Surface Plasmon Resonance

Biomolecular structures may also be studied by assessing "surface plasmon resonance" or "SPR." The phenomenon of SPR is observed as a dip in intensity of light reflected at a specific angle from the interface between an optically transparent material (e.g., glass), and an opaque material, and depends on among other factors the refractive index of the medium (e.g., a sample solution) close to the surface of the opaque material (see WO 90/05295). A change of refractive index at the surface of the opaque material, such as by the adsorption or binding of material thereto, will cause a corresponding shift in the angle at which SPR occurs. In an SPR-based protein binding assay, a peptide probe may be contacted with a target protein that is immobilized on a surface of an opaque support. The interaction of the peptide probe with the target protein thereafter may be assessed by monitoring SPR between the interface of the surface of the opaque support and a transparent material.

E. DETECTION METHODS FOR TARGET PROTEINS

In some embodiments of the disclosed methods, peptide probes are selected for addition to an unknown or test sample or for use in vivo, to detect target protein present in the sample or in vivo, including target protein present in a specific structural state. Detection methods can be carried out along the general lines set forth in U.S. Pat. No. 7,166,471; U.S. patent application Ser. No. 10/728,246; PCT application PCT/US2006/005095, and/or U.S. application Ser. No. 11/030,300, the entire contents of which are incorporated herein by reference in their entireties.

For in vitro embodiments, once a peptide probe is selected, it is added to a test sample. In some embodiments, such as with the detection of prion protein, it may be advantageous to subject the sample to disaggregation techniques commonly known in the art, such as sonication, prior to addition of the probe. The disaggregation step allows any potentially aggregated sample material to break apart so that these disaggregated sample materials are free to combine with the newly introduced peptide probe, thereby facilitating interaction between the probe and the target protein, and detection of the target protein.

After the test sample or disaggregated test sample is allowed to interact with the peptide probes, the resulting mixture is then subjected to analytical methods commonly known in the art for the detection of interaction between the probe and the target protein. In some embodiments, the target protein is immobilized on a solid support. The peptide probe is contacted with the target protein and allowed to interact. Subsequently, non-bound peptide probe is removed and bound peptide probe is observed by detecting a signal from a detectable label on the probe. For example, where the detectable label is a fluorophore, the bound peptide probe may be illuminated to stimulate emission from the fluorophore. Where the detectable label is a radioisotope, the bound peptide may be contacted with a scintillant to stimulate emission from the scintillant. Alternatively, detection may be effected using antibodies, such as antibodies for the target protein which will bind to any target protein bound by the probe.

In some embodiments, the peptide probe and target protein may be contacted in the presence of a test agent to assess the ability of the test agent to inhibit an interaction between the peptide probe and target protein.

In one embodiment, the probe has a predominately α-helix or random coil conformation prior to being contacted with the target protein, and undergoes a shift to a β-sheet conformation when contacted with target protein in a β-sheet conformation. In accordance with specific aspects of this embodiment, the conformational change of the probe propagates further conformational changes in other probes that come into contact with the probe that has undergone the conformational change, thereby amplifying the detection reaction signal. Thus, unknown or test samples containing β-sheet conformation characteristic of abnormally folded or disease-causing proteins result in an increase in β-sheet formation and, often, the formation of insoluble aggregates in the text mixture containing both the test sample and the peptide probes. Conversely, unknown or test samples that lack any predominantly β-sheet secondary structures will neither catalyze a transition to β-sheet structure nor induce the formation of aggregates. This aspect of the invention may be particularly advantageous when the target protein is a prion protein.

For example, a sample comprising TSE may be analyzed as follows. Referring to FIG. 2, the top row of the schematic illustrates an unknown sample of TSE protein represented as containing β-sheets. The β-sheets are disaggregated by sonication. Labeled peptide probes are added and are allowed to bind to the sample. The i-sheet conformation in the sample induces the peptide probes to conform to a β-sheet conformation. Beta-sheet propagation among the peptide probes forms aggregates. The resulting transition to a predominantly β-sheet form and amplified aggregate formation is detected by techniques such as light scattering and CD. In some embodiments, the peptide probe is fluorescently labeled and fluorescence detection is used.

In one further embodiment, any propagated conformational change is directly correlated with levels of disease-associated proteins (such as prions) with the progressive state (or infectivity) of the disease.

In some embodiments, such as those relating to prion proteins, it may be preferable to utilize the presently disclosed methods manner in which there is no increase in infectious products as a result of the propagation. This may be achieved by placing a "break" in the links between the chain of infection, transmission, and propagation of the abnormal form. Such a break may occur at the transitional stage between the dimer and multimer forms of the aggregate. The physical formation of the multimer form may be blocked by simply impeding the step that leads to its formation. This may be achieved by using a probe in which the sequence of interest is attached to a non-relevant peptide, or by a neutral "blocker" segment, with the understanding that probes on linkers or "tethers" are more likely to encounter each other and result in amplifying the signal.

In some embodiments, the test sample is subject to conditions that promote the structural shift, for example, a conformational shift from an alpha-helical conformation to a beta-sheet conformation which may result in aggregation. Such conditions are known in the art. For example, the binding of a metal ligand could direct a change in the protein conformation and favor aggregation; the expression or cleavage of different peptide sequences may promote advanced aggregation leading to fibril and plaque formation; genetic point mutations also may alter the relative energy levels required of the two distinct conformations, resulting in midpoint shifts in structural transitions; an increase in concentration levels could be sufficient to favor a conformational transition. In other embodiments, the test sample is "seeded" with aggregates of short peptide sequences. For example, synthetic and/or recombinant prion proteins and fibrils may be less reactive with peptide probes than biologically derived prion protein. This reduced reactivity can be overcome, however, by seeding the reaction mixture with aggregates of small prion-derived sequences, such as, for example a prion peptide comprising residues 106-126 ($PrP_{106-126}$). Regardless of the initial trigger mechanism, the end result may be the catalytic propagation of the abnormal conformation, resulting in structural transformation of previously normal protein.

In in vivo embodiments, a labeled peptide probe is administered to a patient, such as by local injection, allowed to localize at any sites of target protein or higher order target protein structures present within the patient, and then the patient can be scanned to detect the sites of labeled probe localized at sites of target protein or higher order target protein structures. Other routes of administration also are contemplated, including intranasal and oral. As discussed above, the probe can be labeled with any label suitable for in vivo imaging. The patient can be subject to a full body scan to identify any site of target protein. Alternatively, specific areas of the patient can be scanned to determine whether target protein is localized in the specific areas. Specific areas of interest may include vascular tissue, lymph tissue or brain (including the hippocampus or frontal lobes), or other organs such as the heart, kidney, liver or lungs.

As noted above, in some embodiments, a peptide probe is specific for a target protein in a specific structural state. For example, a peptide probe may preferentially bind to target protein in an alpha-helix or random coil conformation, and have a lower (or no) affinity for target protein in a beta-sheet conformation. Conversely, a peptide probe may preferentially bind to target protein in a beta-sheet conformation and have a lower (or no) affinity for target protein in an alpha-helix or random coil conformation. Likewise, a peptide probe may preferentially bind to a target protein in a specific state of self-aggregation. For example, a peptide probe may preferentially bind to soluble monomers of the target protein, to soluble oligomers of the target protein, to insoluble self-aggregates (including amorphones self-aggregates), to protobrils or to fibrils, and have a lower (or no) affinity for target protein in a different state. Such probes are useful for identifying target protein in the specific structural state preferentially recognized by the peptide probe.

As used herein, a peptide probe that "preferentially binds to the target protein in a specific state of self-aggregation" means that the peptide probe binds in a dose-dependent manner to target protein in a specific state of self-aggregation, and does not bind in a dose-dependent manner to target protein in a different state of self-aggregation. For example, a peptide probe may preferentially bind to target protein in higher-order states of self-aggregation, such that the peptide probe binds in a dose-dependent manner to oligomers and fibers and does not bind in a dose-dependent manner to monomers.

For example, peptide probes consisting of or comprising the amino acid sequence of SEQ ID NO:36 or SEQ ID NO:45 specifically react with Aβ40 and Aβ42 oligomers, and do not specifically react with Aβ40 and Aβ42 monomers. Thus, these peptide probes are useful for identifying higher order structures of Aβ40 and Aβ42.

Thus, one aspect of the invention provides methods for identifying a target protein present in a specific structural form in a sample, comprising (a) contacting the sample with a peptide probe for the target protein, where the peptide probe preferentially binds to the specific structural form of the target protein, and (b) detecting any binding between the peptide probe and any target protein present in the specific structural form.

As discussed above, the peptide probe may further include a label (e.g., pyrene, tryptophan, a fluorescent polypeptide label such as green fluorescent protein (GFP), and a radionuclide label), and may optionally be immobilized on a solid support.

Alternatively, in vivo methods for identifying a target protein present in a specific structural form in a patient may comprise (a) administering to the patient a peptide probe for the target protein, where the peptide probe preferentially binds to the specific structural form of the target protein, and (b) scanning the patient to detect any localized peptide probe, thereby detecting and any target protein in the specific structural form that may be present in the patient. As discussed above, the peptide probe may be labeled with any label suitable for detection by in vivo imaging, and the probe can be administered by any suitable route of administration. As noted above, the patient can be subject to a full body scan, or specific areas can be scanned or imaged, such as vascular tissue, lymph tissue or brain (including the hippocampus or frontal lobes), or other organs such as the heart, kidney, liver or lungs.

The structural form of the target protein may include a beta-sheet conformation or an alpha-helical conformation. In some embodiments, the structural form of the target protein is a monomer of the protein. In other embodiments, the structural form of the target protein is a soluble oligomer of the protein. Structural forms also may include insoluble self-aggregates of the protein (e.g., insoluble amorphous self-aggregates, protofibrils, and fibrils).

For example, in the context of AD, peptide probes can be used to identify soluble Aβ protein, ADDLs, insoluble aggregates of Aβ protein, protofibrils and fibrils present in a sample. The ability to identify specific structural forms of Aβ protein offers significant clinical advantages. For example, the presence and load of Aβ42 protein and higher order Aβ structures (e.g., ADDLs, protofibrils, and fibrils) can be used to identify a patient at risk for AD or a patient suffering from AD, and/or the extent to which the disease has progressed. The same information also could be used to determine the need for a therapeutic regimen or for a more or less aggressive regimen than currently being used, and to monitor the efficacy of a given therapeutic regimen.

In one embodiment, peptide probes are used to determine the location of Aβ42 protein or higher order Aβ structures within the patient. For example, biological samples from specific segments of the brain can be obtained and analyzed for the presence of Aβ42 protein or higher order Aβ structures. Alternatively, labeled probes can be administered to the patient, such as by local injection, allowed to localize at any sites of Aβ42 protein or higher order Aβ structures present within the patient, and then the patient can be scanned to detect the sites of labeled probe localized at sites of Aβ42 protein or higher order Aβ structures. Specific sites of interest might include the hypocampus or frontal lobes of the brain. Other sites of interest might include vascular tissue, lymph tissue, and other organs such as the heart, kidney, liver or lungs.

Another aspect of the invention provides a method for determining the amounts of Aβ42 and/or Aβ40 in a sample, and the ratio of Aβ42 to Aβ40 in a sample. As noted above, the amount of Aβ42 (or "load") circulating in patient plasma or CSF is correlated with diseases such as AD and LLMD. Similarly, a high ratio of Aβ42 to Aβ40 is indicative of a disease state. The present invention provides methods of determining these values using peptide probes that preferentially bind to either Aβ42 or Aβ40, and thus can be used to quantify the amount of Aβ42 or Aβ40 present in a sample. By testing a sample with each type of probe (simultaneously or sequentially), the absolute and relative loads can be determined. That information can be used, for example, to identify a patient at risk for AD or a patient suffering from AD, and/or the extent to which the disease has progressed. The same information also could be used to determine the need for a therapeutic regimen or for a more or less aggressive regimen than currently being used, and to monitor the efficacy of a given therapeutic regimen. Similar information could be obtained by in vivo methods, along the lines discussed above.

Likewise, in the context of prion proteins, peptide probes can be used to identify soluble monomers of $PrP^{Sc}$, soluble aggregates of $PrP^{Sc}$, insoluble aggregates of $PrP^{Sc}$, protofibrils and/or fibrils present in a sample or in vivo. The ability to identify specific structural forms of $PrP^{Sc}$ offers significant clinical advantages. For example, the soluble aggregate form of $PrP^{Sc}$ is believed to be the most infective form; thus, the identification of that form of $PrP^{Sc}$ can be used to identify an infected subject. The same information also could be used to determine the need for a therapeutic regimen or for a more or less aggressive regimen than currently being used, and to monitor the efficacy of a given therapeutic regimen.

In one embodiment, peptide probes are used to determine the location of $PrP^{Sc}$ protein or higher order $PrP^{Sc}$ structures (such as soluble aggregates) within a patient. For example, biological samples from specific segments of the brain can be obtained and analyzed for the presence of $PrP^{Sc}$ protein or higher order $PrP^{Sc}$ structures. Alternatively, labeled probes can be administered to the patient, such as by local injection, allowed to localize at any sites of $PrP^{Sc}$ protein or higher order $PrP^{Sc}$ structures present within the patient, and then the patient can be scanned to detect the sites of labeled probe localized at sites of $PrP^{Sc}$ protein or higher order $PrP^{Sc}$ structures.

Another aspect of the invention provides a method for determining the amounts of $PrP^{Sc}$ in a sample, or the amount of a specific form of $PrP^{Sc}$ in a sample. As noted above, the soluble aggregate form of $PrP^{Sc}$ is highly infective. The present invention provides methods of determining the amount of that form of $PrP^{Sc}$ present in a sample, using peptide probes that preferentially bind to the soluble aggregate form of $PrP^{Sc}$. That information can be used, for example, to evaluate the infective burden of a patient and/or the extent to which the disease has progressed. The same information also could be used to determine the need for a therapeutic regimen or for a more or less aggressive regimen than currently being used, and to monitor the efficacy of a given therapeutic regimen. Similar information could be obtained by in vivo methods, along the lines discussed above.

The invention also provides methods of identifying probes that are specific for a target protein in a specific structural state. In some embodiments, the tendency of a probe to adopt a specific structural state corresponds with the probe's specificity for a target protein in that specific structural state. Thus, a probe with a high tendency to form insoluble self-aggregates is specific for target protein in an insoluble self-aggregated state; a probe with a tendency to form soluble self-aggregates is specific for target protein in a soluble self-aggregated state, and a probe with no tendency to form aggregates is specific for target protein in a non-aggregated state (such as a monomeric state). In some embodiments, the probe may exhibit a low tendency to form self-aggregates. For example, the probe may include the amino acid sequence of a variant of Aβ42 having amino acid substitutions 141D and A42Q (i.e., "the DQ mutant").

Probes specific for a target protein in a specific structural state that falls on a spectrum of structural states ranging from a low end of soluble monomers to a high end of insoluble self-aggregates can be identified in accordance with the present invention, such as by using the GFP system. For example, a fusion protein comprising (i) a peptide probe for the target protein and (ii) GFP can be subjected to conditions that promote self-aggregation, and any fluorescent signal can be detected. The intensity of the signal can be correlated with the specificity of the probe for a target protein in a specific structural state. For example, in some embodiments, a higher intensity signal indicates that the probe has a low tendency to form aggregates, and thus is specific for a target protein at a lower end of the spectrum of structural states, such as a soluble monomer. Conversely, in some embodiments, a lower intensity signal indicates that the probe has a higher tendency to form aggregates and is specific for a target protein at a higher end of the spectrum of structural states, such as an insoluble aggregate. An intermediate signal may indicate that the probe has an intermediate tendency to form aggregates and is specific for a target protein at an intermediate end of the spectrum of structural states, such as a soluble oligomer.

Probes specific for a target protein in a specific structural state also can be identified by preparing samples of protein in different specific structural states, and then assessing the ability of a peptide probe to preferentially bind to protein in one or more of the different specific structural states. For example, a peptide probe can be contacted with a sample of a protein in a specific structural state, and its interaction with the protein assessed using, for example, any of the methodologies described above. This process can be repeated using samples of protein in different specific structural states, and the results can be compared to determine whether the peptide probe preferentially binds to protein in one or more of the different specific structural states.

F. SCREENING METHODS FOR IDENTIFYING AGENTS THAT MODULATE AGGREGATION

The probes disclosed herein may be used in screening methods for identifying agents that modulate self-aggregation of a target protein.

For example, to screen for agents that modulate self-aggregation of a target protein, a fusion protein is prepared which comprises a peptide probe for the target protein and a label which generates a signal dependant on the aggregative state of the protein, such as GFP. (In some embodiments, the label is linked to the C-terminus of the peptide probe, directly or through a linker). As discussed above, in the GFP system, the fluorescence of the fusion protein is inversely correlated with the peptide probe's tendency to form insoluble self-aggregates. Thus, for example, if the fusion protein is observed to emit a fluorescent signal, the peptide probe has a low tendency to form insoluble self-aggregates. Conversely, if the fusion protein is observed to not emit a fluorescent signal, the peptide probe has a higher tendency to form insoluble self-aggregates. Other labels described above can be used in place of GFP. Those skilled in the art recognize that some labels will emit a signal that is inversely correlated with aggregation, while others will emit a signal that is directly correlated with aggregation. For convenience, the invention is described with reference to the GFP system.

In some circumstances, it may be desirable to determine the relative tendency of a peptide probe to form aggregates. To that end, a signal generated by a reference fusion protein (e.g., comprising GFP and a reference peptide probe) is compared to a signal generated by a test fusion protein (e.g., comprising GFP and a test peptide probe). In the GFP system, an increasing fluorescence signal correlates with a lower tendency to form aggregates.

In some embodiments, peptide probes with a high tendency to form insoluble self-aggregates are used in screening methods for identifying agents that modulate self-aggregation of a target protein. In one aspect of this embodiment, the GFP fusion protein (e.g., peptide probe-GFP) is cloned into a vector for inducible expression in a host cell (e.g., E. coli). Expression is induced in E. coli in the presence of a test agent for inhibiting self-aggregation of target protein. Fluorescence of the fusion protein (due to the GFP moiety) is measured, and fluorescence in the presence of a test agent identifies the test agent as a potential inhibitor of target protein self-aggregation.

In another aspect, the screening method comprises an in vitro assay. For example, a GFP fusion protein is cloned into a vector for "cell-free" expression as known in the art. The fusion protein then is expressed in the presence of a test agent and fluorescence is measured. Again, fluorescence in the presence of a test agent identifies the test agent as a potential inhibitor of target protein self-aggregation.

In variations of these embodiments, a GFP fusion protein is expressed in the absence of the test agent and in the presence of the test agent, and an increase in fluorescence identifies a test agent that inhibits aggregation.

In other variations of these embodiments the fusion protein is expressed in the presence of the test protein (and test agent).

Suitable test agents for the screening methods may include antibodies, chelating agents, tridentate iron chelators, diketones, 2-pyridoxal isonicontinyl hydrazone analogues, tachypyridine, clioquinol, ribonucleotide reductase inhibitor chelators, 2,3-dihydroxybenzoic acid, Picolinaldehyde, Nicotinaldehyde, 2-Aminopyridine, 3-Aminopyridine, topical 2-furildioxime, n-Butyric acid, Phenylbutyrate, Tributyrin, suberoylanilide hydroxamic acid, 6-cyclohexyl-1-hydroxy-4-methyl-2(1H)-pyridinone, rilopirox, piroctone, benzoic acid-related chelators, salicylic acid, nicotinamide, Clioquniol, heparin sulfate, trimethylamine N-oxide, polyethylene glycol (PEG), copper cations, dimethylsulfoxide, Dexrazoxane, dopamine, tannic acid, triazine, levodopa, pergolide, bromocriptine, selegiline, glucosamine or analogs thereof, tetrapyrroles, nordihydroguaiaretic acid, polyphenols, tetracycline, polyvinylsulfonic acid, 1,3-propanedisulfonic acid, β-sheet breaker peptide (iAβ5), nicotine, or salts or derivatives thereof.

Suitable target proteins for the screening methods may be any of those discussed above. The screening methods can be used to identify agents that modulate aggregation of any target protein that is susceptible to self-aggregation, including prion proteins and Aβ42. These methods also can identify agents that bind to target protein. Binding of an agent to a monomer of the target protein will prevent self-aggregation of the target protein. Similarly, binding of an agent to a soluble oligomer or an insoluble aggregate will prevent further aggregation and protofibril and fibril formation, while binding of an agent to a protofibril or fibril will prevent further extension of that structure. In addition to blocking further aggregation, this binding also may shift the equilibrium back to a state more favorable to soluble monomers, further halting the progression of the disease and alleviating disease symptoms.

Binding of target protein by an agent also may directly interfere with any detrimental activity exhibited by the target protein.

In one specific embodiment, the activity of a test agent identified as described above is confirmed in a further assay. For example, a soluble form of the target protein or a peptide probe for the target protein is prepared using organic solvents, sonication, and filtration (Bitan et al., Methods in Molec. Biol., pp. 3-9 (2005, Humana Press). After preparation, the soluble form of the target protein or probe is diluted in aqueous buffer that includes a test agent identified as described above, and the target protein or probe is allowed to aggregate under agitation or under quiescence. Aggregation then is measured by any of the methods described above, such as by using a labeled probe and detecting excimer formation or CD, or by other methods known in the art such as measuring fluorescence of Thioflavin T (Levine-III, H., Protein Sci. 2:404-410 (1993) or Congo-red binding, to confirm that a test agent inhibits aggregation.

In one embodiment, the activity of a test agent identified as described above using a GFP-peptide probe fusion protein is confirmed by assessing the fluorescence of a GFP-target protein fusion protein in the presence of the test agent.

The ability of a test agent to inhibit aggregation also may be assessed by observing aggregation of a target protein (or a probe) in the presence of the test agent under electron microscopy. A dose dependent decrease in aggregation confirms that the test agent inhibits aggregation.

The invention also provides for more tailored drug screening, i.e., by identifying active agents that interact with specific structural states of the target protein. In this embodiment, the ability of a test agent to interact with a probe with a tendency to form a specific structural state is used to identify agents that interact with target protein in that specific structural state. For example, probes with a low tendency to self-aggregate can be used to identify active agents that bind to monomers of the target protein; probes with a tendency to form soluble oligomers (such as those that mimic the structure of Aβ ADDLs) can be used to identify active agents that bind to soluble oligomers; probes with a tendency to form insoluble aggregates can be used to identify active agents that bind to insoluble monomers of the target protein. In some embodiments, probes with a low tendency to self-aggregate may be used to identify active agents that bind to the target protein in competition assays. For example, where the probe and active agent form a complex, additional probe, which optionally may be derivatized, can be used to compete off the probe from the complex.

In another variation, active agents that interact with a specific structural state of the target protein are identified by contacting the active agent with a sample of target protein, separating complexed active agent-target protein moieties from non complexed target protein, and determining the specific structural state of the complexed target protein using probes for specific structural states, as described herein.

G. THERAPEUTIC TEST AGENTS

Any agent known or suspected of inhibiting the specific structural state associated with a disease state may be used in screening methods to assess its ability to modulate aggregation, and thus its candidacy as a therapeutic agent. For example, agents known or suspected of inhibiting formation of the β-sheet conformation of a target protein, of inhibiting the formation of oligomers or insoluble amorphous self-aggregates of the target protein, or of inhibiting formation of fibrils, can be screened by the present methods to identify therapeutic agents. Peptide probes designed as described above (with or without a label) also are suitable as test agents to assess their likely usefulness as therapeutic agents.

Examples of therapeutic test agents include agents known or suspected to have anti-amyloid activity or anti-amyloidogenic activity. An "anti-amyloid agent" or "anti-amyloidogenic agent" is an agent which, directly or indirectly, inhibits proteins from aggregating and/or forming amyloid plaques or deposits and/or promotes disaggregation or reduction of amyloid plaques or deposits. For example, an anti-amyloid agent may inhibit a protein from assuming a conformation that is involved in aggregation and/or formation of oligomers, fibrils, amyloid plaques, etc. Thus, for example, an anti-amyloid agent may inhibit a protein from assuming a beta-sheet conformation. Anti-amyloid agents include proteins, such as anti-amyloid antibodies and peptide probes, and also include small chemical molecules, such as small molecule drugs.

1. Traditional Anti-Amyloid Agents

Anti-amyloid agents include chelating agents (e.g., chelating agents for transition metals such as copper and iron such as tridentate iron chelators), diketones (e.g., beta-diketones), 2-pyridoxal isonicontinyl hydrazone analogues, tachypyridine, clioquinol, ribonucleotide reductase inhibitor chelators, 2,3-dihydroxybenzoic acid, Picolinaldehyde, Nicotinaldehyde, 2-Aminopyridine, 3-Aminopyridine, topical 2-furildioxime, n-Butyric acid, Phenylbutyrate, Tributyrin, suberoylanilide hydroxamic acid, 6-cyclohexyl-1-hydroxy-4-methyl-2(1H)-pyridinone, rilopirox, piroctone, benzoic acid-related chelators, salicylic acid, nicotinamide, Clioquniol, heparin sulfate, trimethylamine N-oxide (TMNO), polyethylene glycol (PEG), copper cations (e.g., $Cu^{++}$), dimethylsulfoxide (DMSO), and Dexrazoxane.

Anti-amyloid agents also include agents generally referred to in the art as "amyloid busters" or "plaque busters." These include drugs which are peptidomimetic and interact with amyloid fibrils to slowly dissolve them. "Peptidomimetic" means that a biomolecule mimics the activity of another biologically active peptide molecule. "Amyloid busters" or "plaque busters" also include agents which absorb co-factors necessary for the amyloid fibrils to remain stable.

Anti-amyloid agents also include dopamine, tannic acid, triazine, levodopa, pergolide, bromocriptine, selegiline, glucosamine or analogs thereof (e.g., 4-deoxy-D-glucosamine or 4-deoxy-acetylglucosamine), tetrapyrroles, nordihydroguaiaretic acid (NDGA), polyphenols (e.g., myricetin (Myr), morin (Mor), quercetin (Qur), kaempferol (Kmp), (+)-catechin (Cat), (−)-epicatechin (epi-Cat)), rifampicin (RIF), tetracycline (TC), small molecule sulfonic acids (e.g., polyvinylsulfonic acid and 1,3-propanedisulfonic acid), small molecule sulphonates and sulfates (e.g., ethanesulfphonate, 1-propanesulphonate, 1,2-ethanedisulphonate, 1,3-propaenedisulphonate, 1,4-butanedisulphonate, 1,5-propanedisulphonate, 1,6-hexanedisulphonate, poly(vinylsulphonate), 1,2-ethanediol disulphate, 1,3-propanediol disulphate, and 1,4-butanediol disulphate), cyclohexanehexyl (e.g., epi-cyclohexanehexyl, scyllo-cyclohexanehexyl, and myo-cyclohexanehexyl), β-sheet breaker peptide (iAβ35), nicotine, or salts, acids, or derivatives thereof.

Anti-amyloid agents also may include antibodies, such as antibodies specific to the target protein, or antibodies specific to a specific structural state of the target protein.

2. Peptide Probes as Anti-Amyloid Agents

As noted above, peptide probes of the present invention are useful as anti-amyloid agents in the prevention and treatment of amyloidogenic diseases such as AD, and in the prevention of advanced stages of amyloidogenic diseases. As described above, a peptide probe for a given target protein specifically binds to that protein, and may preferentially bind to a specific structural form of the target protein.

While not wanting to be bound by any theory, it is believed that binding of target protein by a peptide probe will prevent the formation of higher order assemblies of the target protein, thereby preventing or treating the disease associated with the target protein, and/or preventing further progression of the disease. For example, binding of a peptide probe to a monomer of the target protein will prevent self-aggregation of the target protein. Similarly, binding of a peptide probe to a soluble oligomer or an insoluble aggregate will prevent further aggregation and protofibril and fibril formation, while binding of a peptide probe to a protofibril or fibril will prevent further extension of that structure. In addition to blocking further aggregation, this binding also may shift the equilibrium back to a state more favorable to soluble monomers, further halting the progression of the disease and alleviating disease symptoms.

Binding of target protein by a peptide probe also may directly interfere with any detrimental activity exhibited by the target protein. Thus, for example, the neurotoxic effects of ADDLs could be inhibiting by the binding action of a peptide probe specific for the ADDLs. Thus, in one embodiment, binding by peptide probes blocks the interaction of ADDLs and protofibrils with synapses and neuronal membranes. In some embodiments, where the target protein binds to another protein (e.g., a receptor), the peptide probes may be designed to compete with the target protein for binding to the other protein. For example, a peptide probe may be designed to compete for binding to a receptor for the target protein, where the receptor is present in neuronal membranes or basement cell membranes.

In some embodiments, peptide probes may be designed to bind to proteins such as laminin, effector cell adhesion molecules (ECAMS) (e.g., selectin), and glycosaminoglycans (GAGS). (See U.S. 2006-0135529). For example, the peptide probes may be designed to bind to glycosaminoglycan (GAG) and inhibit GAG interactions with effector cell adhesion molecules (ECAM) such as selectin.

Thus, in one embodiment, there is provided a method for preventing the formation of protein aggregates of a target protein, comprising contacting the target protein with a peptide probe for the target protein, wherein the peptide probe preferentially binds to the target protein, thereby preventing the formation of higher order protein aggregates of the target protein. In some embodiments, the peptide probe preferentially binds to a specific structural state of the target protein. In some embodiments, the peptide probe preferentially binds to monomers of the target protein, thereby preventing the formation of protein aggregates. In other embodiments, the peptide probe preferentially binds to soluble oligomers of the target protein, thereby preventing the formation of insoluble protein aggregates. In other embodiments, the peptide probe preferentially binds to insoluble aggregates of the target protein, thereby preventing the formation of fibrils of the target protein. In specific embodiments, the peptide probe preferentially binds to insoluble aggregates such as amorphous self-aggregates, protofibrils, and fibrils.

The contacting can be effected by any means that results in the peptide probe contacting the target protein. For in vivo methods, to prevent the formation of protein aggregates of a target protein in a patient, the peptide probe can be administered to the patient by any suitable means, such as by direct injection, for example, into a site of localized target protein or into a site of interest, such as those described above, or by intranasal or oral administration.

H. TARGETING AGENTS

Peptide probes of the invention also are useful as targeting agents to deliver other active agents (such as any of the agents listed above) to target proteins, such as to Aβ proteins, or to specific forms of Aβ, such as Aβ42, Aβ42 monomers, Aβ42 ADDLs, insoluble aggregates of Aβ42, fibrils, etc. In this embodiment of the invention, a peptide probe is combined with one or more active agents, such as by conjugation directly or through a linker, by methods known in the art. The active agent may be a therapeutic active agent, such as any of those known in the art and those mentioned above, or it may be a detection agent, such as any of those known in the art and those described above with regard to peptide probe labels. In some embodiments, the peptide probe localizes at target protein present at a specific site in the patient, such one or more of vascular tissue, lymph tissue, brain, or other organs, such as kidney, liver, heart or lungs, thereby delivering therapeutic agent to such specific sites.

Thus, in one embodiment, there is provided a method for treating a disease associated with a target protein, comprising contacting the target protein with a fusion protein comprising (i) a peptide probe for the target protein, wherein the peptide probe preferentially binds to the target protein, and (ii) a therapeutic agent. In some embodiments, the peptide probe preferentially binds to a specific structural state of the target protein. The contacting can be effected by any means that results in the peptide probe contacting the target protein, as discussed above, such as by injection, intranasally or orally.

In some embodiments, the disease is Alzheimer's disease, the target protein is Aβ42, Aβ40, or both, and the therapeutic agent is selected from the group consisting of antibodies, heavy metal chelators and charge moieties. In other embodiments, the disease is TSE, the target protein is prion protein, and the therapeutic agent is selected from the group consisting of antibodies, heavy metal chelators and charge moieties. In other embodiments, the disease is senile systemic amyloidiosis or familial amyloid polyneuropathy, the target protein is transthyretin, and the therapeutic agent is selected from the group consisting of antibodies, heavy metal chelators and charge moieties. In some embodiments, the disease is Huntington's disease, the target protein is Huntingtin, and the therapeutic agent is selected from the group consisting of heavy metal chelators and charge moieties. In other embodiments, the disease is Parkinson's disease, the target protein is alpha-synuclein, and the therapeutic agent is selected from the group consisting of heavy metal chelators and charge moieties.

Also provided is a method of delivering a therapeutic agent comprising combining the therapeutic agent with a peptide probe for the target protein and administering the peptide probe-therapeutic agent combination to a patient in need thereof. In some embodiments, the peptide probe comprises an amino acid sequence corresponding to a region of the target protein that undergoes a conformational shift from an alpha-helical conformation to a beta-sheet conformation, and the peptide probe undergoes a conformational shift from an alpha-helical conformation to a beta-sheet conformation, but does not comprise the full-length sequence of the target protein. In some embodiments, the peptide probe preferentially binds to the target protein in a specific state of self-aggregation. In some embodiments, the peptide probe preferentially binds to the target protein in a specific state of self-aggregation selected from the group consisting of monomers, soluble oligomers and insoluble aggregates. In some embodiments, the therapeutic agent has anti-amyloid activity. In some embodiments, the peptide probe is combined with the therapeutic agent via conjugation, directly or through a linker.

Suitable patients for prevention or treatment can be identified by those skilled in the art. For example, patients can be identified by detecting target protein in biological samples obtained from the patients or by in vivo methods described above, by identifying other risk factors (such as a genetic mutation, apoE, or PET scanning showing amyloid deposits or plaques), or by a family history of amyloidogenic disease (including AD and LLMD). In one embodiment of the invention, blood samples are screened for the presence of one or more amyloid proteins, such as Aβ42, and patients with high levels of that protein, or with high Aβ42/Aβ40 ratios, are selected for treatment.

I. CONTROLS

In any of the methods disclosed herein, controls (either positive, negative, or both) may be run to validate the assay. Positive controls generally comprise performing the methods with samples that are known to comprise at least one target protein (typically of a specific, known type), and may be used to confirm that the methods are capable of detecting that protein and/or are specific for that particular protein. Generally, a positive control comprises a sample (at any stage of the procedure) to which is intentionally added a known target protein, typically in a known amount. Negative controls generally comprise performing the methods with samples that are known not to contain any target proteins, and may be used to confirm that the methods are not providing systematic false positive results. Other controls may be run at one or more particular stages in the methods to verify that those stages are functioning as expected. One of skill in the art is well aware of suitable controls and may design and implement them without undue experimentation.

J. SAMPLES AND SPECIMENS

"Test specimen" is a sample of material to be tested and is equivalent in meaning to, and used interchangeably with "sample." The sample may be prepared from tissue (e.g. a portion of ground meat, an amount of tissue obtained by a biopsy procedure, blood or a fraction of blood, such as plasma) by homogenization in a glass homogenizer or may be used directly as obtained. The amount of sample may be any amount suitable for the application in which the sample is used. For example, if blood or a blood fraction is used, it may be about 1 µl, about 100 µl, about 1 ml, about 10 ml., about 100 ml., about one liter (or one pint), or more. In some applications, large volumes of blood or blood products may be used as a sample, including amounts greater than one liter (or one pint). When solid tissue is the source of the sample, the sample should be between about 1 mg and 1 gm, preferably between 10 mg and 250 mg, ideally between 20 and 100 mg.

Proteins in samples or specimens may be detected in aggregated form or in the presence of other cellular constituents, such as lipids, other proteins, or carbohydrates. A sample preparation for analysis may be homogenized or subjected to a similar disruption of tissue or aggregate structures, and cellular debris may be removed by centrifugation. This process may be performed in the presence of a buffered salt solution and may utilize one of several detergents such as SDS, Triton X-100, or sarkosyl. Further concentration of the sample may be achieved by treatment with any of several agents; (e.g., phosphotungstate), which is employed according to the method of Safar et al., *Nature Medicine* 4:1157-1165, 1998.

A sample may be obtained for testing and diagnosis as follows. A sample may be prepared from tissue (e.g., a portion of ground meat, or an amount of tissue obtained by a biopsy procedure) by homogenization in a glass homogenizer or by mortar and pestle in the presence of liquid nitrogen. The amount of material should be between about 1 mg and 1 gm, preferably between 10 mg and 250 mg, such as between 20 mg and 100 mg. The material to be sampled may be suspended in a suitable solvent, preferably phosphate-buffered saline at a pH between 7.0 and 7.8. The addition of RNase inhibitors is optional. The solvent may contain a detergent (e.g., Triton X-100, SDS, sarkosyl, dioxycholate, IgePal (NP40)). Homogenization is performed for a number of excursions of the homogenizer, preferably between 10 and 25 strokes; such as between 15 and 20 strokes. The suspended sample is preferably centrifuged at between 100 and 1,000×g for 5-10 minutes and the supernatant material sampled for analysis. In some samples, it may be preferable to treat the supernatant material with an additional reagent, such as phosphotungstic acid according to the procedure described by Safar et al., *Nature Medicine* 4:1157-1165, 1998, and as modified by Wadsworth, *The Lancet* 358:171-180, 2001.

The amount of sample to be tested is based on a determination of the protein content of the supernatant solution as measured by the procedure described by Bradford (*Anal. Biochem.* 72:248-254, 1976). A rapid and sensitive method for determining microgram quantities of protein utilizes the principle of protein-dye binding. Preferably, the amount of protein in the sample to be tested is between about 0.5 mg and 2 mg of protein.

In addition to the procedure described above for tissue material, test samples may be obtained from serum, pharmaceutical formulations that might contain products of animal origin, spinal fluid, saliva, urine, or other bodily fluids. Liquid samples may be tested directly or may be subjected to treatment with agents such as phosphotungstic acid, as described above.

K. KITS

Kits may be prepared for practicing the methods disclosed herein. Typically, the kits include at least one component or a packaged combination of components for practicing a disclosed method. By "packaged combination" it is meant that the kits provide a single package that contains a combination of one or more components, such as probes, buffers, instructions, and the like. A kit containing a single container is included within the definition of "packaged combination." In some embodiments, the kits include at least one probe. For example, the kits may include a probe that is labeled with a fluorophore or a probe that is a member of a fusion protein. In the kit, the probe may be immobilized, and may be immobilized in a specific conformation. For example, an immobilized probe may be provided in a kit to specifically bind target protein, to detect target protein in a sample and/or to remove target protein from a sample.

The kits may include some or all of the components necessary to practice a method disclosed herein. Typically, the kits include at least one probe, optionally immobilized, in at least one container. The kits may include multiple probes, optionally immobilized, in one or more containers. For example, the multiple probes may be present in a single container or in separate containers, each containing a single probe.

In certain embodiments, a single probe (including multiple copies of the same probe) is immobilized on a single solid support and provided in a single container. In other embodiments, two or more probes, each specific for a different target protein or a different form of a single target protein, are provided in a single container. In some embodiments, the same immobilized probe is provided in multiple different containers (e.g., in single-use form), or multiple immobilized probes are provided in multiple different containers. In further embodiments, the probes are immobilized on multiple different types of solid supports. Any combination of immobilized probe(s) and container(s) is contemplated for the kits disclosed herein, and the practitioner is free to select among the combinations to achieve a suitable kit for a desired use.

A container of the kits may be any container that is suitable for packaging and/or containing the probes disclosed herein. Suitable materials include, but are not limited to, glass, plastic, cardboard or other paper product, and metal. The container may completely encase the immobilized probes or may simple cover the probe to minimize contamination by dust, oils, etc. The kits may comprise a single container or multiple containers, and where multiple containers are present, each container may be the same as all other containers, different than others, or different than some, but not all other containers.

The kits themselves may be made of any suitable material. Non-limiting examples of kit materials are cardboard or other paper product, plastic, glass, and metal.

Kits may comprise some or all of the reagents and supplies needed for immobilizing one or more probes to the solid support, or some or all of the reagents and supplies needed for binding of immobilized probes to prion proteins in a sample.

The kits disclosed herein may include one or more non-immobilized probes and one or more solid supports that do or do not include an immobilized probe. Such kits may comprise some or all of the reagents and supplies needed for immobilizing one or more probes to the solid support, or some or all of the reagents and supplies needed for binding of immobilized probes to prion proteins in a sample.

EXEMPLARY EMBODIMENTS

The following is a list of exemplary embodiments:
1. A fusion protein comprising:
(a) a peptide probe for a target protein, wherein: (i) the peptide probe comprises an amino acid sequence corresponding to a region of the target protein that undergoes a conformational shift from an alpha-helical conformation to a beta-sheet conformation, (ii) the peptide probe undergoes a conformational shift from an alpha-helical conformation to a beta-sheet conformation, and (iii) the peptide probe does not comprise the full-length sequence of the target protein; and
(b) green fluorescent protein (GFP).
2. The fusion protein of embodiment 1, further comprising a polypeptide linker that links the peptide probe and the GFP polypeptide.
3. The fusion protein of embodiment 1, wherein the target protein is selected from the group consisting of amyloid islet polypeptide precursor protein, amyloid beta protein or Aβ peptide, serum amyloid A, insulin, amylin, non-amyloid beta component, prions, hemoglobin, immunoglobulins or fragments thereof P2-microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.
4. The fusion protein of embodiment 3, wherein the target protein is a prion protein.
5. The fusion protein of embodiment 4, wherein the prion protein is $PrP^C$, $PrP^{Sc}$, or a mixture thereof.
6. The fusion protein of embodiment 4, wherein the peptide probe comprises SEQ ID NO:13 or a sequence having at least about 90% sequence identity to SEQ ID NO:13.
7. The fusion protein of embodiment 3, wherein the target protein is amyloid beta protein.
8. The fusion protein of embodiment 7, wherein the amyloid beta protein is Aβ42, Aβ 40, or a mixture thereof.
9. The fusion protein of embodiment 7, wherein the peptide probe comprises the sequence of SEQ ID NO:32, the sequence of SEQ ID NO:4, or a sequence having at least about 90% sequence identity to SEQ ID NO:32 or SEQ ID NO:4.

10. The fusion protein of embodiment 3, wherein the target protein is islet polypeptide precursor protein.
11. The fusion protein of embodiment 10, wherein the peptide probe comprises the sequence of SEQ ID NO:11 or a sequence having at least about 90% sequence identity to SEQ ID NO:11.
12. The fusion protein of embodiment 3, wherein the target protein is transthyretin protein.
13. The fusion protein of embodiment 12, wherein the peptide probe comprises the sequence of SEQ ID NO:26 or a sequence having at least about 90% sequence identity to SEQ ID NO:26.
14. The fusion protein of embodiment 3, wherein the target protein is cystatin C protein.
15. The fusion protein of embodiment 14, wherein the peptide probe comprises the sequence of SEQ ID NO:17 or a sequence having at least about 90% sequence identity to SEQ ID NO:17.
16. The fusion protein of embodiment 3, wherein the target protein is Huntington's disease protein.
17. The fusion protein of embodiment 15, wherein the peptide probe comprises the sequence of SEQ ID NO:19 or a sequence having at least about 90% sequence identity to SEQ ID NO:19.
18. The fusion protein of embodiment 1, wherein said fusion protein emits a fluorescent signal when the peptide probe is in an alpha-helical conformation.
19. The fusion protein of embodiment 1, wherein said fusion protein does not emit a fluorescent signal when the peptide probe is in a beta-sheet conformation.
20. The fusion protein of embodiment 1, wherein the peptide probe is in an alpha-helical conformation when present in a solution of 1.0% SDS having a pH of about 7.
21. The fusion protein of embodiment 1, wherein the peptide probe is in a beta-sheet conformation when present in a solution having a pH of about 4.5.
22. The fusion protein of embodiment 1, wherein the fusion protein is immobilized on a solid support.
23. The fusion protein of embodiment 22, wherein the fusion protein further comprises an avidin moiety, and is coupled to the solid support via a biotin moiety.
24. A method of assessing an agent's ability to inhibit aggregation of a target protein, comprising:
(A) contacting a fusion protein and a test agent, the fusion protein comprising:
(i) a peptide probe for the target protein, wherein: (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and
(ii) a label which generates a signal dependent on the aggregative state of the fusion protein;
(B) detecting a signal generated by the label; and
(C) correlating the signal with the ability of the agent to inhibit aggregation of the target protein.
25. The method of embodiment 24, wherein a decrease in the signal correlates with the ability of the agent to inhibit aggregation of the target protein.
26. The method of embodiment 24, wherein an increase in the signal correlates with the ability of the agent to inhibit aggregation of the target protein.
27. The method of embodiment 24, wherein the target protein is selected from the group consisting of amyloid islet polypeptide precursor protein, amyloid beta protein or Aβ peptide, serum amyloid A, insulin, amylin, non-amyloid beta component, prions, hemoglobin, immunoglobulins or fragments thereof β$_2$-microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.

28. The method of embodiment 24, wherein the test agent is a chelating agent.

29. The method of embodiment 24, wherein the test agent is selected from the group tridentate iron chelators, diketones, 2-pyridoxal isonicontinyl hydrazone analogues, tachypyridine, clioquinol, ribonucleotide reductase inhibitor chelators, 2,3-dihydroxybenzoic acid, Picolinaldehyde, Nicotinaldehyde, 2-Aminopyridine, 3-Aminopyridine, topical 2-furildioxime, n-Butyric acid, Phenylbutyrate, Tributyrin, suberoylanilide hydroxamic acid, 6-cyclohexyl-1-hydroxy-4-methyl-2(1H)-pyridinone, rilopirox, piroctone, benzoic acid-related chelators, salicylic acid, nicotinamide, heparin sulfate, trimethylamine N-oxide, polyethylene glycol (PEG), copper cations, dimethylsulfoxide, Dexrazoxane, dopamine, tannic acid, triazine, levodopa, pergolide, bromocriptine, selegiline, glucosamine or analogs thereof, tetrapyrroles, nordihydroguaiaretic acid, polyphenols, tetracycline, polyvinylsulfonic acid, 1,3-propanedisulfonic acid, β-sheet breaker peptide (iAβ5), nicotine, or salts or derivatives thereof.

30. The method of embodiment 24, wherein the label comprises a fluorophore.

31. The method of embodiment 24, wherein the fluorophore comprises pyrene or tryptophan.

32. The method of embodiment 24, wherein the label comprises a fluorescent polypeptide.

33. The method of embodiment 32, wherein the fluorescent polypeptide comprises green fluorescent protein (GFP).

34. The method of embodiment 24, wherein the label comprises a radionuclide.

35. The method of embodiment 24, wherein the fusion protein is immobilized on a solid support.

36. The method of embodiment 24, where the fusion protein further comprises an avidin moiety, and is coupled to the solid support via a biotin moiety.

37. The method of embodiment 24, further comprising, prior to detecting step (b), subjecting the peptide probe to conditions that promote aggregation, wherein the intensity of the signal is directly correlated with the ability of the agent to inhibit aggregation.

38. A method of assessing an agent's ability to inhibit aggregation of a target protein, comprising:
(A) contacting the target protein, a fusion protein, and a test agent, the fusion protein comprising:
 (i) a peptide probe for the target protein, wherein: (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and
 (ii) a label which generates a signal dependent on the aggregative state of the fusion protein;
(B) detecting a signal generated by the label; and
(C) correlating the signal with the ability of the agent to inhibit aggregation of the target protein.

39. The method of embodiment 38, wherein the signal is directly correlated with the ability of the agent to inhibit aggregation.

40. The method of embodiment 38, wherein the signal is inversely correlated with the ability of the agent to inhibit aggregation.

41. A method of assessing an agent's ability to inhibit aggregation of a target protein, comprising:
(A) subjecting a fusion protein to conditions that promote aggregation, the fusion protein comprising:
 (i) a peptide probe for the target protein, wherein: (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and
 (ii) a label which generates a signal dependent on the aggregative state of the fusion protein;
(B) detecting a first signal generated by the label;
(C) subjecting the fusion protein to conditions that promote aggregation in the presence of a test agent, and detecting a second signal generated by the label; and
(D) assessing the relative intensities of the first and second signals, thereby identifying an agent that inhibits aggregation of the target protein.

42. The method of embodiment 41, wherein a greater intensity of the second signal, as compared to the first signal, identifies an agent that inhibits aggregation of the target protein.

43. The method of embodiment 41, wherein a greater intensity of the first signal, as compared to the second signal, identifies an agent that inhibits aggregation of the target protein.

44. A method of assessing an agent's ability to inhibit aggregation of a target protein, comprising:
(A) contacting a fusion protein and the target protein, wherein the fusion protein comprises:
 (i) a peptide probe for the target protein, wherein: (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and
 (ii) a label which generates a signal dependent on the aggregative state of the fusion protein;
(B) detecting a first signal generated by the label;
(C) contacting the fusion protein, the target protein, and a test agent, and detecting a second signal generated by the label; and
(D) assessing the relative intensities of the first and second signals, thereby identifying an agent that inhibits aggregation of the target protein.

45. The method of embodiment 44, wherein a greater intensity of the second signal, as compared to the first signal, identifies an agent that inhibits aggregation of the target protein.

46. The method of embodiment 44, wherein a greater intensity of the first signal, as compared to the second signal, identifies an agent that inhibits aggregation of the target protein.

47. A method for identifying a target protein present in a specific structural form in a sample, comprising:
(a) contacting the sample with a peptide probe for the target protein, wherein the peptide probe preferentially binds to a specific structural form of the target protein;
(b) detecting any binding between the peptide probe and any target protein present in the specific structural form.

48. The method of embodiment 47, wherein the structural form of the target protein is a beta-sheet conformation.

49. The method of embodiment 47, wherein the structural form of the target protein is an alpha-helical conformation.

50. The method of embodiment 47, wherein the structural form of the target protein is a monomer of the protein.

51. The method of embodiment 47, wherein the structural form of the target protein is a soluble oligomer of the protein.

52. The method of embodiment 47, wherein the structural form of the target protein is an insoluble self-aggregate of the protein.

53. The method of embodiment 52, wherein the structural form of the target protein is selected from insoluble amorphous self-aggregates, protofibrils, and fibrils.

54. The method of embodiment 47, wherein target protein is selected from the group consisting of amyloid islet polypeptide precursor protein, amyloid beta protein or Aβ peptide, serum amyloid A, insulin, amylin, non-amyloid beta component, prions, hemoglobin, immunoglobulins or fragments thereof $\beta_2$-microglobulin, α-synuclein, rhodopsin, α1-antichymotrypsin, cystallins, tau, p53, presenilins, low-density lipoprotein receptor, apolipoproteins, superoxide dismutase, neurofilament proteins, transthyretin, procalcitonin or calcitonin, atrial natriuretic factor, gelsolin, cystic fibrosis transmembrane regulator, Huntington's disease protein, fibrinogen alpha-chain, phenylalanine hydroxylase, collagen, beta-hexosaminidase, and cystatin C protein.

55. The method of embodiment 47, wherein the peptide probe further comprises a fluorophore label.

56. The method of embodiment 55, wherein the fluorophore comprises pyrene or tryptophan.

57. The method of embodiment 47, wherein the peptide probe further comprises a fluorescent polypeptide label.

58. The method of embodiment 57, wherein the fluorescent polypeptide label comprises green fluorescent protein (GFP).

59. The method of embodiment 47, wherein the peptide probe further comprises a radionuclide label.

60. The method of embodiment 47, wherein the peptide probe is immobilized on a solid support.

61. The method of embodiment 60, where the peptide probe further comprises an avidin moiety, and is coupled to the solid support via a biotin moiety.

62. A method of identifying a peptide probe for a target protein that exhibits an increased or decreased tendency to form aggregates relative to a reference peptide probe, comprising:
(A) detecting a first signal generated by a reference fusion protein that comprises:
  (i) a reference peptide probe comprising: (a) an amino acid sequence corresponding to a region of the target protein that undergoes a conformational shift from an alpha-helical conformation to a beta-sheet conformation, (b) wherein the peptide probe undergoes a conformational shift from an alpha-helical conformation to a beta-sheet conformation, and (c) the reference peptide probe does not comprise the full-length sequence of the target protein; and
  (ii) green fluorescent protein;
(B) detecting a second signal generated by a test fusion protein comprising a test peptide probe and green fluorescent protein, wherein the test peptide probe is a mutant of the reference peptide probe that comprises an amino acid insertion, deletion or substitution relative to the amino acid sequence of the reference peptide probe; and
(C) correlating the intensity of the second signal relative to the first signal, thereby identifying a peptide probe for a target protein that exhibits an increased or decreased tendency to form aggregates relative to the reference peptide probe.

63. The method of embodiment 62, wherein an increased intensity of the second signal relative to the intensity of the first signal indicates a decreased tendency of the test peptide probe to form aggregates, and a decreased intensity of the second signal relative to the intensity of the first signal probe indicates an increased tendency of the test peptide probe to form aggregates.

64. The method of embodiment 62, wherein an decreased intensity of the second signal relative to the intensity of the first signal indicates a decreased tendency of the test peptide probe to form aggregates, and an increased intensity of the second signal relative to the intensity of the first signal indicates an increased tendency of the test peptide probe to form aggregates.

65. The method of embodiment 62, wherein the test peptide probe has at least about 15% sequence identity to the reference peptide probe.

66. The method of embodiment 62, wherein the test peptide probe is designed by a process comprising introducing a random sequence mutation into the amino acid sequence of the reference peptide probe.

67. A method of identifying a peptide probe specific for a target protein in a specific structural state that falls on a spectrum of structural states ranging from a low end of soluble monomers to a high end of insoluble self-aggregates, comprising:
(A) subjecting a fusion protein to conditions that promote self-aggregation, the fusion protein comprising:
  (i) a peptide probe for the target protein, wherein: (a) the peptide probe comprises an amino acid sequence corresponding to a region of the target protein that undergoes a conformational shift from an alpha-helical conformation to a beta-sheet conformation, (b) the peptide probe undergoes a conformational shift from an alpha-helical conformation to a beta-sheet conformation, and (c) the peptide probe does not comprise the full-length sequence of the target protein; and
  (ii) green fluorescent protein;
(B) detecting a signal generated by the fusion protein; and
(C) correlating the intensity of the signal with the specificity of the peptide probe for a target protein in a specific structural state, thereby identifying a peptide probe specific for a target protein in a specific structural state.

68. The method of embodiment 67, wherein a higher intensity signal indicates that the peptide probe is specific for a target protein at a lower end of the spectrum of structural states and a lower intensity signal indicates that the peptide probe is specific for a target protein at a higher end of the spectrum of structural states.

69. The method of embodiment 67, wherein a lower intensity signal indicates that the peptide probe is specific for a target protein at a lower end of the spectrum of structural states and a higher intensity signal indicates that the peptide probe is specific for a target protein at a higher end of the spectrum of structural states.

70. A method for preventing the formation of protein aggregates of a target protein, comprising contacting the target protein with a peptide probe for the target protein, wherein the peptide probe preferentially binds to the target protein, thereby preventing the formation of higher order protein aggregates of the target protein.

71. The method of embodiment 70, wherein the peptide probe preferentially binds to monomers of the target protein, thereby preventing the formation of protein aggregates.

72. The method of embodiment 70, wherein the peptide probe preferentially binds to soluble oligomers of the target protein, thereby preventing the formation of insoluble protein aggregates.

73. The method of embodiment 70, wherein the peptide probe preferentially binds to insoluble aggregates of the target protein, thereby preventing the formation of fibrils of the target protein.

74. The method of embodiment 73, wherein the insoluble protein aggregates comprise one or more of amorphous self-aggregates, protofibrils, and fibrils.

75. A method for treating a disease associated with a target protein, comprising contacting the target protein with a fusion protein comprising (i) a peptide probe for the target protein, wherein the peptide probe preferentially binds to the target protein, and (ii) a therapeutic agent.

76. The method of embodiment 75, wherein the disease is Alzheimer's disease, the target protein is Aβ42, Aβ 40, or both, and the therapeutic agent is selected from the group consisting of heavy metal chelators and charge moieties.

77. The method of embodiment 75, wherein the disease is TSE, the target protein is prion protein, and the therapeutic agent is selected from the group consisting of heavy metal chelators and charge moieties.

78. The method of embodiment 75, wherein the disease is senile systemic amylodiosis or familial amyloid polyneuropathy, the target protein is transthyretin, and the therapeutic agent is selected from the group consisting of heavy metal chelators and charge moieties.

79. The method of embodiment 75, wherein the disease is Huntington's disease, the target protein is Huntingtin, and the therapeutic agent is selected from the group consisting of heavy metal chelators and charge moieties.

80. The method of embodiment 75, wherein the disease is Parkinson's disease, the target protein is alpha-synuclein, and the therapeutic agent is selected from the group consisting of heavy metal chelators and charge moieties.

81. A therapeutic composition comprising:
(a) a peptide probe for a target protein, wherein: (i) the peptide probe comprises an amino acid sequence corresponding to a region of the target protein that undergoes a conformational shift from an alpha-helical conformation to a beta-sheet conformation, (ii) the peptide probe undergoes a conformational shift from an alpha-helical conformation to a beta-sheet conformation, and (iii) the peptide probe does not comprise the full-length sequence of the target protein; and
(b) a pharmaceutical excipient.

82. The composition of embodiment 81, further comprising an additional therapeutic agent.

83. The composition of embodiment 82, wherein the additional therapeutic agent has anti-amyloid activity.

84. A method of delivering a therapeutic agent for preventing aggregation of a target protein comprising combining the therapeutic agent with a peptide probe for the target protein, wherein the peptide probe comprises an amino acid sequence corresponding to a region of the target protein that undergoes a conformational shift from an alpha-helical conformation to a beta-sheet conformation, and the peptide probe undergoes a conformational shift from an alpha-helical conformation to a beta-sheet conformation and wherein the peptide probe does not comprise the full-length sequence of the target protein.

85. The method of embodiment 84, wherein the therapeutic agent has anti-amyloid activity.

EXAMPLES

The following examples are illustrative and should not be interpreted as limiting the present disclosure.

Example 1

Construction of GFP-Peptide Probe Fusion Proteins

A dsDNA oligonucleotide encoding a peptide probe for human prion protein or Aβ42 is synthesized. The dsDNA oligonucleotide includes restriction sites at the 5' and 3' ends for cloning the dsDNA oligonucleotide into a GFP expression vector (see Waldo et al., Nature Biotechnol. 17:691-695 (1999)). A dsDNA oligonucleotide and GFP expression vector are digested with the corresponding restriction enzymes and the dsDNA oligonucleotide is ligated into the GFP expression vector to create a GFP-fusion protein expression vector. The expression vector is used to transform *E. coli* which is grown under kanamycin selection. For one particular variant GFP-Peptide Probe, a GFP-fusion protein expression vector is created which includes a mutant full-length Aβ42 having 141D and A42Q substitutions (i.e., "the DQ mutant"), which mutant is observed to undergo slow aggregation.

Example 2

Screening of GFP Fusion Protein Expression

DNA libraries are isolated from the transformed *E. coli* strain and transformed into another suitable strain for IPTG-inducible protein expression. The transformed bacteria are plated onto nitrocellulose paper. After overnight growth at 37° C., the nitrocellulose papers are transferred to LB plates which include kanamycin for selection and IPTG (1 mM) for inducing expression. Colonies are counted and the green versus white phenotype is noted, with green phenotype corresponding to soluble fusion protein (e.g., non-aggregated peptide probe) and white phenotype corresponding to insoluble fusion protein (e.g., aggregated peptide probe).

Example 3

Measurement of GFP Fluorescence

Figure 4:
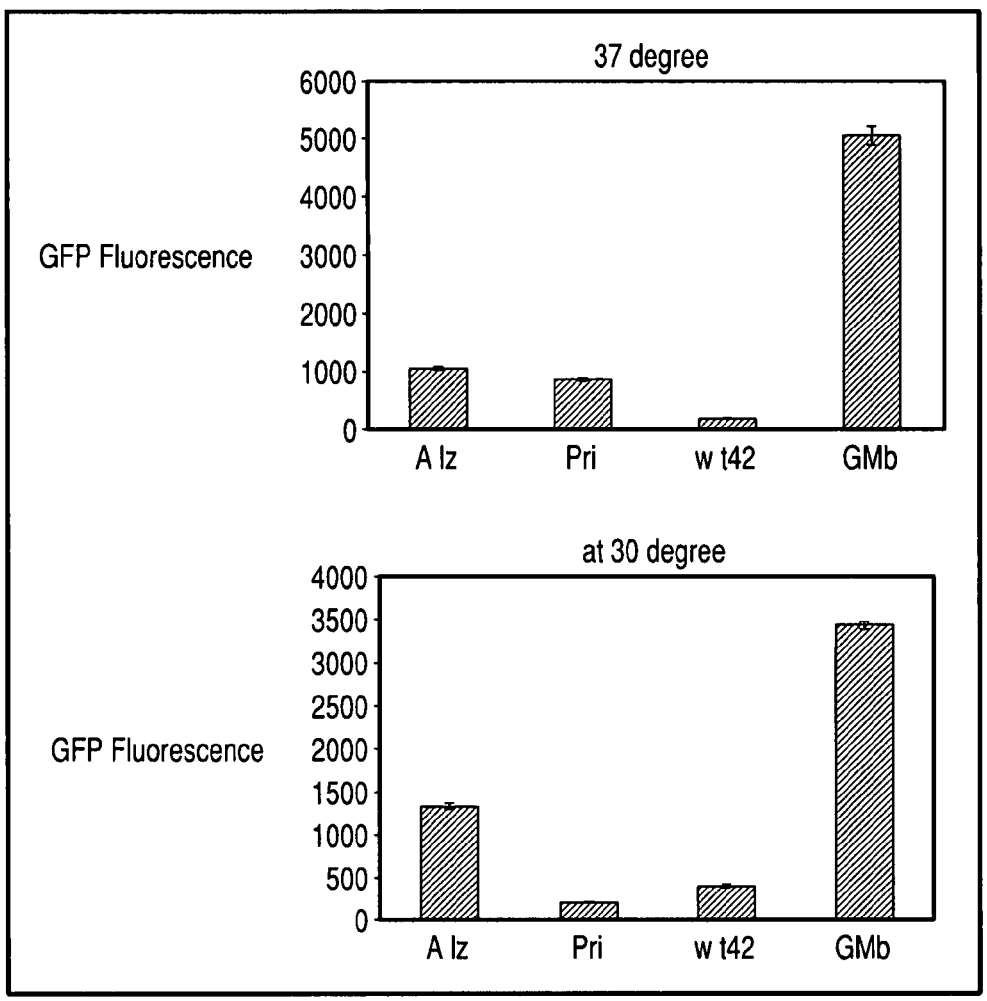
FIG. 4 illustrates the GFP fluorescence measurement of Alzheimer probe peptide-GFP fusion (Alz) and Prion probe peptide-GFP fusion (Pri). Measurements were taken after inducing expression and incubating the cells for 3 hours at 37° C. (left graph) or 5 hours at 30° C. (right graph).
Figure 5:
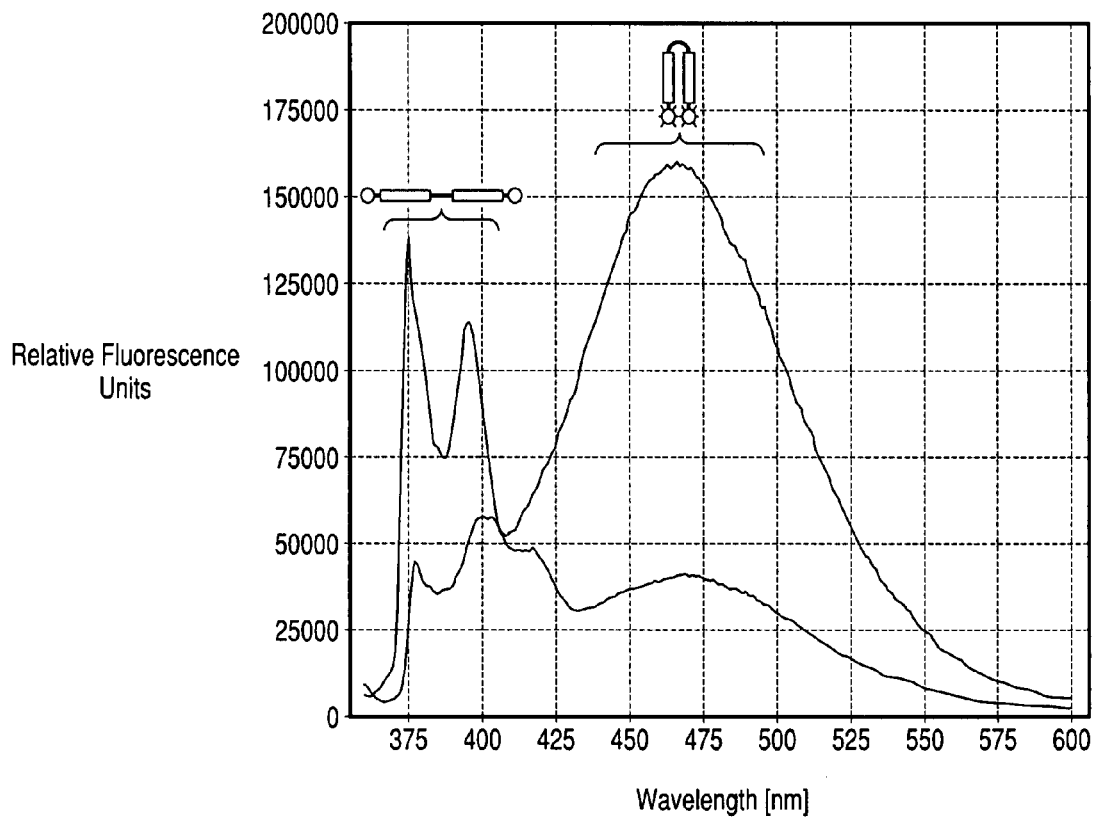
FIG. 5 illustrates the characteristic fluorescence of pyrene-labeled peptide probe monomers (measured at 378 nm) and dimers (measured at 495 nm).
Figure 6:
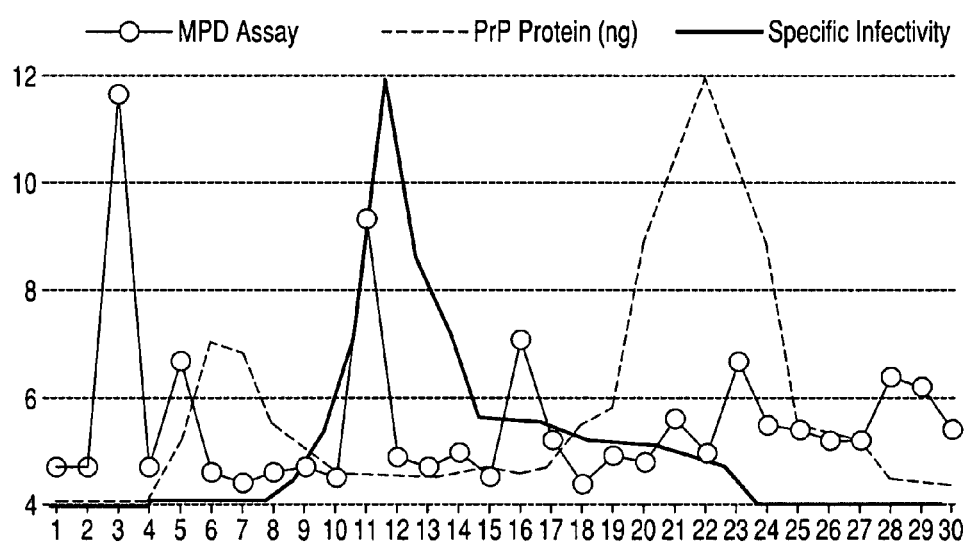
FIG. 6 illustrates the reactivity of a peptide probe specific for PrP$^{Sc}$ protein with PrP$^{Sc}$ present in thirty fractions obtained from samples from scrapie-infected hamster brain. The y-axis shows the relative $I_D/I_M$ ratios of each fraction. The size of the PrP$^{Sc}$ aggregates present in each fraction increases along the x-axis.
Figure 7:
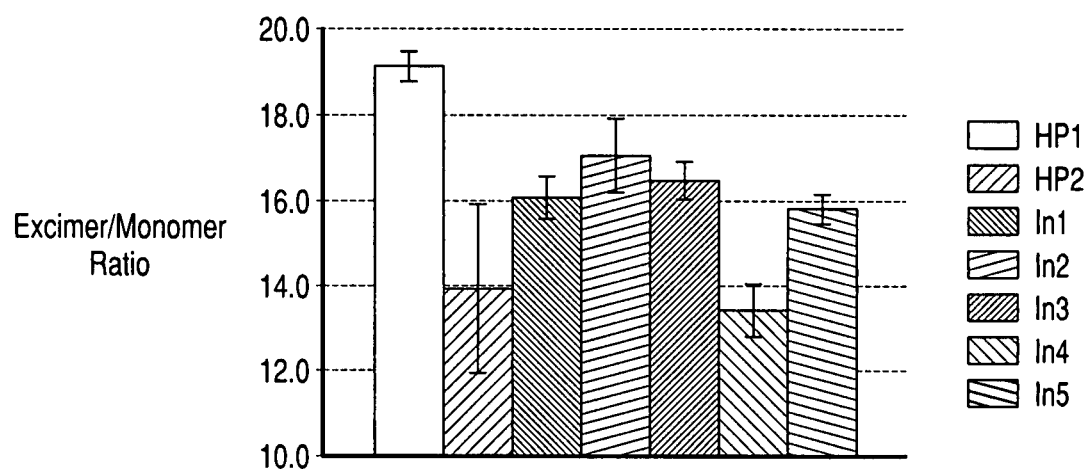
FIG. 7 illustrates the reactivity of a peptide probe specific for PrP$^{Sc}$ with PrP$^{Sc}$ in sera from infected sheep, and its lack of reactivity with sera from normal sheep. In the Figure, "HP 1" designates a sample from pooled serum of 3-month old healthy sheep; "HP 2" designates a sample from pooled serum of 2-year old healthy sheep; "ln1" to "ln4" designate serum from 18-24 month old scrapie sheep, and "ln5" designates serum from a terminal sheep.

Colonies are picked and grown in LB liquid media containing kanamycin. After the cultures reach an absorbance ($A_{600\,nm}$) of 0.8, expression is induced by addition of IPTG to a concentration of 1 mM and growth is continued at 37° C. or at 30° C. After induction, cultures are diluted in Tris-buffered saline to an $A_{600\,nm}$ of 0.15. Fluorescence is measured using a spectrofluorometer with excitation at 490 nm and emission at 510 nm. FIG. 4 provides exemplary results of the GFP fluorescence measurement of Alzheimer probe peptide-GFP fusion (Alz) and Prion probe peptide-GFP fusion (Pri). Measurements are taken after inducing expression and incubating the cells for 3 hours at 37° C. (left graph) or 5 hours at 30° C. (right graph). Expression of GFP-fusion proteins also are assessed by removing 200 μl of cell culture and analyzing the whole cell content by SDS-PAGE.

Example 4

GFP Fluorescent Screen for Inhibitors of Prion Aggregation

A GFP-peptide probe fusion protein known to yield a white phenotype in the assay described above (e.g., to form aggregates) is used to identify agents that inhibit aggregation. The vector for expressing a GFP-peptide probe (prion) fusion protein is transformed into bacterial cells for IPTG inducible expression. The transformed bacteria are grown in LB media supplemented with kanamycin for selection. When cultures reach an $OD_{600}=0.8$, an aliquot of culture (100 μl) is transferred to a well of a multi-well plate. Test agents are added to each well, and protein expression is induced by adding IPTG to a final concentration of 1 mM. Samples are incubated with gentle agitation at 37° C. Following 3 hours of incubation, the fluorescence of each well is measured at 512 nm (excitation 490 nm) using an automated plate reader. To confirm that cell densities are consistent across all samples, the $OD_{600}$ also is measured. Test agents are tested at multiple concentrations. Test agents that yield a green phenotype are identified as agents that inhibit aggregation.

Example 5

Identification of Peptide Probe Specific For Infective PrP$^{Sc}$

A peptide probe specific for a highly infective form of PrP$^{Sc}$ is identified as follows.

Figure 8:
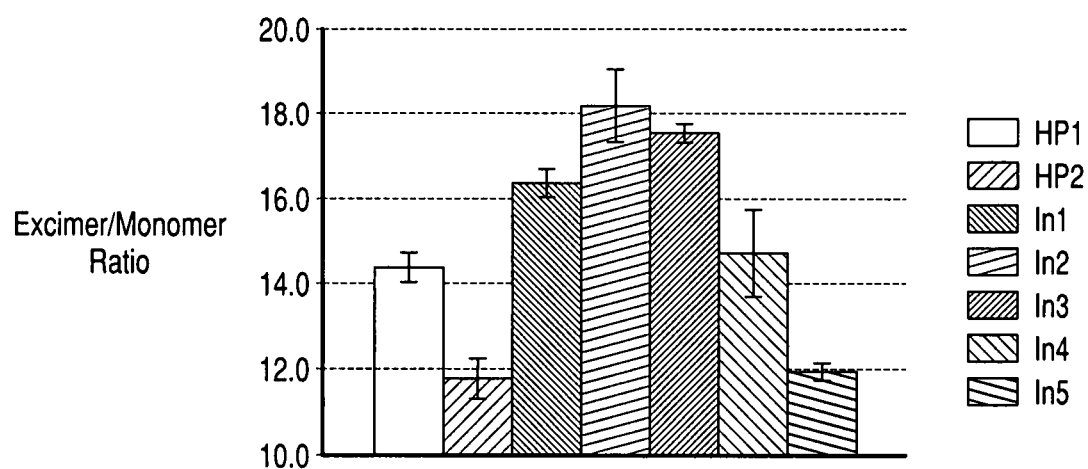
FIG. 8 illustrates the improvement in the signal-to-noise ratio achieved by sonicating samples prior to analysis of the reactivity of a peptide probe specific for PrP$^{Sc}$ with PrP$^{Sc}$ in sera from infected sheep and normal sheep. In the Figure, "HP 1" designates a sample from pooled serum of 3-month old healthy sheep; "HP 2" designates a sample from pooled serum of 2-year old healthy sheep; "ln1" to "ln4" designate serum from 18-24 month old scrapie sheep, and "ln5" designates serum from a terminal sheep.

Samples of PrP$^{Sc}$ protein ration by reducing the background in the "normal" samples. FIG. 8 also illustrates a better distinction of infected samples with the age matched normal pool (HP 2) from 2 year old animals versus the pool from 3 month old animals.

Example 7

Detection of PrP$^{Sc}$ in Sheep Buffy Coat, Serum and Plasma

Figure 9:
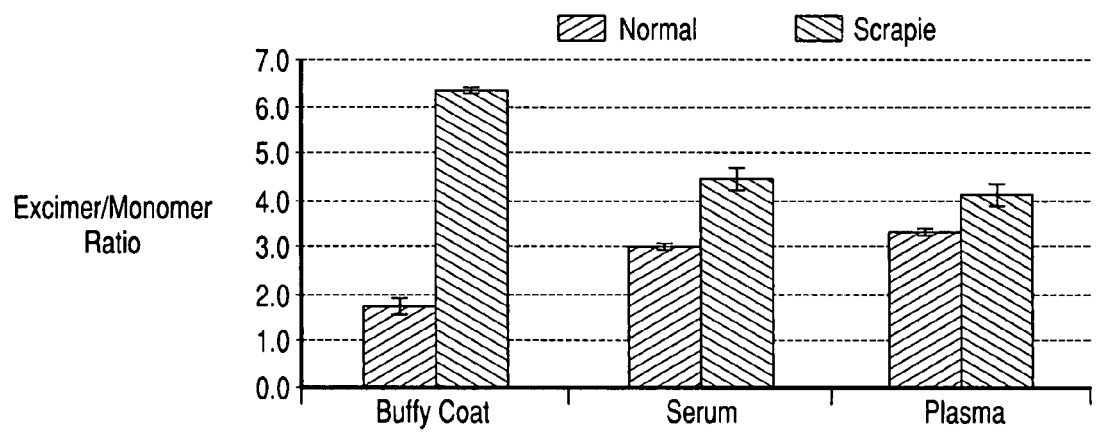
FIG. 9 illustrates the reactivity of a peptide probe specific for PrP$^{Sc}$ with PrP$^{Sc}$ present in sheep blood components (buffy coat, serum and plasma).

A peptide probe specific for PrP$^{Sc}$ (SEQ ID NO:43) is used to detect PrP$^{Sc}$ in sheep blood components as follows. Pyrene-labeled peptide probe is contacted with buffy coat, serum, and plasma samples from infected (scrapie) and normal (healthy) sheep, and the resulting fluorescence is measured as described above. FIG. 9 illustrates that the peptide probe exhibits a relative reactivity with sheep blood components in the order of buffy coat>serum>plasma.

Example 8

Identification of Aβ Peptide Probe

Figure 10:
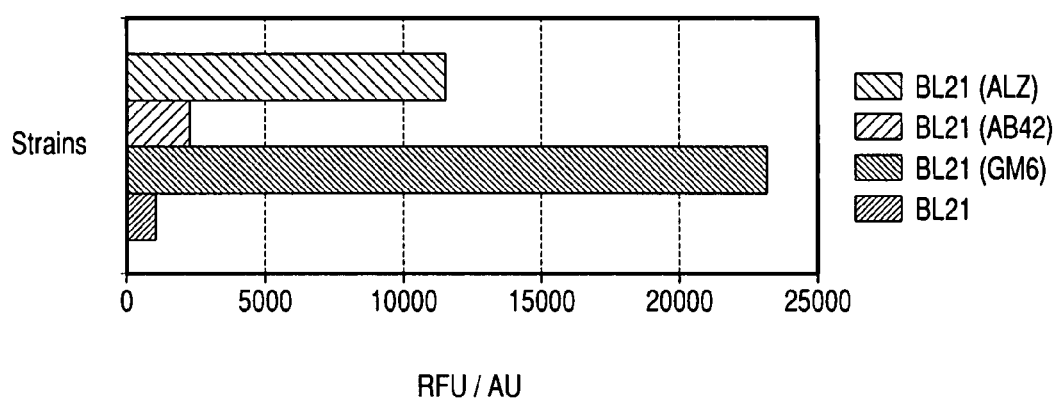
FIG. 10 illustrates the fluorescence, in a cell-based GFP assay of fusion proteins comprising GFP and a peptide probe specific for Aβ (SEQ ID NO:36); Aβ42 (SEQ ID NO:42), or the Aβ42 mutant clone GM6 (SEQ ID NO:44).

An Aβ peptide probe is identified as follows. A fusion protein is constructed that comprises a peptide probe specific for Aβ (SEQ ID NO:36) and GFP. Reference fusion proteins are constructed that comprise (i) Aβ42 (SEQ ID NO:42) and GFP or (ii) the Aβ42 mutant clone GM6 (SEQ ID NO:44) and GFP. The proteins are expressed and GFP fluorescence is detected as described above. As shown in FIG. 10, the Aβ42-GFP fusion protein exhibits little fluorescence because rapid aggregation of the Aβ42 moiety prevents proper folding of the GFP moiety required for fluorescence. In contrast, the mutant-GFP fusion protein exhibits a high level of fluorescence because GM6 is a slow folding mutant of Aβ42; thus the GM6 moiety does not interfere as much with the folding of the GFP moiety required for fluorescence. The peptide probe-GFP fusion protein exhibits an intermediate level of fluorescence, indicating that the peptide probe moiety interferes at a moderate level with GFP folding. These data indicate that the Aβ peptide probe (SEQ ID NO:36) will be useful in methods of identifying agents that affect Aβ peptide aggregation.

Example 9

Specificity of Aβ Peptide Probe For Aβ Oligomers

A peptide probe specific for Aβ (SEQ ID NO:36) is used to detect specific structural forms of Aβ40 and Aβ42. The peptide probe is labeled at each terminus with pyrene. The peptide probe is contacted with different samples comprising Aβ42 oligomers, Aβ40 oligomers, and Aβ40 monomers.

The morphological states of the Aβ protein is determined both by thioflavin T binding and by circular dichroism, using methodology described above. For example, peptides are brought up in 30% TFE/Tris for circular dichroism measurement and CDPRO deconvolution software is used for secondary structure calculation (Cellcon II (Freeware), Robert Woody, Colorado State University). The labeled peptide probe exhibits 18.3% α helix structure, 27.6% β strand (sheet) structure, and 54.1% turn/unordered structure. The peptide probe exhibits 19.4% α helix structure, 25.1% β strand (sheet) structure, and 55.5% turn/unordered structure. Aβ42 fibers exhibit 12.6% α helix structure, 60.2% β strand (sheet) structure, and 27.2% turn/unordered structure. Aβ40 fibers exhibit 5.6% α helix structure, 58.4% β strand (sheet) structure, and 35.9% turn/unordered structure. A sample of oligomers of Aβ42 (including dimers, trimers, tetramers, hexamers and 12-mers) exhibits 3.2% α helix structure, 52.7% β strand (sheet) structure, and 45.4% turn/unordered structure.

Figure 11A:
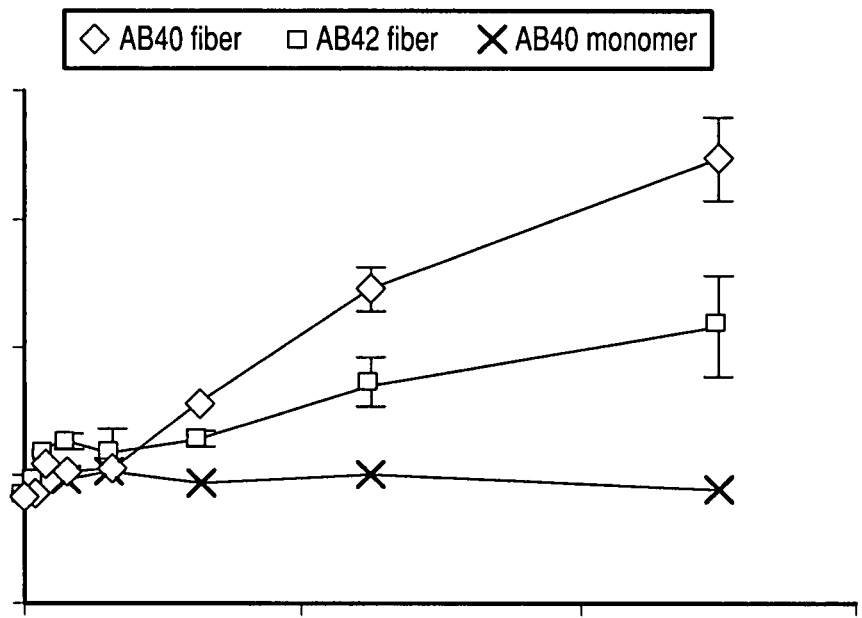
FIG. 11A shows reactivity with Aβ40 and Aβ42 fibers and non-reactivity with Aβ40 monomers.
Figure 11B:
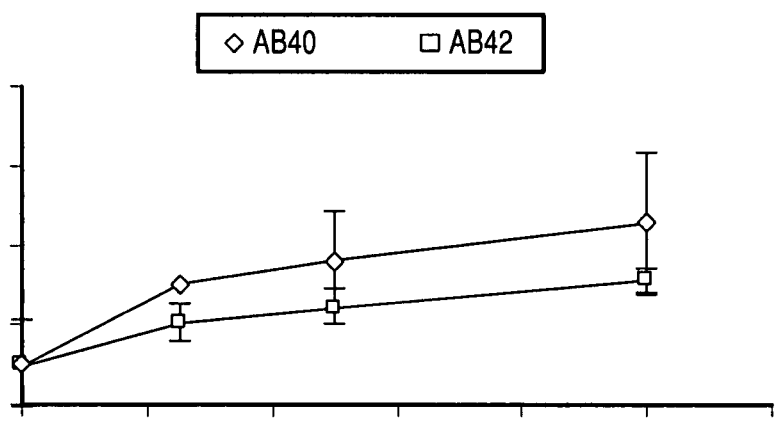
FIG. 11B shows reactivity with Aβ40 and Aβ42 oligomers.

Interaction between the peptide probe and sample is detected by excitation at 350 nm and scanning fluorescence from 360 to 600 nm. The peptide probe reacts with Aβ40 fibers and oligomers and Aβ42 fibers and oligomers in a dose-dependent manner, but dose not react with Aβ40 monomer in a dose dependent manner. FIG. 11A (fibers and monomer) & 11B (oligomers). These data show that the peptide probe preferentially binds to oligomeric forms of Aβ40 and Aβ42.

Example 10

Detection of Aβ Peptide in Human CSF Samples

Figure 12A:
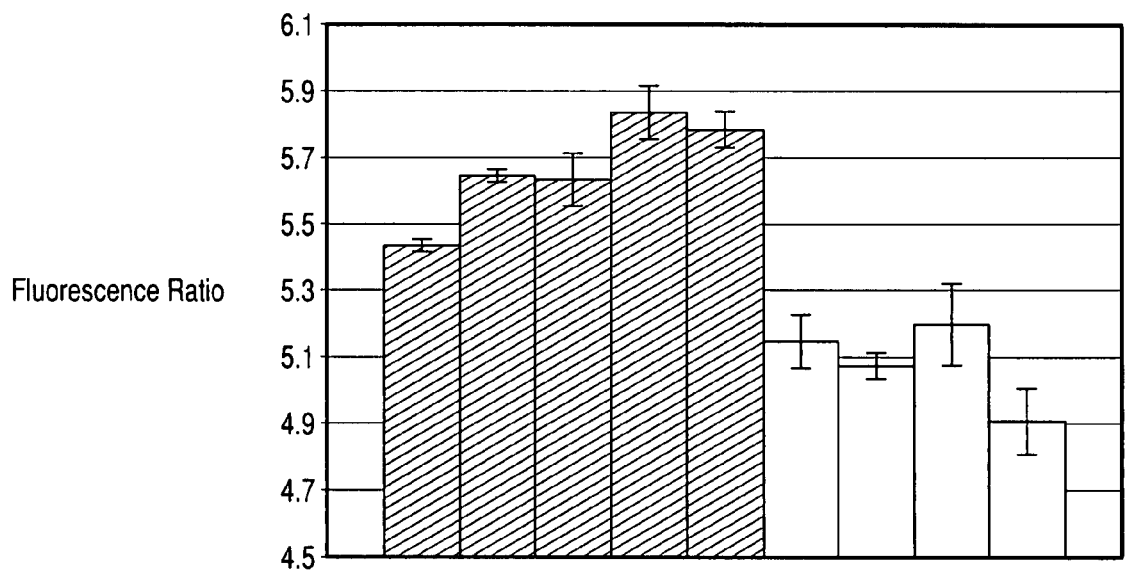
Figure 12B:
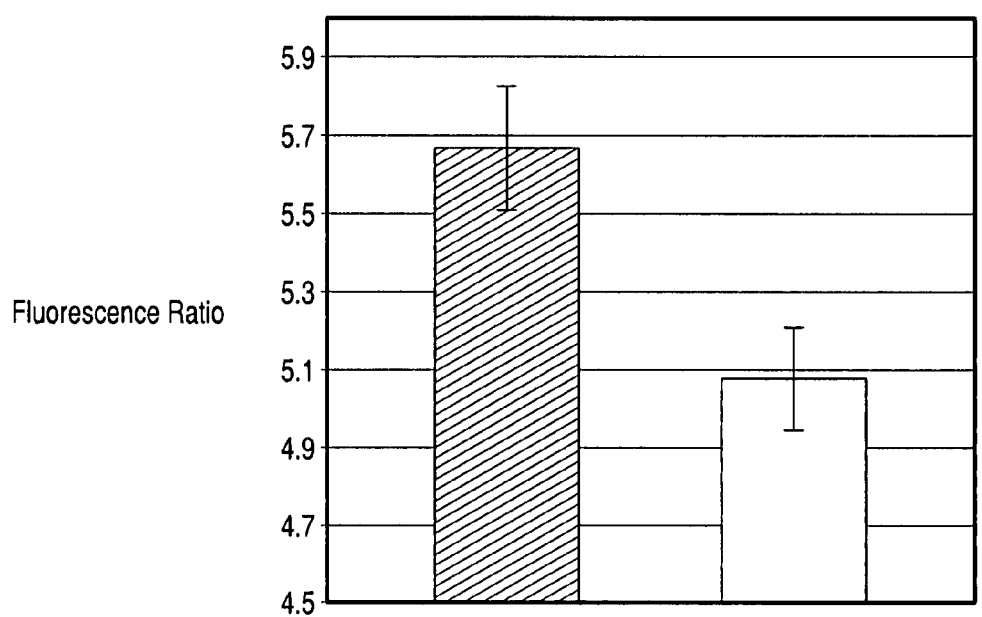
FIG. 12B presents the average data for each patient group.

A peptide probe specific for Aβ (SEQ ID NO:36) is used to detect Aβ40 and Aβ42 in samples of human cerebrospinal fluid (CSF) obtained from Alzheimer's patients and from age-matched healthy patients. The peptide probe is labeled at each terminus with pyrene. 40 μL samples of CSF are incubated with 2 μM peptide probe and allowed to incubate for 1 hour, prior to exciting at 350 nm and scanning fluorescence from 360 to 600 nm. The data is presented in FIG. 12 as the ratio of the excimeric region (430-530 nm) over the monomeric region (370-385 nm). The peptide probe is able to stratify Alzheimer's patients (black) from age-matched healthy patients (white). The results shown in FIG. 12 have a p value=0.0005. FIG. 12A presents the data for each patient, while FIG. 12B presents the average data for each patient group. The patient samples also were assayed for Aβ protein using a commercial antibody-based kit (Biosource ELISA, Invitrogen), but that assay did not detect Aβ protein, indicating that the peptide probe is more sensitive.

A similar assay is carried out using a biotinylated peptide probe specific for Aβ (SEQ ID NO:36) that is immobilized on magnetic beads and 200 μL samples of serum from Alzheimer's patients and age-matched healthy patients. Biotinylated peptide probe is immobilized to Dynal magnetic beads coated with streptavidin. These beads are incubated directly with the serum samples for 1 hour, then the magnetic beads and the captured material are pulled down to remove the serum samples. Then, 200 μl of dipyrene labeled peptide probe (SEQ ID NO:36) at 2 μM concentration preequilibrated in 40% trifluoroethanol:60% 10 mM Tris, pH 7.4 is added directly to the beads and the captured material and allowed to incubate for an additional 3-5 hours prior to pulling down the magnetic beads and transferring the liquid to a microtiter plate for analysis as described above.

Figure 13:
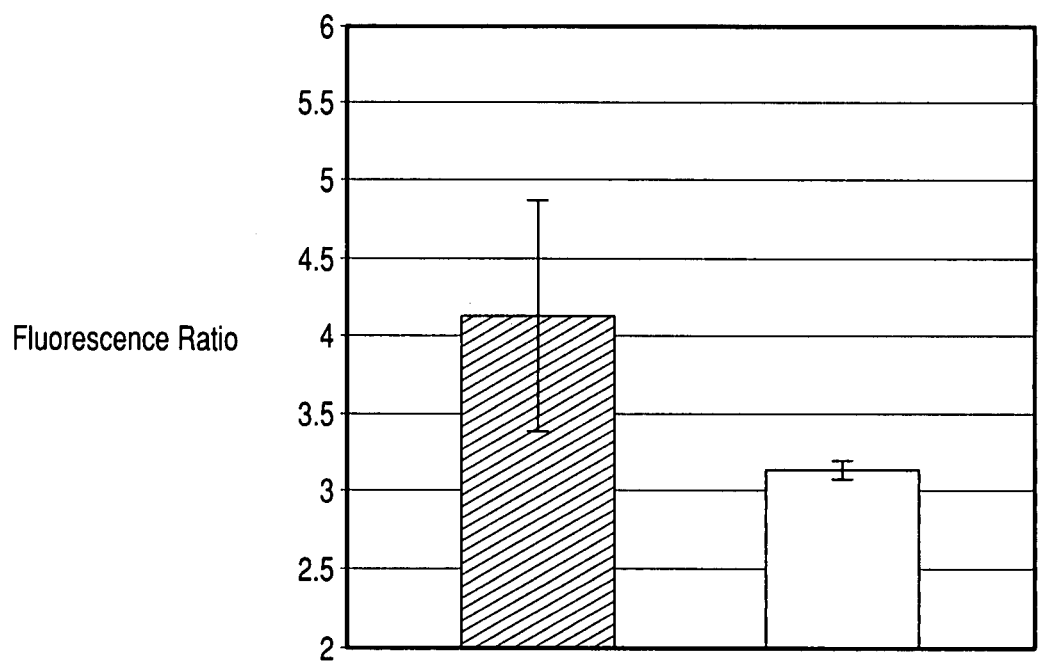
FIG. 13 illustrates the ability of an immobilized peptide probe specific for Aβ (SEQ ID NO:36) to detect Aβ40 and Aβ42 in samples of human serum from Alzheimer's patients. The peptide probe is able to stratify Alzheimer's patients (black) from age-matched healthy patients (white) with a p value=0.045.

The peptide probe is able to stratify Alzheimer's patients (black) from age-matched healthy patients (white). The results, shown in FIG. 13, have a p value of 0.045. The patient samples also were assayed for Aβ protein using a commercial antibody-based kit (Biosource ELISA, Invitrogen), but again that assay did not detect Aβ protein, indicating that the peptide probe is more sensitive.

Example 11

Targeting Aβ Plaques

The following illustrates the ability of peptide probes to target Aβ plaques (e.g., insoluble self-aggregates of Aβ protein associated with Alzheimer's disease) both in vitro and in vivo. A peptide probe specific for Aβ (SEQ ID NO:36) and labeled at each terminus with pyrene is used.

In vitro studies are carried out on brain sections from transgenic mice over-expressing human APP751 with London and Swedish mutations (hAPP751$_{SL}$). This protein is an Aβ mutant that forms neuritic plaques in the transgenic mice. Tissue from non-transgenic littermate mice served as control tissue.

Two different types of tissue slices are evaluated: cyro-cut (frozen and sliced) and paraffin embedded and sliced. The peptide probe is incubated on the brain slices and binding of the peptide probe to the brain, and to the amyloid deposits/ plaques in particular, are qualitatively evaluated. For reference purposes, consecutive slices are immunohistochemically stained with an anti-Aβ antibody, the 6E10 antibody or Thioflavin S. The use of anti-Aβ controls confirms the specificity of the staining on neuritic plaques.

Images are recorded on a Nikon E800 microscope with a mounted PixelFly camera. For tiled image recordings, the microscope is equipped with a StagePro software controlled automatic table. Images of peptide probe staining and antibody and ThioflavinS staining, respectively, are overlaid in Adobe Photo Shop software Using 0.5 ml/mg concentration of peptide probe, plaque-specific staining is apparent, both on paraffin or cryo-cut slices. Overlaying with antibody staining from consecutive slices revealed that staining on paraffin slices is more specific to plaques than staining on cryo-cut slices. In the latter samples, cells from the neuronal layer of the hippocampus are marked, as are brain tissue around plaques in the cortex. Thus, the quality of the stain may be better on paraffin sections. In addition to staining neuritic plaques, the peptide probe also specifically stained human amyloid peptide bearing blood vessels, which are typically present in hAPP751$_{SL}$ transgenics.

In vivo studies use four homozygous hAPP751 SL transgenic 10 month old mice and four littermate controls (siblings not carrying the transgene). The labeled peptide probe is administered intranasally, at 10 μl liquid per administration (at concentrations of from 0.1 to 2.0 mg/ml) with an administration interval of a planned half of an hour, adjusted according to the condition of the animal after treatment.

At the end of the treatment, mice are sacrificed and CSF and brains are extracted. (All mice are sedated by standard inhalation anaesthesia, Isofluran, Baxter).

Cerebrospinal fluid is obtained by blunt dissection and exposure of the foramen magnum. Upon exposure, a Pasteur pipette is inserted to the approximate depth of 0.3-1 mm into the foramen magnum. CSF is collected by suctioning and capillary action until flow fully ceases. CSF is immediately frozen and kept at −80° C. until use.

After CSF sampling, the stomach, stomach content and the brains are rapidly removed. Brains are hemisected, and the right hemisphere of all mice are immersion fixed in freshly produced 4% Paraformaldehyde/PBS (pH 7.4) for one hour at room temperature, and transferred to a 15% sucrose/PBS solution for 24 hours to ensure cryoprotection. Thereafter, brains are frozen in liquid isopentane on the next day and stored at −80° C. until used for histological investigations. The other brain half is immediately shock frozen in liquid isopentane for future use.

Images are recorded from transgenic mice treated with the highest dose of peptide probe and from control mice and from a transgenic vehicle control (e.g., the diluent used for the peptide probe) to confirm that the peptide probe crosses the blood-brain barrier (BBB), which it does.

To assess the specificity of staining by the peptide probe, fluorescence is excited using a UV-2A and B-1 E filter of a microscope to detect probable auto-fluorescence in the lower spectrum. Fluorescent parts are recorded in the consecutive slice to ensure that impurity (e.g. dust) does not causes fluorescence. Transgenic slices are stained with ThioflavinS to assess plaque load.

As noted above, hAPP751$_{SL}$ transgenic mice express hAPP in certain blood vessels in the periphery of the brain. The peptide probe binds to the amyloid and agglomerates outside the blood vessel in the brain. In the nontransgenic mice, the peptide probe reaches the olfactory bulb, but does not bind to a specifiable morphological structure.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with the true scope and spirit of the invention being indicated by the following claims.

What is claimed is:

1. A method for identifying a target amyloid beta protein present in a sample in a specific state of self-aggregation, comprising:
   (a) contacting the sample with a peptide probe that preferentially binds to the target protein in a specific state of self-aggregation selected from the group consisting of soluble oligomers, insoluble self-aggregates, amorphous self-aggregates, protofibrils, and fibrils, wherein the peptide probe does not bind in a dose-dependent manner to monomers, wherein the peptide probe consists of from 20 to 40 amino acid residues and comprises an amino acid sequence that is at least 60% identical to an amino acid sequence selected from SEQ ID NO:36 and SEQ ID NO:45; and
   (b) detecting any binding between the peptide probe and any target protein present in the specific state of self-aggregation, thereby identifying any target protein present in the specific state of self-aggregation.

2. The method of claim 1, wherein the peptide probe preferentially binds to the target protein in a specific state of self-aggregation selected from the group consisting of soluble oligomers.

3. The method of claim 2, wherein the peptide probe preferentially binds to insoluble self-aggregates of the target protein selected from the group consisting of insoluble amorphous self-aggregates, protofibrils, and fibrils.

4. The method of claim 1, wherein the peptide probe further comprises a detectable label.

5. The method of claim 1, wherein the peptide probe comprises an amino acid sequence selected from SEQ ID NO:36 and SEQ ID NO:45.

6. The method of claim 1, wherein the peptide probe is immobilized on a solid support.

7. The method of claim 1, wherein the peptide probe comprises an amino acid sequence that is at least 65% identical to an amino acid sequence selected from SEQ ID NO:36 and SEQ ID NO:45.

8. The method of claim 1, wherein the peptide probe comprises an amino acid sequence that is at least 80% identical to an amino acid sequence selected from SEQ ID NO:36 and SEQ ID NO:45.

9. The method of claim 1, wherein the peptide probe comprises an amino acid sequence that is at least 85% identical to an amino acid sequence selected from SEQ ID NO:36 and SEQ ID NO:45.

* * * * *

SEQUENCE LISTING

```
<160> NUMBER OF SEQ ID NOS: 45

<210> SEQ ID NO 1
<211> LENGTH: 33
<212> TYPE: PRT
<213> ORGANISM: Homo sapiens

<400> SEQUENCE: 1

Val Val Ala Gly Ala Ala Ala Ala Gly Ala Met His Lys Met Asn Thr
1               5                   10                  15

Lys Pro Lys Met Lys His Met Ala Gly Ala Ala Ala Gly Ala Val
            20                  25                  30

Val

<210> SEQ ID NO 2
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      probe

<400> SEQUENCE: 2

Lys Pro Lys Thr Asn Met Lys His Met Ala Gly Ala Ala Ala Ala Gly
1               5                   10                  15

Ala Val Val

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 3

Met Lys His Met Ala Gly Ala Ala Ala Ala Gly Ala Val Val
1               5                   10

<210> SEQ ID NO 4
<211> LENGTH: 40
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 5
<211> LENGTH: 24
<212> TYPE: PRT
<213> ORGANISM: Homo sapiens

<400> SEQUENCE: 5

Glu Val His His Gln Lys Leu Val Phe Phe Ala Glu Asp Val Gly Ser
1               5                   10                  15

Asn Lys Gly Ala Ile Ile Gly Leu
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 6

Glu Val Arg His Gln Lys Leu Val Phe Phe Ala Glu Asp Val Gly Ser
1               5                   10                  15

Asn Lys Gly Ala Ile Ile Gly Leu
            20

<210> SEQ ID NO 7
<211> LENGTH: 11
<212> TYPE: PRT
<213> ORGANISM: Homo sapiens
```

```
<400> SEQUENCE: 7

Gly Ser Asn Lys Gly Ala Ile Ile Gly Leu Met
1               5                   10

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 8

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys
            20                  25

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 9

Gln Gln Gln Gln Gln Gln Gln Gln Gln Gln Gln Gln Gln Gln Gln
1               5                   10                  15

Gln Gln Gln Gln Gln Gln Gln Gln
            20

<210> SEQ ID NO 10
<211> LENGTH: 19
<212> TYPE: PRT
<213> ORGANISM: Homo sapiens

<400> SEQUENCE: 10

Lys Pro Lys Thr Asn Leu Lys His Val Ala Gly Ala Ala Ala Ala Gly
1               5                   10                  15

Ala Val Val

<210> SEQ ID NO 11
<211> LENGTH: 38
<212> TYPE: PRT
<213> ORGANISM: Homo sapiens

<400> SEQUENCE: 11

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala
        35

<210> SEQ ID NO 12
<211> LENGTH: 25
<212> TYPE: PRT
<213> ORGANISM: Homo sapiens
```

<400> SEQUENCE: 12

Met Ala Glu Ser His Leu Leu Gln Trp Leu Leu Leu Leu Pro Thr
1               5                   10                  15

Leu Cys Gly Pro Gly Thr Ala Ala Trp
            20                  25

<210> SEQ ID NO 13
<211> LENGTH: 253
<212> TYPE: PRT
<213> ORGANISM: Mus sp.

<400> SEQUENCE: 13

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 14
<211> LENGTH: 254
<212> TYPE: PRT
<213> ORGANISM: Mus sp.

<400> SEQUENCE: 14

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

-continued

```
Tyr Pro Pro Gln Gly Gly Thr Trp Gly Gln Pro His Gly Gly Gly Trp
         50                  55                  60

Gly Gln Pro His Gly Gly Ser Trp Gly Gln Pro His Gly Gly Ser Trp
 65                  70                  75                  80

Gly Gln Pro His Gly Gly Gly Trp Gly Gln Gly Gly Gly Thr His Asn
                 85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Arg Ser Thr Val Val Ala Arg Leu Lys Ala Ala Ala Val
1               5                   10

<210> SEQ ID NO 16
<211> LENGTH: 818
<212> TYPE: PRT
<213> ORGANISM: Homo sapiens

<400> SEQUENCE: 16

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95
```

```
Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
            115                 120                 125

Ala Ile Phe Thr Val Gln Leu Asp Asp Tyr Leu Asn Gly Arg Ala Val
            130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Val Ala Ser Gly Phe
                165                 170                 175

Lys His Val Val Pro Asn Glu Val Val Gln Arg Leu Phe Gln Val
            180                 185                 190

Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
            210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
            275                 280                 285

Lys Glu Asp Ala Ala Asn Arg Lys Leu Ala Lys Leu Tyr Lys Val Ser
            290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
            355                 360                 365

Met Asp Tyr Pro Lys Gln Thr Gln Val Ser Val Leu Pro Glu Gly Gly
            370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
            435                 440                 445

Ile Trp Arg Ile Glu Gly Ser Asn Lys Val Pro Val Asp Pro Ala Thr
            450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
            515                 520                 525
```

```
Gly Lys Glu Pro Ala His Leu Met Ser Leu Phe Gly Lys Pro Met
        530                 535                 540

Ile Ile Tyr Lys Gly Gly Thr Ser Arg Glu Gly Gln Thr Ala Pro
545                 550                 555                 560

Ala Ser Thr Arg Leu Phe Gln Val Arg Ala Asn Ser Ala Gly Ala Thr
            565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
            595                 600                 605

Gly Ala Ser Glu Ala Glu Lys Thr Gly Ala Gln Glu Leu Leu Arg Val
610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
        675                 680                 685

Met Gln Glu Asp Leu Ala Thr Asp Asp Val Met Leu Leu Asp Thr Trp
690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
            725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
            755                 760                 765

Ser Val Asp Pro Leu Asp Arg Ala Met Ala Glu Leu Ala Ala Tyr Glu
            770                 775                 780

Arg Leu Lys Ala Thr Gln Val Ser Lys Gly Ile Arg Asp Asn Glu Arg
785                 790                 795                 800

Ser Gly Arg Ala Arg Val His Val Ser Glu Glu Gly Thr Glu Pro Glu
            805                 810                 815

Ala Met

<210> SEQ ID NO 17
<211> LENGTH: 145
<212> TYPE: PRT
<213> ORGANISM: Homo sapiens

<400> SEQUENCE: 17

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
                20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
        50                  55                  60

Asn Asp Met Tyr His Ser Arg Ala Leu Gln Val Val Arg Ala Arg Gln
65                  70                  75                  80
```

```
Ile Val Ala Gly Val Asn Tyr Phe Leu Asp Val Glu Leu Gly Arg Thr
                85                  90                  95
Thr Cys Thr Lys Thr Gln Pro Asn Leu Asp Asn Cys Pro Phe His Asp
            100                 105                 110
Gln Pro His Leu Lys Arg Lys Ala Phe Cys Ser Phe Gln Ile Tyr Ala
        115                 120                 125
Val Pro Trp Gln Gly Thr Met Thr Leu Ser Lys Ser Thr Cys Gln Asp
    130                 135                 140
Ala
145

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 18

Glu Glu Glu Val Ser Ala Asp Met Pro Pro Pro Met Asp Ala Ser
1               5                   10                  15

Val Glu Glu Glu
            20

<210> SEQ ID NO 19
<211> LENGTH: 314
<212> TYPE: PRT
<213> ORGANISM: Homo sapiens

<400> SEQUENCE: 19

Met Ala Thr Leu Glu Lys Leu Met Lys Ala Phe Glu Ser Leu Lys Ser
1               5                   10                  15
Phe Gln Gln Gln Gln Gln Gln Gln Gln Gln Gln Gln Gln Gln Gln Gln
            20                  25                  30
Gln Gln Gln Gln Gln Gln Gln Pro Pro Pro Pro Pro Pro Pro Pro Pro
        35                  40                  45
Pro Pro Pro Gln Leu Pro Gln Pro Pro Gln Ala Gln Pro Leu Leu
    50                  55                  60
Pro Gln Pro Gln Pro Pro Pro Pro Pro Pro Pro Pro Gly Pro
65                  70                  75                  80
Ala Val Ala Glu Glu Pro Leu His Arg Pro Lys Lys Glu Leu Ser Ala
                85                  90                  95
Thr Lys Lys Asp Arg Val Asn His Cys Leu Thr Ile Cys Glu Asn Ile
            100                 105                 110
Val Ala Gln Ser Val Arg Asn Ser Pro Glu Phe Gln Lys Leu Leu Gly
        115                 120                 125
Ile Met Glu Leu Phe Leu Leu Cys Ser Asp Asp Ala Glu Ser Asp Val
    130                 135                 140
Arg Met Val Ala Asp Glu Cys Leu Asn Lys Val Ile Lys Ala Leu Met
145                 150                 155                 160
Asp Ser Asn Leu Pro Arg Leu Gln Leu Glu Leu Tyr Lys Glu Ile Lys
                165                 170                 175
Lys Asn Gly Ala Pro Arg Ser Leu Arg Ala Ala Leu Trp Arg Phe Ala
            180                 185                 190
Glu Leu Ala His Leu Val Arg Pro Gln Lys Cys Arg Pro Tyr Leu Val
        195                 200                 205
```

```
Asn Leu Leu Pro Cys Leu Thr Arg Thr Ser Lys Arg Pro Glu Glu Ser
    210                 215                 220

Val Gln Glu Thr Leu Ala Ala Val Pro Lys Ile Met Ala Ser Phe
225                 230                 235                 240

Gly Asn Phe Ala Asn Asp Asn Glu Ile Lys Val Leu Leu Lys Ala Phe
                245                 250                 255

Ile Ala Asn Leu Lys Ser Ser Ser Pro Thr Ile Arg Arg Thr Ala Ala
                260                 265                 270

Gly Ser Ala Val Ser Ile Cys Gln His Ser Arg Arg Thr Gln Tyr Phe
                275                 280                 285

Tyr Ser Trp Leu Leu Asn Val Leu Leu Gly Leu Leu Pro Val Glu
    290                 295                 300

Asp Glu His Ser Thr Leu Leu Ile Leu Gly
305                 310

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 20

Gln Gln Gln Gln Gln Gln Gln Gln Gln Gln Gln Gln Gln Gln Gln Gln
1               5                   10                  15

Gln

<210> SEQ ID NO 21
<211> LENGTH: 89
<212> TYPE: PRT
<213> ORGANISM: Homo sapiens

<400> SEQUENCE: 21

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
                20                  25                  30

Arg Lys Cys Asn Thr Ala Thr Cys Ala Thr Gln Arg Leu Ala Asn Phe
            35                  40                  45

Leu Val His Ser Ser Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 22

Leu Ala Asn Phe Val
1               5
```

```
<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 23

Val Phe Asn Ala Leu Pro Pro Pro Leu Ala Lys Phe Val
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 24

Phe Leu Val His Ser Ser
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 25

Ser Ser His Val Leu Phe Pro Pro Pro Phe Leu Val His Ser Ser
1               5                   10                  15

<210> SEQ ID NO 26
<211> LENGTH: 147
<212> TYPE: PRT
<213> ORGANISM: Homo sapiens

<400> SEQUENCE: 26

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145
```

```
<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 27

Glu Ser Val Phe Val Leu Gly Ala Leu Pro Pro Pro Leu Ala Gly
1               5                   10                  15

Leu Val Phe Val Ser Glu
            20

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 28

Val Ala Ala Ala Lys Leu Arg Ala Val Val Thr Ser Arg Gln Pro Pro
1               5                   10                  15

Pro Pro Gln Arg Ser Thr Val Val Ala Arg Leu Lys Ala Ala Ala Val
            20                  25                  30

<210> SEQ ID NO 29
<211> LENGTH: 33
<212> TYPE: PRT
<213> ORGANISM: Mus sp.

<400> SEQUENCE: 29

Val Val Ala Gly Ala Ala Ala Gly Ala Val His Lys Leu Asn Thr
1               5                   10                  15

Lys Pro Lys Leu Lys His Val Ala Gly Ala Ala Ala Gly Ala Val
            20                  25                  30

Val

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Ala Val
1

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Ala Ala Ala Lys Leu Arg Ala Val Val Thr Ser Arg Gln
1               5                   10
```

```
<210> SEQ ID NO 32
<211> LENGTH: 42
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 32

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Val Ala Gly Ala Ala Ala Ala Gly Ala Met His Lys Met Asn Thr
1               5                   10                  15

Lys Pro Lys Met Lys His Met Ala Gly Ala Ala Ala Gly Ala Val
            20                  25                  30

Val Lys

<210> SEQ ID NO 34
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Val Ala Gly Ala Ala Ala Ala Gly Ala Val His Lys Leu Asn Thr
1               5                   10                  15

Lys Pro Lys Leu Lys His Val Ala Gly Ala Ala Ala Gly Ala Val
            20                  25                  30

Val Lys

<210> SEQ ID NO 35
<211> LENGTH: 19
<212> TYPE: PRT
<213> ORGANISM: Homo sapiens

<400> SEQUENCE: 35

Leu Val Phe Phe Ala Glu Asp Val Gly Ser Asn Lys Gly Ala Ile Ile
1               5                   10                  15

Gly Leu Met

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      probe
```

-continued

```
<400> SEQUENCE: 36

Lys Leu Val Phe Phe Ala Glu Asp Val Gly Ser Asn Lys Gly Ala Ile
1               5                   10                  15

Ile Gly Leu Met
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 37

Leu Val Phe Phe Ala Glu Asp Val Gly Ser Asn Lys Gly Ala Ile Ile
1               5                   10                  15

Gly Leu Met Lys
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 38

Lys Leu Val Phe Phe Ala Glu Asp Val Gly Ser Asn Lys Gly Ala Ile
1               5                   10                  15

Ile Gly Leu Met Lys
            20

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 39

Lys Pro Lys Thr Asn Met Lys His Met Ala Gly Ala Ala Ala Ala Gly
1               5                   10                  15

Ala Val Val

<210> SEQ ID NO 40
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Val Ala Gly Ala Ala Ala Ala Gly Ala Met His Lys Met Asn Thr
1               5                   10                  15

Lys Pro Lys Met Lys His Met Ala Gly Ala Ala Ala Gly Ala Val
            20                  25                  30

Val
```

```
<210> SEQ ID NO 41
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Val Ala Gly Ala Ala Ala Ala Gly Ala Met His Lys Met Lys Pro
1               5                   10                  15

Lys Thr Asn Met Lys His Met Ala Gly Ala Ala Ala Gly Ala Val
            20                  25                  30

Val

<210> SEQ ID NO 42
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Val Ala Gly Ala Ala Ala Ala Gly Ala Val His Lys Met Lys Pro
1               5                   10                  15

Lys Thr Asn Met Lys His Val Ala Gly Ala Ala Ala Gly Ala Val
            20                  25                  30

Val

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 43

Val Val Ala Gly Ala Ala Ala Ala Gly Ala Val His Lys Met Asn Thr
1               5                   10                  15

Lys Pro Lys Met Lys His Val Ala Gly Ala Ala Ala Gly Ala Val
20                  25                  30

Val

<210> SEQ ID NO 44
<211> LENGTH: 42
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 44

Asp Ala Glu Phe Arg His Asp Ser Gly Tyr Glu Val His His Gln Lys
1               5                   10                  15

Leu Val Ser Phe Ala Glu Asp Val Gly Ser Asn Lys Gly Ala Ile Ile
            20                  25                  30

Gly Pro Met Val Gly Gly Val Val Ile Ala
            35                  40
```

-continued

```
<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 45

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30
```